United States Patent
Badran et al.

(10) Patent No.: US 12,139,708 B2
(45) Date of Patent: Nov. 12, 2024

(54) FRAMESHIFT SUPPRESSOR tRNA COMPOSITIONS AND METHODS OF USE

(71) Applicants: Massachusetts Institute of Technology, Cambridge, MA (US); The Broad Institute, Inc., Cambridge, MA (US)

(72) Inventors: Ahmed Hussein Badran, Cambridge, MA (US); Erika Alden DeBenedictis, Cambridge, MA (US); Kevin Michael Esvelt, Newton, MA (US)

(73) Assignees: Massachusetts Institute of Technology, Cambridge, MA (US); The Borad Institute, Inc., Cambridge, MA (US)

( * ) Notice: Subject to any disclaimer, the term of this patent is extended or adjusted under 35 U.S.C. 154(b) by 927 days.

(21) Appl. No.: 16/894,359

(22) Filed: Jun. 5, 2020

(65) Prior Publication Data

US 2020/0385724 A1 Dec. 10, 2020

Related U.S. Application Data

(60) Provisional application No. 62/989,920, filed on Mar. 16, 2020, provisional application No. 62/936,734, filed on Nov. 18, 2019, provisional application No. 62/858,717, filed on Jun. 7, 2019.

(51) Int. Cl.
| | |
|---|---|
| C12N 15/113 | (2010.01) |
| C07H 21/02 | (2006.01) |
| C12N 15/10 | (2006.01) |
| C12N 15/74 | (2006.01) |
| C12N 15/85 | (2006.01) |

(52) U.S. Cl.
CPC ........... *C12N 15/113* (2013.01); *C07H 21/02* (2013.01); *C12N 15/1058* (2013.01); *C12N 15/74* (2013.01); *C12N 15/8509* (2013.01)

(58) Field of Classification Search
CPC .. C12N 15/113; C12N 15/1058; C12N 15/74; C12N 15/8509; C12N 2320/11; C12N 2320/13; C12N 2330/31; C12N 15/63; C12N 15/11; C07H 21/02; C12P 21/02
See application file for complete search history.

(56) References Cited

U.S. PATENT DOCUMENTS

| | | | |
|---|---|---|---|
| 7,045,337 B2 | 5/2006 | Schultz et al. | |
| 2012/0077186 A1 | 3/2012 | Skach et al. | |
| 2012/0264926 A1 | 10/2012 | Chin et al. | |
| 2016/0355552 A1* | 12/2016 | Fasan ..................... | C40B 50/06 |

FOREIGN PATENT DOCUMENTS

| | | |
|---|---|---|
| WO | 2011/077075 A1 | 6/2011 |
| WO | 2015/120287 A3 | 8/2015 |
| WO | 2016/077052 A3 | 5/2016 |

OTHER PUBLICATIONS

Normanly, Jennifer, et al. "Construction of two Escherichia coli amber suppressor genes: tRNAPheCUA and tRNACysCUA." Proceedings of the National Academy of Sciences 83.17 (1986): 6548-6552 (Year: 1986).*
Hudziak, Robert M., et al. "Establishment of mammalian cell lines containing multiple nonsense mutations and functional suppressor tRNA genes." Cell 31.1 (1982): 137-146 (Year: 1982).*
Welch, Jonathan B., Derek R. Duckett, and David MJ Lilley. "Structures of bulged three-way DNA junctions." Nucleic acids research 21.19 (1993): 4548-4555 (Year: 1993).*
Vargas-Rodriguez (Current opinion in chemical biology 46 (2018): 115-122; herein after "Vargas") (Year: 2018).*
Rackham, Oliver, et al., "A network of orthogonal ribosome mRNA pairs." J. Nat Chem Biol., vol. 1, No. 3, 159-166 (2005).
Ravikumar, Arjun et al.,"An orthogonal DNA replication system in yeast." Nature Chemical Biology, vol. 10, Mar. 2014.
Riddle, D. L. et al., "Frameshift Suppression: a Nucleotide Addition in the Anticodon of a Glycine Transfer RNA." Nature New Biology vol. 242, pp. 230-234 (1973).
Salazar, J.C., et al., "Coevolution of an aminoacyl-tRNA synthetase with its tRNA substrates." PNAS, Nov. 25, 2003, vol. 100, No. 24, pp. 13863-138688.
Salman, Ashraf, S., et al., "The uridine in "U-turn": Contributions to IRNA-ribosomal binding." RNA (1999), 5:503-511.
Salser, W., et al., "The Influence of the Reading Context upon the Suppression of Nonsense Codons, III." Cold Spring Harb. Symp. Quant. Biol. 34, 513-520 (1969).
Shepherd, J., et al., "Bacterial transfer RNAs." FEMS Microbiology Reviews, fuv004, 39, 2015, 280-300.
Sonneborn, T. M., "Degeneracy of the Genetic Code: Extent, Nature, and Genetic Implications." In Evolving Genes and Proteins (eds. Bryson, V. & Vogel, H.J.) 377-397 (Academic Press, (1965).
Sroga, G. E., et al., "Insertion (sufB) in the anticodon loop or base substitution (sufC) in the anticodon stem of tRNAPro2 from *Salmonella typhimurium* induces suppression of frameshift mutations." Nucleic Acids Research, vol. 20, No. 13, 1992, p. 3463-3469.
Tate, C. G., et al., "Mapping, Cloning, Expression, and Sequencing of the rhaT Gene, Which Encodes a Novel L-Rhamnose-H+ Transport Protein in *Salmonella typhimurium* and *Escherichia coli*" J Biol. Chem., vol. 267, No. 10, Issue of Apr. 5, 1992, pp. 6923-6932.
Thuronyi, B.W., et al., "Continuous evolution of base editors with expanded target compatibility and improved activity." Nat Biotechnol. Sep. 2019 ; 37(9): 1070-1079.

(Continued)

*Primary Examiner* — Nancy J Leith
*Assistant Examiner* — Kyle Thomas Rega
(74) *Attorney, Agent, or Firm* — Pierce Atwood LLP

(57) ABSTRACT

The invention, in part, includes compositions comprising quadruplet decoding tRNAs and their encoding sequences. The invention also includes assay methods to assess quadruplet decoding as well as methods of preparing quadruplet decoding suppression tRNAs.

20 Claims, 50 Drawing Sheets
Specification includes a Sequence Listing.

(56) References Cited

OTHER PUBLICATIONS

Wang, K., et al., "Evolved orthogonal ribosomes enhance the efficiency of synthetic genetic code expansion." Nat. Biotechnol. vol. 25, No. 7, 770-777 (2007) p. 1-8.
Wang, L., et al., "A New Functional Suppressor IRNA/Aminoacyl-tRNA Synthetase Pair for the in Vivo Incorporation of Unnatural Amino Acids into Proteins." J Am. Chem. Soc. 122, 5010-5011 (2000).
Wang, Lei et al., "A general approach for the generation of orthogonal tRNAs." Chemistry & Biology, 8 (2001) 883-890.
Wang, Lei, et al. "Expanding the genetic code of *Escherichia coli*." Science, American Association for the Advancement of Science vol. 292, Apr. 20, 2001 (Apr. 20, 2001), pp. 498-500.
Wang, N., et al., "Systematic Evolution and Study of UAGN Decoding tRNAs in a Genomically Recoded Bacteria." Sci. Rep. 6, 20 21898 (2016).
Wang, T., Badran, et al., "Continuous directed evolution of proteins with improved soluble expression." Nat Chem Biol. Oct. 2018; 14(10): 972-980.
Yahata, H., et al., "Adjacent effect on suppression efficiency." Mol. Gen. Genet. 106, p. 208-212 (1970).
Yarus, M. "Translational Efficiency of Transfer RNA's: Uses of an Extended Anticodon." (1982). Science 218, 646-652.
Young, D.D., et al., An Evolved Aminoacyl-tRNA Synthetase with Atypical Polysubstrate Specificity (2011) Biochemistry 50, 42 1894-1900.
Yourno, J. et al., "Restoration of in-phase translation by an unlinked suppressor of a frameshift mutation in *Salmonella typhimurium*." Nature 225, pp. 422-426 (1970).
Zhang, S. P., et al., "Low-usage codons in *Escherichia coli*, yeast, fruit fly and primates." Gene, vol. 105, Issue 1, pp. 61-72 (1991).
Bossi et al., "Four-Base Codons ACCA, ACCU and ACCC Are Recognized by Frameshift Suppressor sufJ." Cell, vol. 26,489-496, Aug. 1981.
International Search Report and Written Opinion of the International Searching Authority from corresponding international patent application PCT/US2020/036399 mailed on Dec. 23, 2020.
Akaboshi, E., et al., "Effect of neighboring nucleotide sequences on suppression efficiency in amber mutants of T4 phage lysozyme." Molecular and General Genetics MGG vol. 149, pp. 1-4 (1976).
Amann, E. et al.,"ATG vectors' for regulated high-level expression of cloned genes in *Escheriichia coli*." J. Gene, 40 (1985) 183-190.
Anderson, J. C. et al., "Exploring the Limits of Codon and Anticodon Size." Chemistry & Biology, vol. 9, 237-244, Feb. 2002.
Anderson, J.C., et al. "An expanded genetic code with a functional quadruplet codon." PNAS May 18, 2004 vol. 101, No. 20, pp. 7566-7571.
Atkins, J. F. et al., "A Gripping Tale of Ribosomal Frameshifting: Extragenic Suppressors of Frameshift Mutations Spotlight P-Site Realignment." Microbiology and Molecular Biology Reviews, Mar. 2009, p. 178-210.
Atkins, J.F., et al., "Culmination of a half-century quest reveals insight into mutant tRNA-mediated frameshifting after tRNA departure from the decoding site." PNAS Oct. 30, 2018 115 (44) 11121-11123.
Badran, A.H et al., "Development of potent in vivo mutagenesis plasmids with broad mutational spectra." Nature Communications I 6:8425 (2015) p. 1-10.
Bossi, L. et al., "Suppressor sufJ: A novel type of tRNA mutant that induces translational frameshifting." Proc. Nati. Acad. Sci. USA vol. 81, pp. 6105-6109, Oct. 1984.
Bryson, D.I., et al., "Continuous directed evolution of aminoacyl-tRNA synthetases." Nat Chem Biol. Dec. 2017; 13 (12): 1253-1260.
Carlson, E.D., et al., "Engineered ribosomes with tethered subunits for expanding biological function." Nature Communications, vol. 10, Article No. 3920 (2019) p. 1-13.
Chin, Jason W. "Expanding and reprogramming the genetic code." (2017), vol. 550, Nature 53.

Colby, D.S., et al., "A functional requirement for modification of the wobble nucleotide in the anticodon of a T4 suppressor tRNA" Cell Nov. 1976; 9(3):449-63.
Curran, J. F. et al., "Reading frame selection and transfer RNA anticodon loop stacking." Science Dec. 11, 1987: vol. 238, Issue 4833, pp. 1545-1550.
Davis, J. H., et al., "Design, construction and characterization of a set of insulated bacterial promoters." Nucleic Acids Research, vol. 39, Issue 3, Feb. 1, 2011, pp. 1131-1141.
Dickinson, B. C., et al., "A system for the continuous directed evolution of proteases rapidly reveals drug-resistance mutations." Nature Communications vol. 5, Article No. 5352 (2014) p. 1-8.
Dumas, A, et al., "Designing logical codon reassignment—Expanding the chemistry in biology." Chem. Sci., 2015, 6, 50-69.
English, Justin, et al., "VEGAS as a Platform for Facile Directed Evolution in Mammalian Cells." Cell 178, 748-761, Jul. 25, 2019.
Esvelt, K. M., et al., "A System for the Continuous Directed Evolution of Biomolecules." Nature. Apr. 28, 2011; 472 (7344): 499-503.
Fagan, C. E., et al., "Structural insights into translational recoding by frameshift suppressor tRNASufJ" RNA 20, 1944-1954 (2014).
Feinstein, S. I. et al., "Coding properties of an ochre-suppressing derivative of *Escherichia coli* tRNAITyr." J Mol. Biol., vol. 112, Issue 3, May 25, 1977, pp. 453-470.
Feinstein, S. I. et al., "Context effects on nonsense codon suppression in *Escherzchia coli*." Genetics 88, 201-219 (1978).
Fekner, T. et al., "The Pyrrolysine Translational Machinery as a Genetic-Code Expansion Tool." Curr Opin Chem Biol. Jun. 2011; 15(3): 387-391.
Fluck, M. M. et al., "Isolation and characterization of context mutations affecting the suppressibility of nonsense mutations." Molecular and General Genetics MGG vol. 177, pp. 615-627(1980).
Fluck, M. M., et al., "The influence of the reading context upon the suppression of nonsense codons." Molecular and General Genetics MGG vol. 151, pp. 137-149 (1977).
Gaber, R. F. et al., "Codon Recognition During Frameshift Suppression in *Saccharomyces cerevisiaet*." Molecular and Cellular Biology, Oct. 1984, p. 2052-2061.
Gaber, R. F. et al., "The yeast frameshift suppressor gene SUF16-1 encodes an altered glycine tRNA containing the four-base anticodon 3'-CCCG-5'." Gene, vol. 19, Issue 2, Sep. 1982, pp. 163-172.
Giege, R., et al., "Universal rules and idiosyncratic features in tRNA identity." Nucleic Acids Research, 1998, vol. 26, No. 22 p. 5017-5035.
Hoesl, M. G. et al., "Recent advances in genetic code engineering in *Escherichia coli*." Current Opinion in Biotechnology vol. 23, Issue 5, Oct. 2012, pp. 751-757.
Holliger, P., et al. "Crystal Structure of the Two N-terminal Domains of g3p from Filamentous Phage fd at 1.9 A: Evidence for Conformational Lability." J. Mol. Biol. (1999) 288, 649-657.
Hu et al., Evolved Cas9 variants with broad PAM compatibility and high DNA specificity (Apr. 5, 2018). Nature, 556 (7699) p. 57-63.
Hubbard, B.P., et al., "Continuous directed evolution of DNA-binding proteins to improve TALEN specificity." Nat Methods. Oct. 2015; 12(10): 939-942.
Italia, J.S., et al., "Mutually Orthogonal Nonsense-Suppression Systems and Conjugation Chemistries for Precise Protein Labeling at up to Three Distinct Sites." J. Am. Chem. Soc. 2019, 141, 15, p. 6204-6212.
Kleina, L. G., et al., "Construction of *Escherichia coil* Amber Suppressor tRNA Genes II . Synthesis of Additional tRNA Genes and Improvement of Suppressor Efficiency." J. Mol. Biol. (1990) 213, 705-717.
Lee, B. S., et al., "An efficient system for incorporation of unnatural amino acids in response to the four-base codon AGGA in *Escherichia coli*." Biochim. Biophys. Acta, vol. 1861, Issue 11, Part B, Nov. 2017, pp. 3016-3023.
Link, A.J., et al., "Non-canonical amino acids in protein engineering." (2003) Curr. Opin. Biotechnol., vol. 14, Issue 6, Dec. 2003, pp. 603-609.
Lubkowski, et al., "The structural basis of phage display elucidated by the cystal structure of the N-terminal domains of g3p." (1998) Nat. Struct. Biol. 5, 140-147.

(56) References Cited

OTHER PUBLICATIONS

Lubkowski, J., et al., "Filamentous phage infection: crystal structure of g3p in complex with its coreceptor, the C-terminal domain of TolA." Structure, vol. 7, Issue 6, Jun. 15, 1999, pp. 711-722.

Magliery, T. J., et al., "Expanding the genetic code: selection of efficient suppressors of four-base codons and identification of "shifty" four-base codons with a library approach in *Escherichia coli1*." J Mol Biol. Mar. 3, 20010; 307(3): 755-769.

Moore, B., et al., "Quadruplet Codons: Implications for Code Expansion and the Specification of Translation Step Size." J. Mol. Biol. (2000) 298, 195-209.

Neumann, H., et al., "Encoding multiple unnatural amino acids via evolution of a quadruplet-decoding ribosome." Nature 464, 441-444 (2010).

Normanly, J., et al., "Construction of *Escherichia coli* amber suppressor tRNA genes: III. Determination of tRNA specificity." J. Mol. Biol. vol. 213, Issue 4, Jun. 20, 1990, pp. 719-726.

Normanly, J., et al., "Construction of two Escherichia coli amber suppressor genes: tRNA Phe CUA and tRNA Cys CUA." Proc. Natl. Acad. Sci. USA vol. 83, pp. 6548-6552, Sep. 1986.

Nozawa, K. et al. "Pyrrolysyl-tRNA synthetase:tRNAPyl structure reveals the molecular basis of orthogonality." Nature. Feb. 26, 2009; 457(7233): 1163-1167.

O'Connor, M. "Insertions in the anticodon loop of tRNA1 Gln (sufG) and tRNALys promote quadruplet decoding of CAAA" Nucleic Acids Res. 30, 1985-1990 15 (2002).

O'Connor, M., et al., "tRNA hopping: enhancement by an expanded anticidon." EMBOJ 8, 4315-4323 (1989).

Packer, M. S., et al., "Phage-assisted continuous evolution of proteases with altered substrate specificity." Nat. Commun. 8, 956 (2017) p. 1-11.

Partial International Search Report from corresponding PCT/US2020/036399, mailed Nov. 2, 2020.

Peterson, J. et al., "New pSC101-derivative cloning vectors with elevated copy numbers." Plasmid. May 2008; 59 (3): 193-201.

Poole, E.S., et al. "The identity of the base following the stop codon determines the efficiency of invivo translational termination in *Escherichia coli*." (1995) EMBO J. 14, 151-158.

Pu, J., et al., "Evolution of a split RNA polymerase as a versatile biosensor." Nat Chem Biol. Apr. 2017; 13(4): 432-438.

\* cited by examiner

Figure 1

Naive suppressor tRNAs

| SEQ ID NO | Name | Sequence encoding suppressor (mutations capitalized) | Summary | % WT function (higher is better) |
|---|---|---|---|---|
| 1 | C-TAGA | gggggtaacaaagcgttatgcagattTCTAaatccgtctagtccgttcgactccggaaacgcgctcca | Minimally functional | 0.08 |
| 2 | E-TAGA | gtccccttcgtctagagcgccatcgacacaccgccctTCTAaacggcgtaacagaggtcgaatccctctaggggacgcca | Minimally functional | 0.38 |
| 3 | F-TAGA | gccggatagtcagtcgtagagcagcgggattTCTAaatccccgtcctgttcgattcgactcggcacca | Minimally functional | 0.01 |
| 4 | G-TAGA | gcgggtagttcaatggtagaacgagagagttTCTAaagctctatacgagggttcgattccctcggcctcca | Minimally functional | 0.11 |
| 5 | H-TAGA | gtgggctatagctcagttggtagagcgcctgaatTCTAattccagttgtgtgggttcgaatccattagccactcca | Minimally functional | 0.14 |
| 6 | Q-TAGA | tggggtatcgccaagcggtaagcgtaaatTCTAaattccggcattccgagttcgaatcctcgtaccccagcca | Functional | 1.40 |
| 7 | R-TAGA | gcatccgtagttcagctggatagagtactcgactTCTAaacccgagcgtcgaggttcgaatcctcccggatgcacca | Functional | 2.85 |
| 8 | S-TAGA | ggagagatgccggagtccgaagcgctgaacgacggagtctTCTAaaaccgagtagggcaactctaccggggttcaaatccc cctctctccgcca | Functional | 1.52 |
| 9 | W-TAGA | aggggctagttcaattggtagagcacccgtctTCTAaaaccgggtgttggaggttcgagtcctccgcccctgcca | Minimally functional | 0.45 |
| 10 | Y-TAGA | ggtggggttcccgagcggccaaaggggagcagagactTCTAaatctgccgtcgtcacagacttcgaaggttcgaatccttcccc caccacca | Functional | 1.96 |
| 11 | P-CCGG | cgggtgattgccgcagctggtagcgcacttcgttCCGGgacgaagtggtcgagagttcgaatcctctatcaccgacca | Minimally Functional | 0.32 |
| 12 | Q-CAGG | tggggtatcgccaagcggtaagcgcaccggattCCTGattccgccattccgagttcgaatcctcgtaccccagcca | Functional | 0.86 |
| 13 | R-CGTT | gcatccgtagCtcagctggatagtactcgctAACGaaccgagcgtcgaagttcgaaatcctcccggatgcacca | Functional | 1.26 |
| 14 | S-TCGG | ggagagatgccggagtccgaagcgctgaacgacggatctCCGGaaaaccgagtagggcaactctaccggggttcaaatccc cctctctccgcca | Minimally functional | 0.13 |
| 15 | T-ACGG | gccgatatagctcagttggtagagcagcgcattCCGTaatgcgaaggtcgtaggttcgactcctattatcggcacca | Functional | 0.39 |
| 22 | G-GGGG | gcgggctagttcaatggtagaacgagagagttCCCCaagctctatacgagggttcgattccctcggcccgctcca | Functional | 3.03 (a) |
| 23 | T-ACCA | gctgatatagctcagttggtagagcgcacccttTGGTaagggtgaggtcgccagttcgaatccttgcctatgccacca | Functional | 1.87 (b) |

(a) and (b) previously described in the literature.

Figure 2

Evolved suppressors

| SEQ ID NOS | Name | Sequence encoding suppressor tRNA (mutations capitalized) | % of WT Function | % WT function if unevolved |
|---|---|---|---|---|
| 16 | Y-UAGA-opt1 | ggttggttcccgagcggccaaagggagcagaACTCTAaatctgccgtcacagacttcgaagttcgaatcttccccaccacca | 10.06 | 2.12 |
| 17 | R-UAGA-opt1 | gcatccgtagCtcagctcggatagagtactcggcfTCTAaaccgaTcggtcggagttcgaatctcccggatgcacca | 7.90 | 3.06 |
| 18 | Q-UAGA-opt1 | tggggtatgccaagcgtaagcgggacaccggaCtTCTAattccggcattcgagttcgaatcctcgtacccagcca | 11.09 | 1.52 |
| 19 | Q-UAGA-opt2 | tggggtatgccaagcggtaagcaccggaCtTCTAattccggcatccgagttcgaatcctcgtacccagcca | 8.05 | 1.52 |
| 20 | SerU-UAGA-"v1" | ggagagatgccggagcggctgaacggaccggtATTCTAACaccggagtaggggTaactctaccgggggttcaaatccccctctctccgcca | 54.0 | 1.63 |
| 21 | SerU-UAGA-"v2" | ggagagatgccggagcggctgaacggaccggaGATTCTAACCccggagtagggAcaactctaccggggttcaaatcccctctctccgcca | 73 | 1.63 |
| 24 | SerU-UAGA-Mag | ggagagatgccggagcggctgaacggaccggtATTCTAACaccggagtaggggcaactctaccgggggttcaaatcccctctctccgcca | 26.0 | 1.63 (a) |

(a) previously described in the literature.

Figure 3

| E. coli tRNA scaffold | Suppressor Name | Suppressor Organism | Suppressor genotype | Codon 5'→3' | Reference |
|---|---|---|---|---|---|
| LeuX* | Su6 | E. coli | A26G + anticodon loop extension | UAGN | 1 |
| GlyU | sufD | S. Typhimurium | anticodon loop extension | GGGG/GGGN | 2, 3 |
| ValT | hopR | S. Typhimurium/E. coli | anticodon loop extension | GUAA/GUAA | 4 |
| GlnU | sufG | E. coli | anticodon loop extension | CAAA | 5 |
| LysQ | -engineered- | E. coli | anticodon loop extension | CAAA | 5 |
| ProL* | SufB | S. Typhimurium | G→A + anticodon loop extension | CCCC | 6 |
| ThrT | SufJ | S. Typhimurium | anticodon loop extension | ACCN | 7 |
| SerU | -engineered- | E. coli | Various (library approach) | Various, including UAGA, AGGG | 8 |

1. Moore, Barry, et. Al. (2000). Journal of Molecular Biology 298 (2): 195–209.
2. Riddle, D. L. & J. Carbon. (1973) Nature: New Biology 242 (121): 230–34.
3. Yourno, J., & S. Tanemura. (1970) Nature 225 (5231): 422–26.
4. O'Connor, M., et al., (1989) The EMBO Journal 8 (13): 4315–23.
5. O'Connor, Michael. (2002) Nucleic Acids Research 30 (9): 1985–90.
6. Sroga, Grazyna E., et al., (1992) Nucleic Acids Research 20 (13): 3463–69.
7. Bossi, L. & D. M. Smith. (1984) PNAS USA 81 (19): 6105–9.
8. Magliery, Thomas J., et al., (2001) Journal of Molecular Biology 307 (3): 755–69.

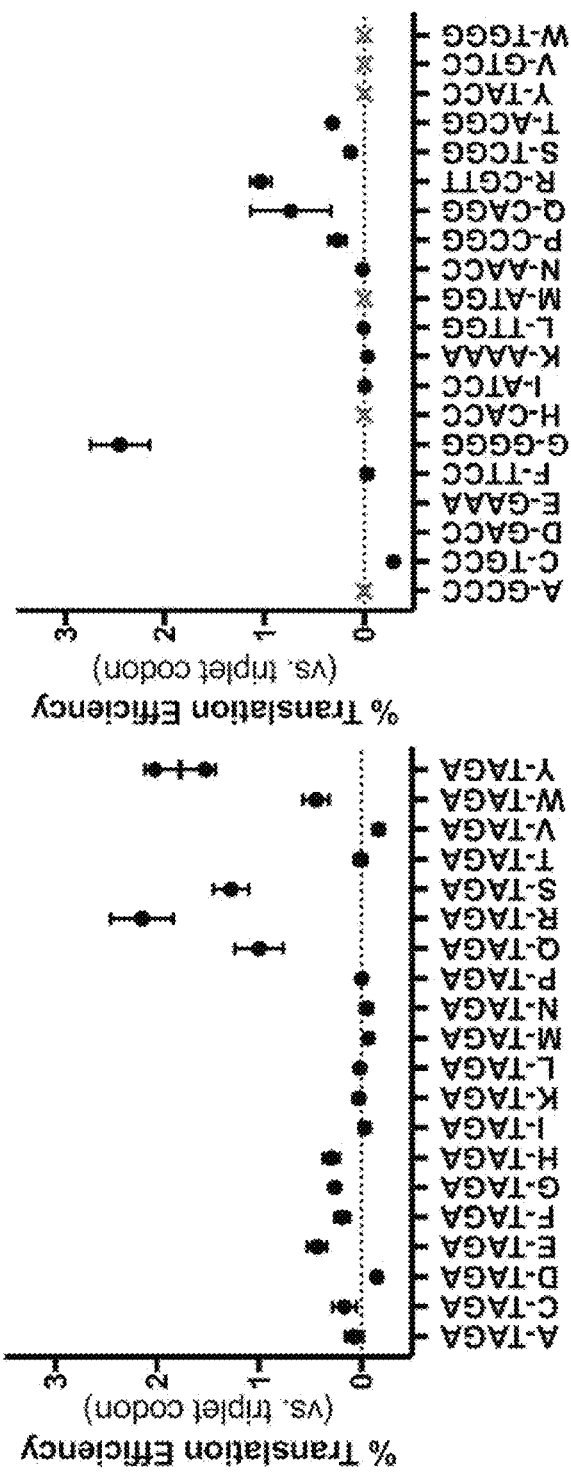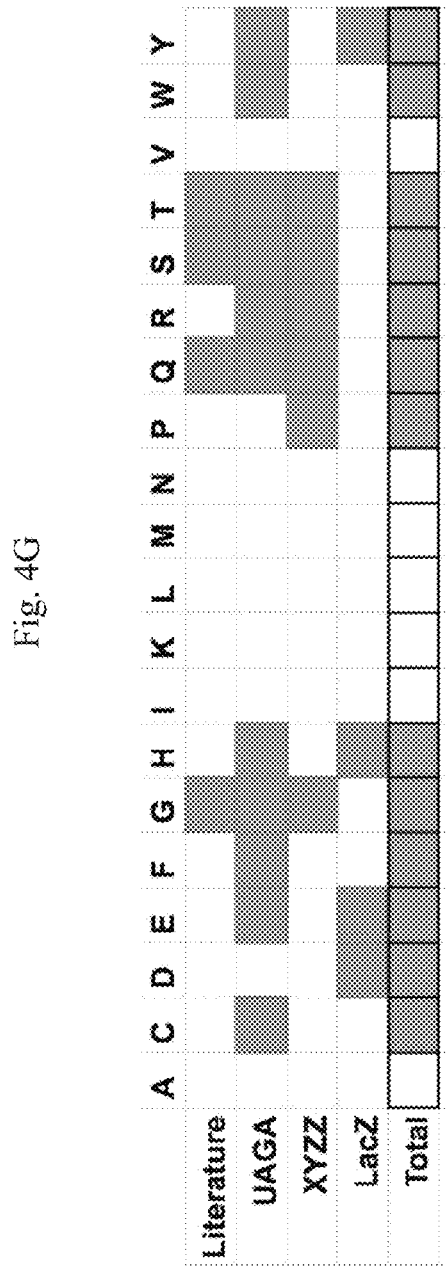
Fig. 4E
Fig. 4F
Fig. 4G

* No cell growth upon tRNA induction - extremely toxic

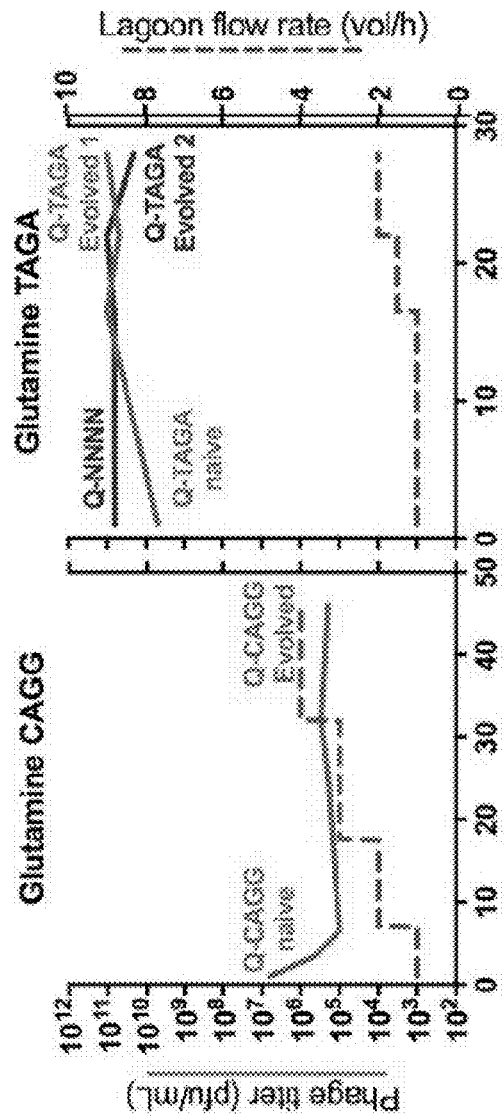
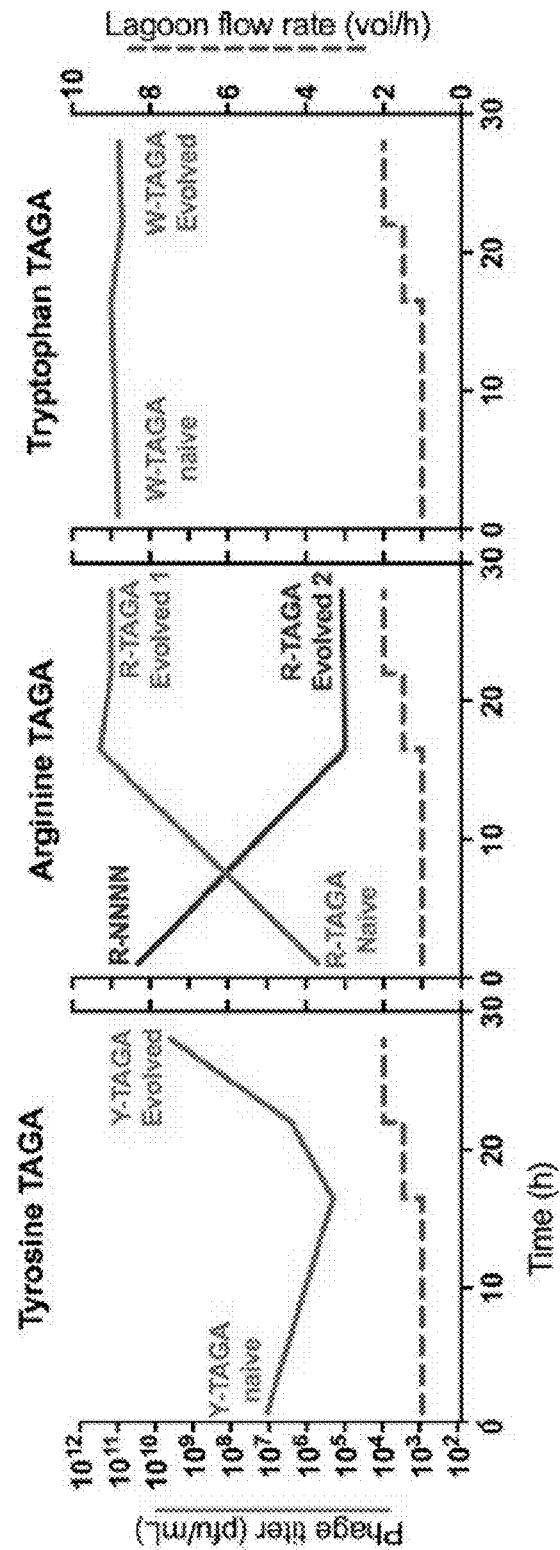
Fig. 6A

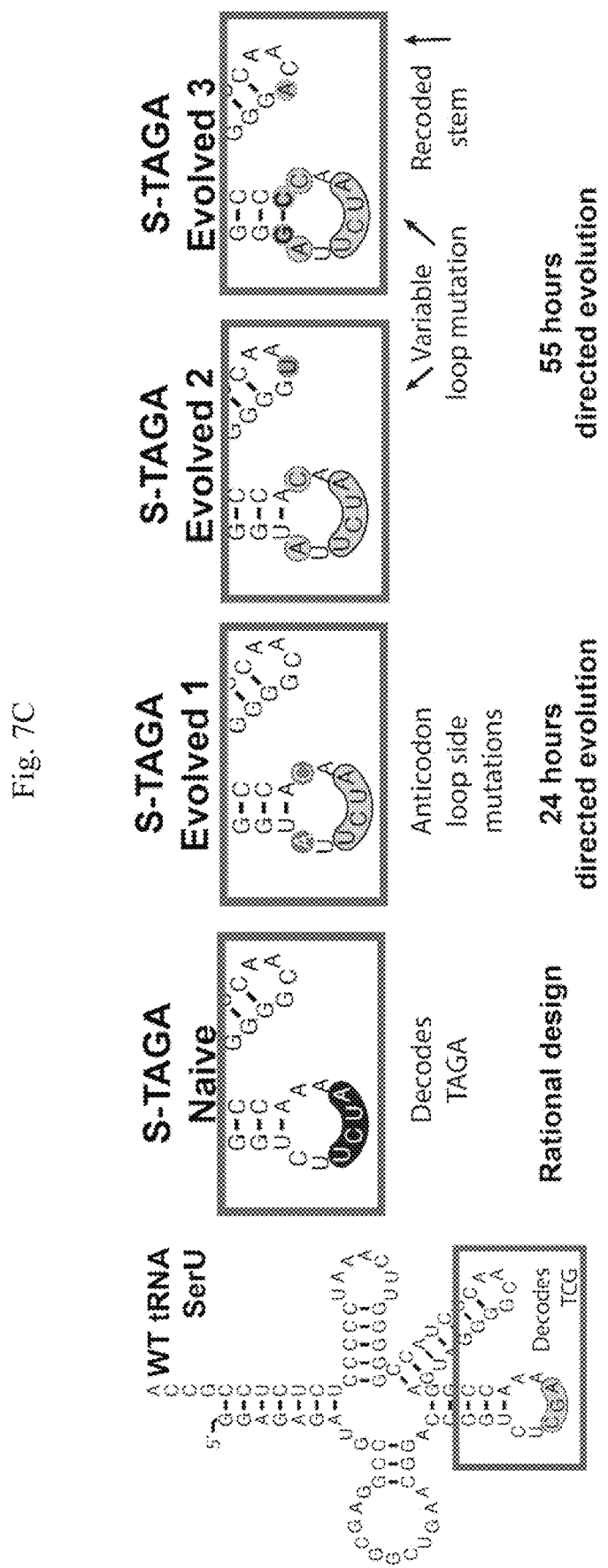

Fig. 9A

| SEQ ID NO | Name | Sequence encoding suppressor (mutations capitalized) | Summary | % of WT function (higher is better) |
|---|---|---|---|---|
| 28 | I-AGGG | aggcttgtagtcaggtggttagagcgcacccctCCCTaaggtgaggtcgagtgttcaagtccactcaggcctacca | Minimally functional | 0.07 |
| 29 | C-CGGT | ggcgcgttaacaaagcggttatgtagcggattACCGaatccgtagtccgattcgactccggaacgcgcctcca | Minimally functional | 0.08 |
| 30 | M-ATGG | cgcggggtggagcagcctggtagctcgtcgggctCCATaacccggaaggtcgtcggttcaaatccggcccccgcaaccga | Minimally functional | 0.09 |
| 31 | M3-AGGG | ggccccttagtcagtggttagagcaggcgactCCCTaatcgcttgtgcgctggttcaagtccagcagggccacca | Minimally functional | 0.09 |
| 32 | D-AGGG | ggagcggtagttcagtcggttagaataacctgcctCCCTacgcaggggggtcgcggttcgagtccgtccgttccgccacca | Minimally functional | 0.10 |
| 33 | F-TACA | gcccggatagctcagtcggtagagcaggggattTGTAaatcccccgtgtcctggttcgattcgattcgagtccgggccacca | Minimally functional | 0.10 |
| 34 | F-CGGT | gcccggataAGCTCAGTCGGTagagcaggggattACCCaatcccccgtgtcctcttggttcgattcgagtccggggcacca | Minimally functional | 0.10 |
| 35 | H-TACA | gtggctatagctcagtcagtcggttagagccctggattTGTAaatccagttgtcgtggttcgaatccaattagccaccca | Minimally functional | 0.11 |
| 36 | Y-TACA | ggttgggtcccgagcggccaaagggagcagactTGTAaatcgcctgctcacagacttcgaaggttcgaatccttcccccaccca | Minimally functional | 0.15 |
| 37 | N-AGGA | tcctctgtagtcagtcggtagaacgcgcggactTCCTaatccgtatgtcactgttcgatccgagtcagtcagagaggcca | Minimally functional | 0.17 |
| 38 | D-CGGC | ggagcggtagttcagtcggttagaatactgcctGCCGacgcaggggtcgcggttcgagtcccgtccgttccgcca | Minimally functional | 0.23 |
| 39 | S-TACA | ggagagatgccgagcggctgaagcggaccggtctTGTAaaaccggagtagggggcaactctaccgggggttcaaatcccctctccgcca | Minimally functional | 0.24 |
| 40 | R-AGGT | gcatcccgtagtcagtcggatagagtactcggctACCTaaccgagcggttggagttcgaatcctccggatgccacca | Minimally functional | 0.33 |
| 41 | W-GGGT | aggggcgtagtcaattggtagagcaccggtctACCCaaaccgggtgtgggagttcgagttcgagtcctccgccctgcca | Minimally functional | 0.38 |

Fig. 9A continued

| | | | |
|---|---|---|---|
| 42 | Y-CAGG | ggtggggttcccgagcggcaaaggaggagcagactCCTGaatctgccgtcacagacttcgaaggttcgaatcgttcccca ccacca | Functional | 0.10 |
| 43 | A-CAGG | ttggtacgtaaaccatcgtgggctatagctcagctgggagagcgcttgcatCCTGatgcaaagagtcagcggttcgatc ccgcttagctccaacaaattccaaccctcgctgca | Functional | 0.13 |
| 44 | T-AGGG | gccgatatagctcagttggtagagcagcggcattCCCTaatcgcaaggtcgtagttcgactcctattatcggcacca | Functional | 0.22 |
| 45 | V-CGGC | gcgtccgtagctcagttggttagagcaccacctttGCCGatcgtgaggtcggtgttcgagtcgcactcggacgcacca | Functional | 0.27 |
| 46 | A-AGGG | ttggtacgtaaacgcatcgtgggctatagctcagctgggagagcgcttgcatCCCTatgcaaagagtcagcggttcgatc ccgcttagctccaacaaattccaaccctcgctgca | Functional | 0.32 |
| 47 | V-CGGT | gccgtccgtagctcagttggttagagcaccacctaACCGatggtgaggtcggtgttcgagtcgcactcggacgcacca | Functional | 0.32 |
| 48 | K-AGAA | gcaaggggtcgtagctcagttggtagagcagttgactTTCTaatcaattggtcgcaggttcgaatctgcacgaccacca atgtaaaaagcgcctaaaggcgcttttt | Functional | 0.35 |
| 49 | V-AGGA | ggatccgtagctcagttggttagagcaccaccttTCCTatggtgaggtcggttcgagtcgcactcggacgcacca | Functional | 0.36 |
| 50 | L-AGGG | gccgaagtgctcagtgggttagagcgtagacgcggtgattCCCTaatcaaccgtagaaatacgtccgttcgagtccggccttcg gcacca | Functional | 0.41 |
| 51 | H-AGGT | gtggctatagctcagttggtagagccctgattACCTatttccagttgtcgtaggttcgaatccattagccacccca | Functional | 0.62 |
| 52 | E-AGGG | gtcccccttcgtctagaggcccaggacaccgcccctCCCTacggcgggtaacaggggttcgaatccccttagggggacgcca | Functional | 0.72 |
| 53 | C-CGGC | ctgaaaggcctgtagctcaatttggcagagcaacaaagcggttattagcggttGCCGaatcgtctagttcgggttcgactcg gaaccgcctccacttcttccgagccggat | Functional | 0.90 |
| 54 | M-AGGG | cgcggggtagagcctcagtggttagagcctggggctCCCTaaccgaaggtcgtcgttcaaatccggccccccgcaacca | Functional | 0.98 |
| 55 | I-AGGA | aggcttgtagctcagttggttagagcgcaccccttTCCTaaggtgaaggtcggtagttcaagtccactcaggcctacca | Functional | 1.07 |
| 56 | G-AGGG | gcgggcgtagttcaatggtagaacgacgagagcttCCCTaagctctatacgaggggttcgattccccttcgcccgctcca | Functional | 1.23 |
| 57 | L-AGGA | gccgaagtggcgaaatcggtagacgcagttgattTCCTaatcaaccgtagaaatacgtccgggttcgagtccggccttcgg cacca | Functional | 1.76 |

Fig. 9A continued

| | | | | |
|---|---|---|---|---|
| 58 | R-AGGG | gcatccgtagttcagctggatagagtactcggctCCCTaaccgagcggtcggaggttcgaatctcccggatgcacca | Functional | 1.81 |
| 59 | F-CGGC | gcccggatagctcagtcggtagagcagggattGCCgaatcccgtgtccttggttcgattcgagtccgggcacca | Functional | |
| 60 | M2-AGGG | ggctacgtagctcagttggttagagcacatcactCCCTaatgatgggtcacagttcgaatcccgtcgtagcacca | Functional | 2.67 |
| 61 | E-AGGA | gtcccttcgtgtagaggcccaggacaccgccctTCCTacggcggtaacagggttcgaatccctgtagggacgcca | Functional | 3.07 |
| 62 | E-CGGT | gtcccctcgtctagaggcccaggacaccgccctACCGacgcggtaacagggttcgaatccctaggggacgcca | Functional | 3.82 |
| 63 | W-AGGG | aggggcgtagttcaattgtagagcaccggtctCCCTaaaccggttgttggagttcgagtcctccgccctgcca | Functional | 4.27 |
| 64 | R-CGGT | gcatccgtagTtcagctggatagagtactcggctACCGaaccgagcggtcggaggttcgaatctcccggatgcacca | Functional | 4.41 |
| 65 | H-AGGG | gtggctatagctcagttggttagagccctggattCCCTattccagttgtcgtggttcgaatccattagccaccca | Functional | 6.23 |
| 66 | S-AGGG | ggagagatgccggagctggcctgaacggaccggtctCCCTaaaccggagtaggggcaactctaccggggttcaaatccc cctctctccgcca | Functional | 6.94 |
| 67 | S-CGGC | ggagagatgccggagctggcctgaacggaccgtctGCCCaaaccggagtaggggcaactctaccggggttcaaatccc cctctctccgcca | Functional | 14.90 |

Fig. 9B

| SEQ ID NO | Name | Sequence encoding suppressor (mutations capitalized) | Summary | % of WT function (higher is better) |
|---|---|---|---|---|
| 68 | A-GGGT | ttggtacgtaaacgcatcgtgggctatagctcagctcgggagagcgttgcatACCCatgcaagaggtcagcggttcgatcccgcttagctccaccaaatttccaaccctcgctgca | Extremely toxic | X |
| 69 | H-CAGT | gtggctatagctcagttggtagagcccctggattACTGatccagttgtcgtgggttcgaatccattagcaccca | Extremely toxic | X |
| 70 | A-GGGG | ttggtacgtaaacgcatcgtgtgggctatagctcagctcgggagagcgttgcatCCCCatgcaagaggtcagcggttcgatcccgcttagctccaccaaattccaaccctcgctgca | Extremely toxic | X |
| 71 | W-GGGG | agggcgtagttcaattgtagacgcaccggtctCCCCaaaccggtgttggagttcgagtctctccgccctgcca | Extremely toxic | X |
| 72 | L-CGGT | gccgaagtggcgaaatcggtagacgcagtgattACCGaatcaaccgtagaaatacgtgccggttcgagtccggccttcggcacca | Extremely toxic | X |
| 73 | D-GGAC | gggagccgtagttcagtcggttagaataccgcctGTCCacgcagggggtcgcgggttcgagtccgtccgttccgcca | Nonfunctional | -0.66 |
| 74 | N-AAAT | tcctctgtagttcagtcggtagaacggcggactATTTaatccgtatgtcactgttcgagtcagtcagtcagaggagcca | Nonfunctional | -0.11 |
| 75 | M3-TAGA | ggcccttagctcagttggtagagcaggcgactTCTAaatcgcttggtcgctgttcaagtccagcaggggccacca | Nonfunctional | -0.10 |
| 76 | S-GCAT | ggagagatgccggagcggctgaacggcggcggtctATGCaaaccggagtaggggcaactcaccggggttcaaatcccctctctccgcca | Nonfunctional | -0.10 |
| 77 | N-CGGT | tcctctgtagttcagtcggtagaacggcggactACCGaatccgtatgtcacgttcgagtccagtcagaggagcca | Nonfunctional | -0.07 |
| 78 | N-CAGG | tcctctgtagttcagtcggtagaacggcggactCCTGaatccgtatgtcactgttcgagtccagtcagaggagcca | Nonfunctional | -0.06 |
| 79 | N-AATT | tcctctgtagttcagtcggtagaacggcggactAATTaatccgtatgtcactgttcgagtccagtcagaggagcca | Nonfunctional | -0.06 |
| 80 | M2-TAGA | ggctacgtagtcagtcggttagagcacatcactTCTAaatgatgggtcacaggttcacagttcgagtccgtagtagccacca | Nonfunctional | -0.05 |
| 81 | N-AACC | tcctctgtagttcagtcggtagaacggcggactGGTTaatccgtatgtcactgttcgagtccagtcagaggagcca | Nonfunctional | -0.05 |
| 82 | N-AGGG | tcctctgtagttcagtcggtagaacggcggactCCCTaatccgtatgtcactgttcgagtccagtcagaggagcca | Nonfunctional | -0.03 |

Fig. 9B continued

| | | | | |
|---|---|---|---|---|
| 83 | D-AGGC | ggagcggtagttcagtcggttagaataccgctGCCtacgcaggggtcgcgggtcgagtcccgtccgttccgcca | Nonfunctional | -0.01 |
| 84 | N-TACA | tcctctgtagttcagtcggtagaacggcggactTGTAaatccgtatgtcactgttcgagtccagtcagaaggagcca | Nonfunctional | 0.00 |
| 85 | M2-ATGG | ggctacgtagctcagttggttagagcacatcactCCAtaatgatgggtcacagttcgaatccgtcgtagccacca | Nonfunctional | 0.00 |
| 86 | M3-ATGG | ggccccttagctcagtcggttagagcaggcgactCCAtaatcgctggtcgtgttcaagtccagcaggggccacca | Nonfunctional | 0.00 |
| 87 | M-TAGA | cgcgggggtgggagcctggtagctcgtcgggctTCTAaacccgaaggtcgtcggttcaaatccggcccccgcaacca | Nonfunctional | 0.01 |

Evolved tRNAs Below

| SEQ ID NO | Name | Sequence encoding suppressor (mutations capitalized) | % of WT function | % WT function if un-evolved |
|---|---|---|---|---|
| 88 | R-TAGA-opt2 | gcatccgtagTtcagtcgtatagagCactcggctTCTAaaccgaTcggtcggaggttcgaatcctcccgatgcacca | 9.48 | 2.85 |
| 89 | W-TAGA-opt1 | aggggcgtagttcaattggtagaAcaccggtctTCTAaTaccgggtgttggagttcgagtctccgcccCgcca | 41.7 | 0.45 |
| 90 | S-TCGG-Evo1 | ggagagatgccgagccggtcgaacggaccggtAtCCGAaCaccggagtagggcaactctaccggggttcaaatcccctctctccgcca | 13.17 | N/A |
| 91 | E-TAGA-Evo1 | gtccccttcgtctagagggccaggacaccgcccfTCTAaTggccggtaacagggagttcgaatccctaggggacgcca | 2.72 | N/A |
| 92 | F-TAGA-Evo1 | gcccggatagtcagtcggtagagcaggggaCtTCTAaTtcccgtcctttgattccgagtccgggcacca | 22.15 | N/A |
| 93 | F-TAGA-Evo2 | gcccggatagctcagtcggtagcagggaAtTCTAGCtccccgtcttggttccgagtccgggcacca | 22.31 | N/A |
| 94 | F-TAGA-Evo3 | gcccggatagctcagtcggtagcagggaGtTCTAGTtcccgtttccttgattccgagtccgggcacca | 13.78 | N/A |
| 95 | G-TAGA-Evo1 | gcgggcgtagttcaatggtagaacgagagcCtTCTAGTgctctatacgagggttcgattccttcgccgctcca | 2.75 | N/A |

Fig. 9B continued

| | | | |
|---|---|---|---|
| 96 | H-TAGA-Evo1 | gtggctatagctcagttggtagagcccctggaCtTCTAattccagttgtcgtgggttcgaatccattagccacccca | 3.23 | N/A |
| 97 | H-TAGA-Evo2 | gtggctatagctcagttggtagagcccctggaGtTCTAattccagttgtcgtgggttcgaatccattagccacccca | 4.77 | N/A |
| 131 | A-AGGG T.AG | ggggctatagctcagtgggagagcgcttgcTtCCCTAGgcaagagagtcagcggttcgatccgcttagctccacca | 15.57 | N/A |
| 132 | S-AGGG C.AT | ggagagatgccggacgcgagccggtctgaacgaccggtctCCCTaTaccggagtaggggcaactctaccggggttcaaatcccc ctctctccgcca | 37.28 | N/A |
| 133 | G-AGGG C.AT | gcggggcgtagttcaatggtagaaacgtagagcCtCCCTaTgctctatacgagggttcgattccttgccccgctca | 29.42 | N/A |
| 134 | D-CGGC G.AA | ggagcgcgtagttcagtcggttagaatacctgcGtCCCTaAgcaggggggtcgcgggttcgagtccgtcgttccgcca | 20.92 | N/A |
| 135 | F-CGGC G.AT | gcccggatagctcagtcggtagagcaggggaGtGCCGaTtccccgtcttgttcgattccgagtccgggcacca | 1.15 | N/A |
| 136 | R-CGGC G.AA | gcatcgtagtcagtcggatagagtactcggGtGCCGaaccgagcggtcgaagggttcgaatcctccgatgcacca | 8.70 | N/A |
| 137 | H-TACA G.AT | gtgggctatagctcagttggtagagcccctggaGtTGTAattccagttgtcgtgggttcgaatccattagccaccca | 0.48 | N/A |
| 138 | S-TACA A.AA | ggagagatgccggagcggctgaacgaccggtAtTGTAaaacggagtaggggcaactctaccggggttcaaatcccc ctctctccgcca | 0.28 | N/A |
| 139 | F-TAGA A..aa | gcccggatagctcagtcggtagagcagggggaAtTCTAaatccccgtcttggttcgattccgagtccgggcacca | 0.86 | N/A |
| 140 | F-TAGA A..aa C24T | gcccggatagctcagtcggtagagcagggggaAtTCTAaatccTcgtcttccttggttcgattccgagtccgggcacca | 1.28 | N/A |
| 141 | H-TAGA Δ45 | gtggctatagctcagttggtagagcccctggattTCTAattccagtcgtgtgggttcgaatccgttgccaccca | 1.40 | N/A |
| 142 | H-TAGA C..at Δ45 | gtgggctatagctcagttggtagagcccctggaCtTCTAattccagttgctgggtcgaatccattagccaccca | 1.85 | N/A |
| 143 | H-TAGA C..at Δ48 | gtgggctatagctcagttggtagagcccctggaCtTCTAattccagttgtgtgggttcgaatccattagccaccca | 1.67 | N/A |

Fig. 9B continued

| | | | | |
|---|---|---|---|---|
| 144 | S-TAGA c..aT | ggagagatgccggagcggctgaacggaccggtctTCTAaTaccggagtaggggcaactctaccggggggttcaaatccccc ctctctccgcca | 2.94 | N/A |
| 145 | S-TAGA C40T | ggagagatgccggagcggctgaacggaccggtctTCTAaaaTcggagtaggggcaactctaccggggggttcaaatccccc ctctctccgcca | 1.28 | N/A |

Fig. 9C

| SEQ ID NO | Name | Plasmid | SEQ ID NO | Name | Plasmid |
|---|---|---|---|---|---|
| 1 | C-TAGA | pED14xC-1 | 43 | A-CAGG | pED14xA-5 |
| 2 | E-TAGA | pED14xE-1 | 44 | T-AGGG | pED14xT-3 |
| 3 | F-TAGA | pED14xF-1 | 45 | V-CGGC | pED14xV-5 |
| 4 | G-TAGA | pED14xG-1 | 46 | A-AGGG | pED14xA-3 |
| 5 | H-TAGA | pED14xH-1 | 47 | V-CGGT | pED14xV-4 |
| 6 | Q-TAGA | pED14xQ-1 | 48 | K-AGAA | pED14xK-3 |
| 7 | R-TAGA | pED14xR-1 | 49 | V-AGGA | pED14xV-3 |
| 8 | S-TAGA | pED14xS-1 | 50 | L-AGGG | pED14xL-5 |
| 9 | W-TAGA | pED14xW-1 | 51 | H-AGGT | pED14xH-4 |
| 10 | Y-TAGA | pED14xY-1 | 52 | E-AGGG | pED14xE-3 |
| 11 | P-CCGG | pED14xP-2 | 53 | C-CGGC | pED14xC-3 |
| 12 | Q-CAGG | pED14xQ-2 | 54 | M-AGGG | pED14xM-4 |
| 13 | R-CGTT | pED14xR-2 | 55 | I-AGGA | pED14xI-3 |
| 14 | S-TCGG | pED14xS-2 | 56 | G-AGGG | pED14xG-3 |
| 15 | T-ACGG | pED14xT-2 | 57 | L-AGGA | pED14xL-3 |
| 16 | Y-UAGA-opt1 | pED14xY-3 | 58 | R-AGGG | pED14xR-5 |
| 17 | R-UAGA-opt1 | pED14xR-3 | 59 | F-CGGC | pED14xF-4 |
| 18 | Q-UAGA-opt1 | pED14xQ-3 | 60 | M2-AGGG | pED14xM2-3 |
| 19 | Q-UAGA-opt2 | pED14xQ-4 | 61 | E-AGGA | pED14xE-4 |
| 20 | SerU-UAGA- "v1" | pED14xS-3 | 62 | E-CGGT | pED14xE-5 |
| 21 | SerU-UAGA-"v2" | pED14xS-4 | 63 | W-AGGG | pED14xW-4 |
| 22 | G-GGGG | pED14xG-2 | 64 | R-CGGT | pED14xR-7 |
| 23 | T-ACCA | pED3xT1 | 65 | H-AGGG | pED14xH-3 |
| 24 | SerU-UAGA-Mag | pED3xS1 | 66 | S-AGGG | pED14xS-5 |
| 28 | I-AGGG | pED14xI-4 | 67 | S-CGGC | pED14xS-7 |
| 29 | C-CGGT | pED14xC-4 | 68 | A-GGGT | pED14xA-4 |
| 30 | M-ATGG | pED14xM-2 | 69 | H-CAGT | pED14xH-6 |
| 31 | M3-AGGG | pED14xM3-3 | 70 | A-GGGG | pED14xA-6 |
| 32 | D-AGGG | pED14xD-3 | 71 | W-GGGG | pED14xW-6 |
| 33 | F-TACA | pED14xF-3 | 72 | L-CGGT | pED14xL-4 |
| 34 | F-CGGT | pED14xF-6 | 73 | D-GGAC | pED14xD-6 |
| 35 | H-TACA | pED14xH-5 | 74 | N-AAAT | pED14xN-9 |
| 36 | Y-TACA | pED14xY-4 | 75 | M3-TAGA | pED14xM3-1 |
| 37 | N-AGGA | pED14xN-4 | 76 | S-GCAT | pED14xS-6 |
| 38 | D-CGGC | pED14xD-5 | 77 | N-CGGT | pED14xN-5 |
| 39 | S-TACA | pED14xS-8 | 78 | N-CAGG | pED14xN-7 |
| 40 | R-AGGT | pED14xR-6 | 79 | N-AATT | pED14xN-8 |
| 41 | W-GGGT | pED14xW-5 | 80 | M2-TAGA | pED14xM2-1 |
| 42 | Y-CAGG | pED14xY-5 | | | |

Fig. 9C continued

| SEQ ID NO | Name | Plasmid | SEQ ID NO | Name | Plasmid |
|---|---|---|---|---|---|
| 81 | N-AACC | pED14xN-10 | 131 | A-AGGG T.AG | pED14xA-opt3.a1 |
| 82 | N-AGGG | pED14xN-3 | 132 | S-AGGG C.AT | pED14xS-opt3.a1 |
| 83 | D-AGGC | pED14xD-4 | 133 | G-AGGG C.AT | pED14xG-opt3.a2 |
| 84 | N-TACA | pED14xN-6 | 134 | D-CGGC G.AA | pED14xD-opt4.a1 |
| 85 | M2-ATGG | pED14xM2-2 | 135 | F-CGGC G.AT | pED14xF-opt4.a1 |
| 86 | M3-ATGG | pED14xM3-2 | 136 | R-CGGC G.AA | pED14xR-opt4.a1 |
| 87 | M-TAGA | pED14xM-1 | 137 | H-TACA G.AT | pED14xH-opt5.a1 |
| 88 | R-TAGA-opt2 | pED14xR-4 | 138 | S-TACA A.AA | pED14xS-opt5.a1 |
| 89 | W-TAGA-opt1 | pED14xW-3 | 139 | F-TAGA A..aa | pED14f6-F |
| 90 | S-TCGG-Evo1 | pED14xS-opt1 | 140 | F-TAGA A..aa C2 | pED14f7-F |
| 91 | E-TAGA-Evo1 | pED14xE-opt1 | 141 | H-TAGA Δ45 | pED14f1-H |
| 92 | F-TAGA-Evo1 | pED14xF-opt1 | 142 | H-TAGA C..at Δ45 | pED14f4-H |
| 93 | F-TAGA-Evo2 | pED14xF-opt2 | 143 | H-TAGA C..at Δ48 | pED14f5-H |
| 94 | F-TAGA-Evo3 | pED14xF-opt3 | 144 | S-TAGA c..aT | pED14f2-S |
| 95 | G-TAGA-Evo1 | pED14xG-opt1-TAGA | 145 | S-TAGA C40T | pED14f3-S |
| 96 | H-TAGA-Evo1 | pED14xH-opt1 | | | |
| 97 | H-TAGA-Evo2 | pED14xH-opt2 | | | |

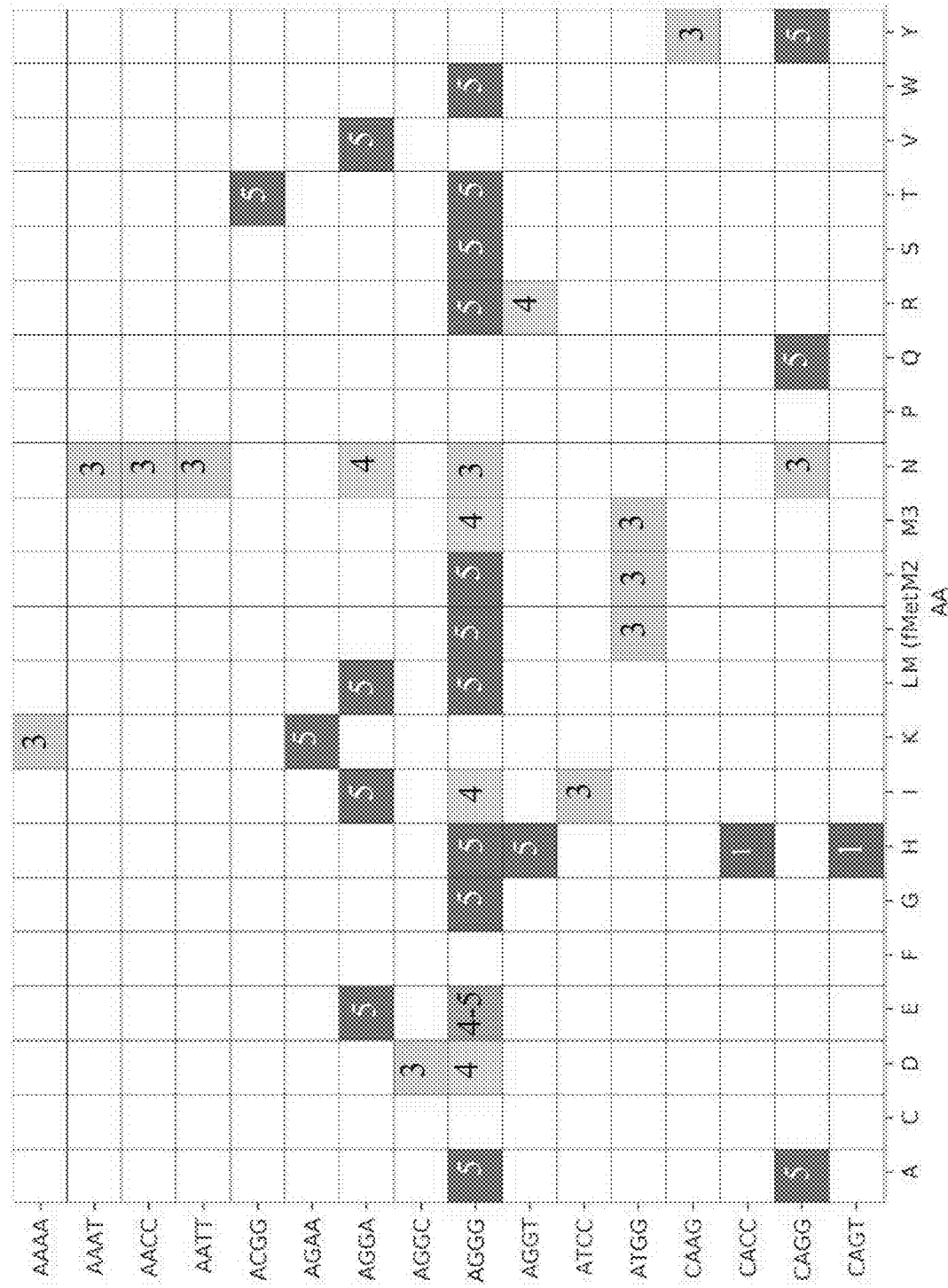

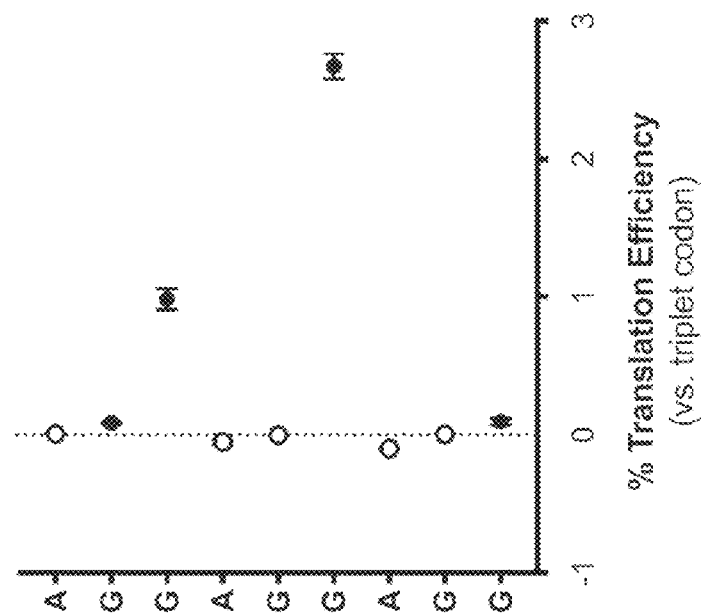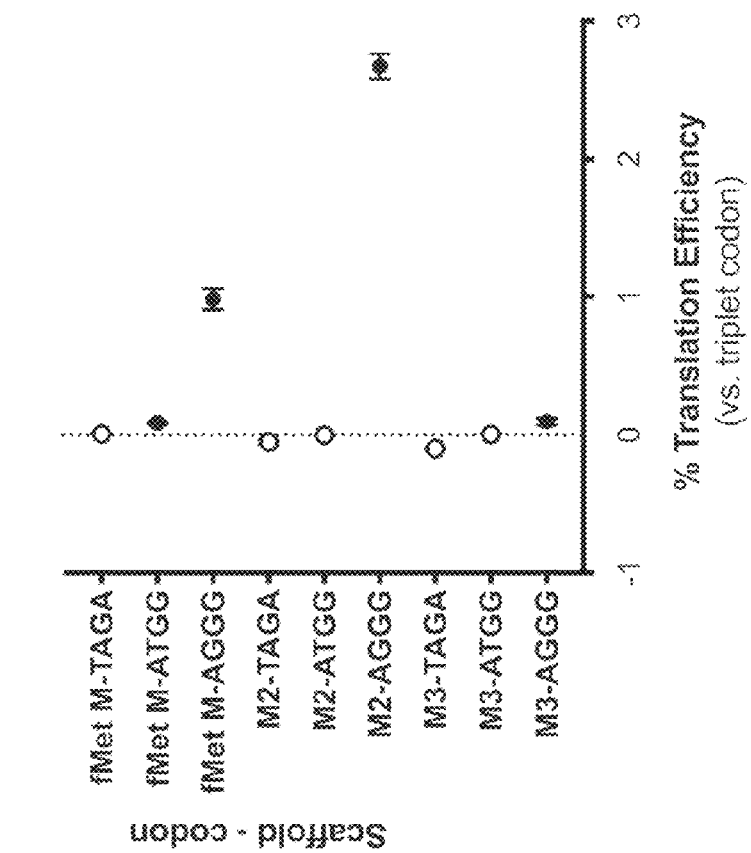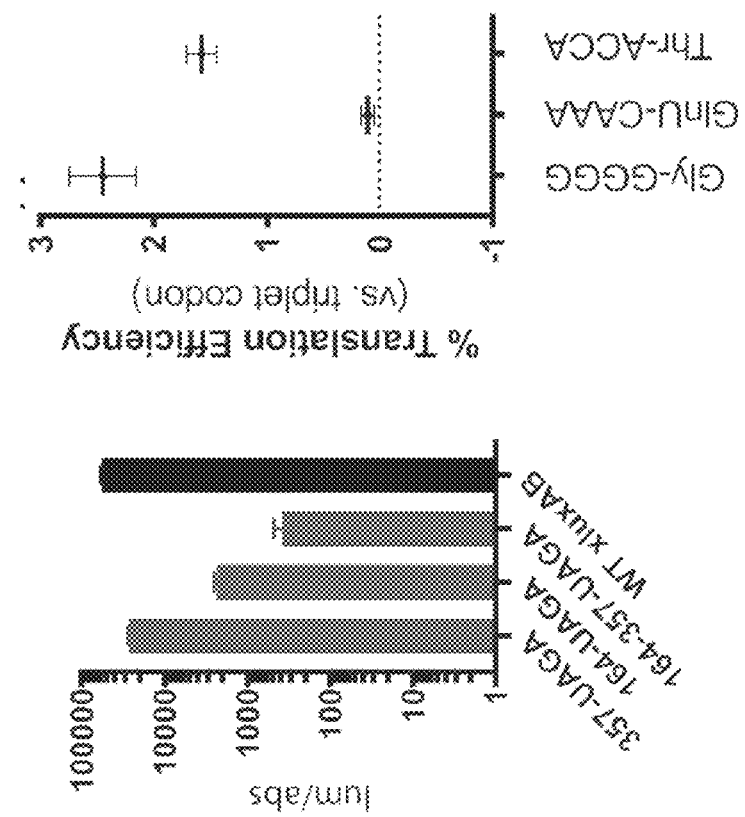

pIII reporter     tRNA library encoded on phage     plaques are hits

| | AGGG | CGTT | GGGG | CCGG | CAGG | TCGG | ACGG | CGGT |
|---|---|---|---|---|---|---|---|---|
| A | ACGG | | | | | | | CGGA CGGC |
| C | | mismatched | | | | mismatched | mismatched | |
| D | AGGG AGGA | TACA | | TACA | CAGG | TACA | TACA | CGGT CGGC |
| E | AGGG | | GGGT | TACA | CAGT | | | |
| F | AGGG AGGT | | | TACA | | | | |
| G | AGGA | | | | | | | |
| H | AGGG AGGT | | | | CAGG | mismatched | mismatched | |
| I | AGGA | | | | | | | |
| K | AGAA | | | | | | | |
| L | AGGA | | | | CAGG | | | CGGT |
| M2 | | | | | | | | CGGT |
| M3 | | | | | | | | |
| N | | | | | | | | |
| P | | | | | CAGG | | | |
| Q | | | | | | | | mismatch CGGT CGGC |
| R | AGGG AGGT | | TACA GCAT | GCAT | | mismatched GCAT | GCAT | |
| S | AGGG | TACA | GGGT | CCGG | CAGG | TACA | GCAT | CGGT CGGC |
| T | AGGA | | TACA | | | | | |
| V | AGGA | | | | | | | |
| W | AGGG | | | | | | | |
| Y | TACA | TACA | | | CAGG | TACA | TACA | TACA |

Repeated application of pIII reporter results in continuous directed evolution

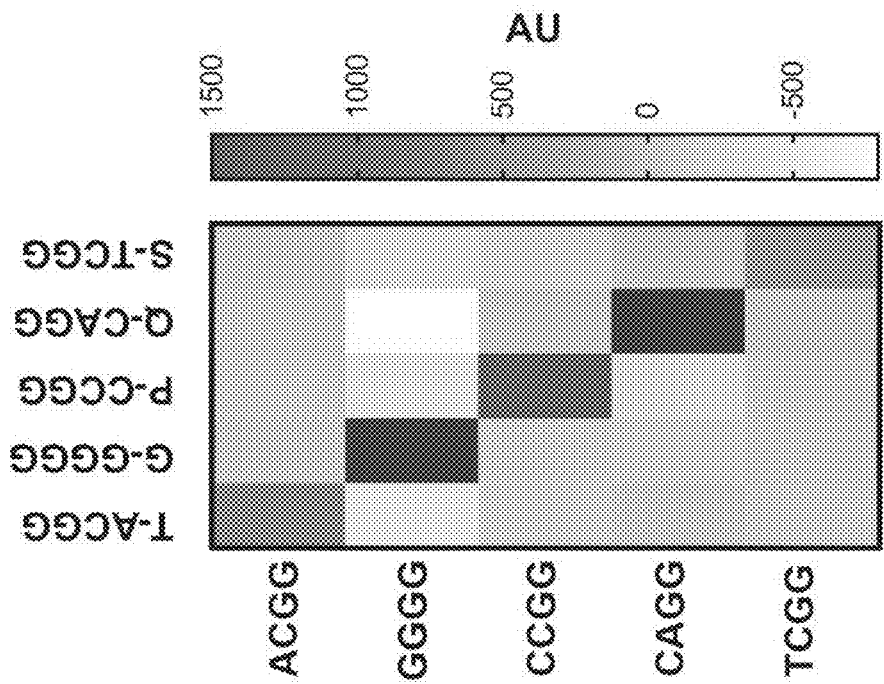
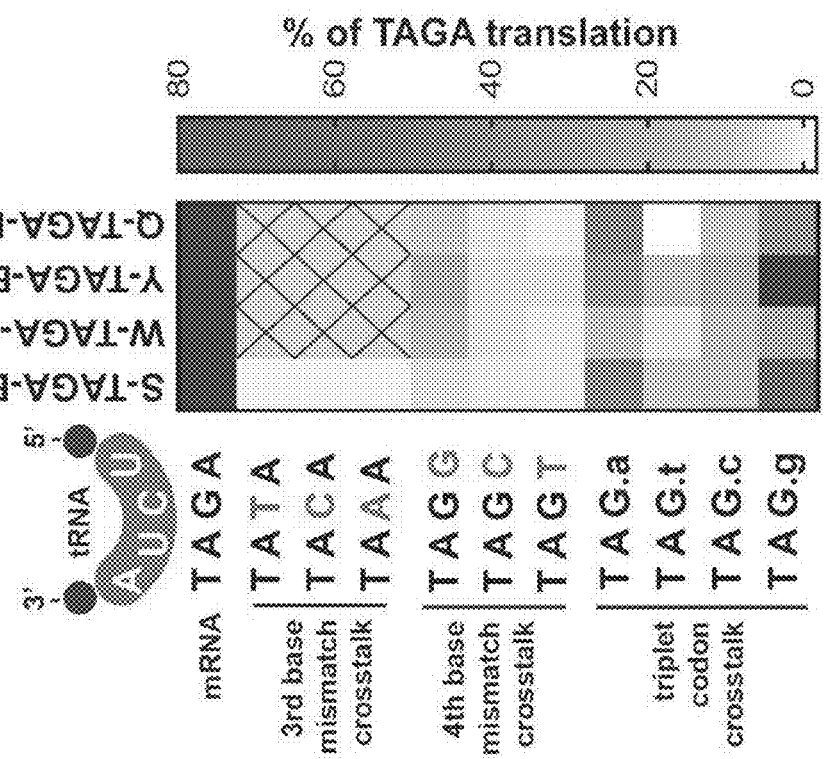

SEQUENCE LISTING

<160> NUMBER OF SEQ ID NOS: 145

<210> SEQ ID NO 1
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 1
ggcgcgttaa caaagcggtt atgtagcgga tttctaaatc cgtctagtcc ggttcgactc    60
cggaacgcgc ctcca    75

<210> SEQ ID NO 2
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 2
gtccccttcg tctagaggcc caggacaccg cccttctaac ggcggtaaca ggggttcgaa    60
tcccctaggg gacgcca    77

<210> SEQ ID NO 3
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 3
gcccggatag ctcagtcggt agagcagggg atttctaaat ccccgtgtcc ttggttcgat    60
tccgagtccg ggcacca    77

<210> SEQ ID NO 4

```
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 4
gcgggcgtag ttcaatggta gaacgagagc tttctaaagc tctatacgag ggttcgattc    60
ccttcgcccg ctcca                                                    75

<210> SEQ ID NO 5
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 5
gtggctatag ctcagttggt agagccctgg atttctaatt ccagttgtcg tgggttcgaa    60
tcccattagc caccca                                                   77

<210> SEQ ID NO 6
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 6
tggggtatcg ccaagcggta aggcaccgga tttctaattc cggcattccg aggttcgaat    60
cctcgtaccc cagcca                                                   76

<210> SEQ ID NO 7
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 7
gcatccgtag ttcagctgga tagagtactc ggcttctaaa ccgagcggtc ggaggttcga    60
atcctcccgg atgcacca                                                 78

<210> SEQ ID NO 8
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 8
ggagagatgc cggagcggct gaacggaccg gtcttctaaa accggagtag gggcaactct    60
accgggggtt caaatccccc tctctccgcc a                                  91

<210> SEQ ID NO 9
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 9
aggggcgtag ttcaattggt agagcaccgg tcttctaaaa ccgggtgttg ggagttcgag    60
```

```
tctctccgcc cctgcca                                                  77

<210> SEQ ID NO 10
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 10
ggtggggttc ccgagcggcc aaagggagca gacttctaaa tctgccgtca cagacttcga   60
aggttcgaat ccttccccca ccacca                                        86

<210> SEQ ID NO 11
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 11
cggtgattgg cgcagcctgg tagcgcactt cgttccggga cgaagggtc ggaggttcga    60 atcctctatc accgacca                                                 78

<210> SEQ ID NO 12
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 12
tggggtatcg ccaagcggta aggcaccgga ttcctgattc cggcattccg aggttcgaat   60
cctcgtaccc cagcca                                                   76

<210> SEQ ID NO 13
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 13
gcatccgtag ctcagctgga tagagtactc ggctaacgaa ccgagcggtc ggaggttcga   60
atcctcccgg atgcacca                                                 78

<210> SEQ ID NO 14
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 14
ggagagatgc cggagcggct gaacggaccg gtctccgaaa accggagtag gggcaactct   60
accgggggtt caaatccccc tctctccgcc a                                  91

<210> SEQ ID NO 15
<211> LENGTH: 77
<212> TYPE: DNA
<213> ORGANISM: Artificial Sequence
<220> FEATURE:
```

<223> OTHER INFORMATION: Synthetic Oligonucleotide

<400> SEQUENCE: 15
gccgatatag ctcagttggt agagcagcgc attccgtaat gcgaaggtcg taggttcgac    60
tcctattatc ggcacca                                                   77

<210> SEQ ID NO 16
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 16
ggtggggttc ccgagcggcc aaagggagca gaactctaaa tctgccgtca cagacttcga    60
aggttcgaat ccttccccca ccacca                                         86

<210> SEQ ID NO 17
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 17
gcatccgtag ctcagctgga tagagtactc ggcttctaaa ccgatcggtc ggaggttcga    60
atcctcccgg atgcacca                                                  78

<210> SEQ ID NO 18
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 18
tggggtatcg ccaagcggta aggcaccgga cttctaattc ggcattccg aggttcgaat     60 cctcgtaccc cagcca                                                    76

<210> SEQ ID NO 19
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 19
tggggtatcg ccaagcggta aggcaccgga cttctaattc ggcatccga ggttcgaatc     60 ctcgtacccc agcca                                                     75

<210> SEQ ID NO 20
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 20
ggagagatgc cggagcggct gaacggaccg gtattctaac accggagtag gggtaactct    60
accgggggtt caaatccccc tctctccgcc a                                   91

```
<210> SEQ ID NO 21
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 21
ggagagatgc cggagcggct gaacggaccg ggattctaac cccggagtag ggacaactct    60
accgggggtt caaatccccc tctctccgcc a                                   91

<210> SEQ ID NO 22
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 22
gcgggcgtag ttcaatggta gaacgagagc ttccccaagc tctatacgag ggttcgattc    60
ccttcgcccg ctcca                                                     75

<210> SEQ ID NO 23
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 23
gctgatatag ctcagttggt agagcgcacc ctttggtaag ggtgaggtcg gcagttcgaa    60
tctgcctatc agcacca                                                   77

<210> SEQ ID NO 24
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 24
ggagagatgc cggagcggct gaacggaccg gtattctaac accggagtag gggcaactct    60
accgggggtt caaatccccc tctctccgcc a                                   91

<210> SEQ ID NO 25
<211> LENGTH: 188
<212> TYPE: DNA
<213> ORGANISM: Artificial Sequence
<220> FEATURE:
<223> OTHER INFORMATION: Synthetic Oligonucleotide

<400> SEQUENCE: 25
tgtgcttctc aaatgcctga ggccagtttg ctcaggctct ccccgtggag gtaataattg    60
acgatatgat cagtgcacgg ctaactaagc ggcctgctga ctttctcgcc gatcaaaagg   120
cattttgcta ttaagggatt gacgagggcg tatctgcgca gtaagataat tgtgagcgga   180
taacaatt                                                            188

<210> SEQ ID NO 26
<211> LENGTH: 2124
<212> TYPE: DNA
<213> ORGANISM: Artificial Sequence
<220> FEATURE:
```

<223> OTHER INFORMATION: Synthetic Oligonucleotide

<400> SEQUENCE: 26

```
atgaaatttg gaaacttttt gcttacatac caacctcccc aattttccca aacagaggta      60
atgaaacgtt tggttaaatt aggtcgcatc tctgaggagt gtggttttga taccgtatgg     120
ttactggagc atcatttcac ggagtttggt ttgcttggta acccttatgt cgctgctgca     180
tatttacttg gcgcgactaa aaaattgaat gtaggaactg ccgctattgt tcttcccaca     240
gcccatccag tacgccaact tgaagatgtg aatttattgg atcaaatgtc aaaaggacga     300
tttcggtttg gtatttgccg agggctttac aacaaggact ttcgcgtatt cggaacagat     360
atgaataaca gtcgcgcctt agcggaatgc tggtacgggc tgataaagaa tggcatgaca     420
gagggatata tggaagctga taatgaacat atcaagttcc ataaggtaaa agtaaacccc     480
gcggcgtata gcagaggtgg cgcaccggtt tatgtggtgg ctgaatcagc ttcgacgact     540
gagtgggctg ctcaatttgg cctaccgatg atattaagtt ggattataaa tactaacgaa     600
aagaaagcac aacttgagct ttataatgaa gtggctcaag aatatgggca cgatattcat     660
aatatcgacc attgcttatc atatataaca tctgtagatc atgactcaat taaagcgaaa     720
gagatttgcc ggaaatttct ggggcattgg tatgattctt atgtgaatgc tacgactatt     780
tttgatgatt cagaccaaac aagaggttat gatttcaata agggcagtg gcgtgacttt     840
gtattaaaag gacataaaga tactaatcgc cgtattgatt acagttacga aatcaatccc     900
gtgggaacgc cgcaggaatg tattgacata attcaaaaag acattgatgc tacaggaata     960
tcaaatattt gttgtggatt tgaagctaat ggaacagtag acgaaattat tgcttccatg    1020
aagctcttcc agtctgatgt catgccattt cttaaagaaa acaacgttc gctattatat    1080
tatggcggtg gcgtagcgg cggtggcggt agcggcggtg gcggtagcgg cggtggcggt    1140
agcaaatttg gattgttctt ccttaacttc atcaattcaa caactgttca agaacagagt    1200
atagttcgca tgcaggaaat aacggagtat gttgataagt tgaattttga acagatttta    1260
gtgtatgaaa tcattttttc agataatggt gttgtcggcg ctcctctgac tgtttctggt    1320
tttctgctcg gtttaacaga gaaaattaaa attggttcat taaatcacat cattacaact    1380
catcatcctg tccgcatagc ggaggaagct tgcttattgg atcagttaag tgaagggaga    1440
tttattttag ggtttagtga ttgcgaaaaa aaagatgaaa tgcattttt taatcgcccg    1500
gttgaatatc aacagcaact atttgaagag tgttatgaaa tcattaacga tgctttaaca    1560
acaggctatt gtaatccaga taacgatttt tatagcttcc ctaaaatatc tgtaaatccc    1620
catgcttata cgccaggcgg acctcggaaa tatgtaacag caaccagtca tcatattgtt    1680
gagtgggcgg ccaaaaaagg tattcctctc atctttaagt gggatgattc taatgatgtt    1740
agatatgaat atgctgaaag atataaagcc gttgcggata aatatgacgt tgacctatca    1800
gagatagacc atcagttaat gatattagtt aactataacg aagatagtaa taaagctaaa    1860
caagagacgc gtgcatttat tagtgattat gttcttgaaa tgcaccctaa tgaaaatttc    1920
gaaaataaac ttgaagaaat aattgcagaa aacgctgtcg gaaattatac ggagtgtata    1980
actgcggcta gttggcaat tgaaaagtgt ggtgcgaaaa gtgtattgct gtcctttgaa    2040
ccaatgaatg atttgatgag ccaaaaaaat gtaatcaata ttgttgatga taatattaag    2100
aagtaccaca cggaatatac ctaa                                           2124
```

<210> SEQ ID NO 27
<211> LENGTH: 2125

```
<212> TYPE: DNA
<213> ORGANISM: Artificial Sequence
<220> FEATURE:
<223> OTHER INFORMATION: Synthetic Oligonucleotide

<400> SEQUENCE: 27
atgaaatttg gaaacttttt gcttacatac caacctcccc aatttcccca aacagaggta      60
atgaaacgtt tggttaaatt aggtcgcatc tctgaggagt gtggttttga taccgtatgg     120
ttactggagc atcatttcac ggagtttggt ttgcttggta acccttatgt cgctgctgca     180
tatttacttg gcgcgactaa aaaattgaat gtaggaactg ccgctattgt tcttcccaca     240
gcccatccag tacgccaact tgaagatgtg aatttattgg atcaaatgtc aaaaggacga     300
tttcggtttg gtatttgccg agggctttac aacaaggact ttcgcgtatt cggaacagat     360
atgaataaca gtcgcgcctt agcggaatgc tggtacgggc tgataaagaa tggcatgaca     420
gagggatata tggaagctga taatgaacat atcaagttcc ataaggtaaa agtaaacccc     480
gcggcgtata gcagaggtgg cgcaccggtt tatgtggtgg ctgaatcagc ttcgacgact     540
gagtgggctg ctcaatttgg cctaccgatg atattaagtt ggattataaa tactaacgaa     600
aagaaagcac aacttgagct ttataatgaa gtggctcaag aatatgggca cgatattcat     660
aatatcgacc attgcttatc atatataaca tctgtagatc atgactcaat taaagcgaaa     720
gagatttgcc ggaaatttct ggggcattgg tatgattctt atgtgaatgc tacgactatt     780
tttgatgatt cagaccaaac aagaggttat gatttcaata aagggcagtg cgtgactttt     840
gtattaaaag gacataaaga tactaatcgc cgtattgatt acagttacga aatcaatccc     900
gtgggaacgc cgcaggaatg tattgacata attcaaaaag cattgatgc tacaggaata     960
tcaaatattt gttgtggatt tgaagctaat ggaacagtag acgaaattat tgcttccatg    1020
aagctcttcc agtctgatgt catgccattt cttaaagaaa aacaacgtta gactattata    1080
ttatggcggt ggcggtagcg gcggtggcgg tagcggcggt ggcggtagcg gcggtggcgg    1140
tagcaaattt ggattgttct tccttaactt catcaattca acaactgttc aagaacagag    1200
tatagttcgc atgcaggaaa taacggagta tgttgataag ttgaattttg aacagatttt    1260
agtgtatgaa aatcatttt cagataatgg tgttgtcggc gctcctctga ctgtttctgg    1320
ttttctgctc ggtttaacag agaaaattaa aattggttca ttaaatcaca tcattacaac    1380
tcatcatcct gtccgcatag cggaggaagc ttgcttattg gatcagttaa gtgaagggag    1440
atttatttta gggtttagtg attgcgaaaa aaaagatgaa atgcatttt ttaatcgccc    1500
ggttgaatat caacagcaac tatttgaaga gtgttatgaa atcattaacg atgctttaac    1560
aacaggctat tgtaatccag ataacgattt ttatagcttc cctaaaatat ctgtaaatcc    1620
ccatgcttat acgccaggcg gacctcggaa atatgtaaca gcaaccagtc atcatattgt    1680
tgagtgggcg gccaaaaaag gtattcctct catctttaag tgggatgatt ctaatgatgt    1740
tagatatgaa tatgctgaaa gatataaagc cgttgcggat aaatatgacg ttgacctatc    1800
agagatagac catcagttaa tgatattagt taactataac gaagatagta ataaagctaa    1860
acaagagacg cgtgcattta ttagtgatta tgttcttgaa atgcacccta atgaaaattt    1920
cgaaaataaa cttgaagaaa taattgcaga aaacgctgtc ggaaattata cggagtgtat    1980
aactgcggct aagttggcaa ttgaaaagtg tggtgcgaaa agtgtattgc tgtcctttga    2040
accaatgaat gatttgatga gccaaaaaaa tgtaatcaat attgttgatg ataatattaa    2100
gaagtaccac acggaatata cctaa                                          2125
```

<210> SEQ ID NO 28
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 28
aggcttgtag ctcaggtggt tagagcgcac ccctccctaa gggtgaggtc ggtggttcaa     60
gtccactcag gcctacca                                                  78

<210> SEQ ID NO 29
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 29
ggcgcgttaa caaagcggtt atgtagcgga ttaccgaatc cgtctagtcc ggttcgactc     60
cggaacgcgc ctcca                                                     75

<210> SEQ ID NO 30
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 30
cgcggggtgg agcagcctgg tagctcgtcg ggctccataa cccgaaggtc gtcggttcaa     60
atccggcccc cgcaacca                                                  78

<210> SEQ ID NO 31
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 31
ggcccctTag ctcagtggtt agagcaggcg actccctaat cgcttggtcg ctggttcaag    60
tccagcaggg gccacca                                                   77

<210> SEQ ID NO 32
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 32
ggagcggtag ttcagtcggt tagaatacct gcctccctac gcaggggtc gcggttcga      60 gtcccgtccg ttccgcca                                                  78

<210> SEQ ID NO 33
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 33

```
gcccggatag ctcagtcggt agagcagggg atttgtaaat ccccgtgtcc ttggttcgat    60
tccgagtccg ggcacca                                                   77

<210> SEQ ID NO 34
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 34
gcccggatag ctcagtcggt agagcagggg attaccgaat ccccgtgtcc ttggttcgat    60
tccgagtccg ggcacca                                                   77

<210> SEQ ID NO 35
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 35
gtggctatag ctcagttggt agagccctgg atttgtaatt ccagttgtcg tgggttcgaa    60
tcccattagc caccca                                                    77

<210> SEQ ID NO 36
<211> LENGTH: 86
<212> TYPE: DNA
<213> ORGANISM: Artificial Sequence
<220> FEATURE:
<223> OTHER INFORMATION: Synthetic Organism

<400> SEQUENCE: 36
ggtggggttc ccgagcggcc aaagggagca gacttgtaaa tctgccgtca cagacttcga    60
aggttcgaat ccttccccca ccacca                                         86

<210> SEQ ID NO 37
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 37
tcctctgtag ttcagtcggt agaacggcgg acttcctaat ccgtatgtca ctggttcgag    60
tccagtcaga ggagcca                                                   77

<210> SEQ ID NO 38
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 38
ggagcggtag ttcagtcggt tagaatacct gcctgccgac gcaggggtc gcggttcga     60 gtcccgtccg ttccgcca                                                  78

<210> SEQ ID NO 39
<211> LENGTH: 91
<212> TYPE: DNA
```

<213> ORGANISM: Artificial Sequence
<220> FEATURE:
<223> OTHER INFORMATION: Synthetic Oligonucleotide

<400> SEQUENCE: 39
ggagagatgc cggagcggct gaacggaccg gtcttgtaaa accggagtag gggcaactct    60
accgggggtt caaatccccc tctctccgcc a    91

<210> SEQ ID NO 40
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 40
gcatccgtag ttcagctgga tagagtactc ggctacctaa ccgagcggtc ggaggttcga    60
atcctcccgg atgcacca    78

<210> SEQ ID NO 41
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 41
aggggcgtag ttcaattggt agagcaccgg tctacccaaa ccgggtgttg ggagttcgag    60
ttctccgccc ctgcca    76

<210> SEQ ID NO 42
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 42
ggtggggttc ccgagcggcc aaagggagca gactcctgaa tctgccgtca cagacttcga    60
aggttcgaat ccttccccca ccacca    86

<210> SEQ ID NO 43
<211> LENGTH: 115
<212> TYPE: DNA
<213> ORGANISM: Artificial Sequence
<220> FEATURE:
<223> OTHER INFORMATION: Synthetic Oligonucleotide

<400> SEQUENCE: 43
ttggtacgta aacgcatcgt ggggctatag ctcagctggg agagcgcttg catcctgatg    60
caagaggtca gcggttcgat cccgcttagc tccaccaaam ccaaccctcg ctgca    115

<210> SEQ ID NO 44
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 44
gccgatatag ctcagttggt agagcagcgc attccctaat gcgaaggtcg taggttcgac    60
tcctattatc ggcacca    77

<210> SEQ ID NO 45
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 45
gcgtccgtag ctcagttggt tagagcacca ccttgccgat ggtgggggtc ggtggttcga    60
gtccactcgg acgcacca                                                  78

<210> SEQ ID NO 46
<211> LENGTH: 115
<212> TYPE: DNA
<213> ORGANISM: Artificial Sequence
<220> FEATURE:
<223> OTHER INFORMATION: Synthetic Oligonucleotide

<400> SEQUENCE: 46
ttggtacgta aacgcatcgt ggggctatag ctcagctggg agagcgcttg catccctatg    60
caagaggtca gcggttcgat cccgcttagc tccaccaaam ccaaccctcg ctgca        115

<210> SEQ ID NO 47
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 47
gcgtccgtag ctcagttggt tagagcacca ccttaccgat ggtgggggtc ggtggttcga    60
gtccactcgg acgcacca                                                  78

<210> SEQ ID NO 48
<211> LENGTH: 110
<212> TYPE: DNA
<213> ORGANISM: Artificial Sequence
<220> FEATURE:
<223> OTHER INFORMATION: Synthetic Oligonucleotide

<400> SEQUENCE: 48
gcaaggggtc gttagctcag ttggtagagc agttgacttt ctaatcaatt ggtcgcaggt    60
tcgaatcctg cacgacccac caatgtaaaa aagcgcccta aaggcgcttm             110

<210> SEQ ID NO 49
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 49
gcgtccgtag ctcagttggt tagagcacca cctttcctat ggtgggggtc ggtggttcga    60
gtccactcgg acgcacca                                                  78

<210> SEQ ID NO 50
<211> LENGTH: 86
<212> TYPE: DNA
<213> ORGANISM: Artificial Sequence
<220> FEATURE:
<223> OTHER INFORMATION: Synthetic Oligonucleotide

```
<400> SEQUENCE: 50
gccgaagtgg cgaaatcggt agacgcagtt gattccctaa tcaaccgtag aaatacgtgc    60
cggttcgagt ccggccttcg gcacca                                          86

<210> SEQ ID NO 51
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 51
gtggctatag ctcagttggt agagccctgg attacctatt ccagttgtcg tgggttcgaa    60
tcccattagc caccca                                                     77

<210> SEQ ID NO 52
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 52 gtcccctteg tctagaggcc caggacaccg ccctccctac ggcggtaaca ggggttcgaa    60
tcccctaggg gacgcca                                                    77

<210> SEQ ID NO 53
<211> LENGTH: 113
<212> TYPE: DNA
<213> ORGANISM: Artificial Sequence
<220> FEATURE:
<223> OTHER INFORMATION: Synthetic Oligonucleotide

<400> SEQUENCE: 53
ctgaaaggcc tgaagaamgg cgcgttaaca aagcggttat gtagcggatt gccgaatccg    60
tctagtccgg ttcgactccg gaacgcgcct ccactttctt cccgagcccg gat          113

<210> SEQ ID NO 54
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 54
cgcggggtgg agcagcctgg tagctcgtcg ggctccctaa cccgaaggtc gtcggttcaa    60
atccggcccc cgcaacca                                                   78

<210> SEQ ID NO 55
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 55
aggcttgtag ctcaggtggt tagagcgcac cccttcctaa gggtgaggtc ggtggttcaa    60
gtccactcag gcctacca                                                   78

<210> SEQ ID NO 56
<211> LENGTH: 75
```

```
<212> TYPE: DNA
<213> ORGANISM: Artificial Sequence
<220> FEATURE:
<223> OTHER INFORMATION: Synthetic Oligonucleotide

<400> SEQUENCE: 56
gcgggcgtag ttcaatggta gaacgagagc ttccctaagc tctatacgag ggttcgattc      60
ccttcgcccg ctcca                                                      75

<210> SEQ ID NO 57
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 57
gccgaagtgg cgaaatcggt agacgcagtt gatttcctaa tcaaccgtag aaatacgtgc      60
cggttcgagt ccggccttcg gcacca                                          86

<210> SEQ ID NO 58
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 58
gcatccgtag ttcagctgga tagagtactc ggctccctaa ccgagcggtc ggaggttcga      60
atcctcccgg atgcacca                                                   78

<210> SEQ ID NO 59
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 59
gcccggatag ctcagtcggt agagcagggg attgccgaat ccccgtgtcc ttggttcgat      60
tccgagtccg ggcacca                                                    77

<210> SEQ ID NO 60
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 60
ggctacgtag ctcagttggt tagagcacat cactccctaa tgatggggtc acaggttcga      60
atcccgtcgt agccacca                                                   78

<210> SEQ ID NO 61
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 61
gtccccttcg tctagaggcc caggacaccg cccttcctac ggcggtaaca ggggttcgaa      60
```

```
tccccctaggg gacgcca                                                    77

<210> SEQ ID NO 62
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 62 gtcccccttcg tctagaggcc caggacaccg ccctaccgac ggcggtaaca ggggttcgaa     60 tccccctaggg gacgcca                                                    77

<210> SEQ ID NO 63
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 63
aggggcgtag ttcaattggt agagcaccgg tctccctaaa ccgggtgttg ggagttcgag      60
tctctccgcc cctgcca                                                    77

<210> SEQ ID NO 64
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 64
gcatccgtag ttcagctgga tagagtactc ggctaccgaa ccgagcggtc ggaggttcga     60
atcctcccgg atgcacca                                                   78

<210> SEQ ID NO 65
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 65
gtggctatag ctcagttggt agagccctgg attccctatt ccagttgtcg tgggttcgaa    60
tcccattagc caccca                                                    77

<210> SEQ ID NO 66
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 66
ggagagatgc cggagcggct gaacggaccg gtctccctaa accggagtag gggcaactct     60
accgggggtt caaatccccc tctctccgcc a                                    91

<210> SEQ ID NO 67
<211> LENGTH: 91
<212> TYPE: DNA
<213> ORGANISM: Artificial Sequence
<220> FEATURE:
<223> OTHER INFORMATION: Synthetic Oligonucleotide
```

<400> SEQUENCE: 67
ggagagatgc cggagcggct gaacggaccg gtctgccgaa accggagtag gggcaactct    60
accgggggtt caaatccccc tctctccgcc a                                   91

<210> SEQ ID NO 68
<211> LENGTH: 117
<212> TYPE: DNA
<213> ORGANISM: Artificial Sequence
<220> FEATURE:
<223> OTHER INFORMATION: Synthetic Oligonucleotide

<400> SEQUENCE: 68
ttggtacgta aacgcatcgt ggggctatag ctcagctggg agagcgcttg catacccatg    60
caagaggtca gcggttcgat cccgcttagc tccaccaaat ttccaaccct cgctgca      117

<210> SEQ ID NO 69
<211> LENGTH: 77
<212> TYPE: DNA
<213> ORGANISM: Artificial Sequence
<220> FEATURE:
<223> OTHER INFORMATION: SEQ ID NO: 70

<400> SEQUENCE: 69
gtggctatag ctcagttggt agagccctgg attactgatt ccagttgtcg tgggttcgaa    60
tcccattagc caccca                                                    77

<210> SEQ ID NO 70
<211> LENGTH: 117
<212> TYPE: DNA
<213> ORGANISM: Artificial Sequence
<220> FEATURE:
<223> OTHER INFORMATION: Synthetic Oligonucleotide

<400> SEQUENCE: 70
ttggtacgta aacgcatcgt ggggctatag ctcagctggg agagcgcttg catcccatg    60 caagaggtca gcggttcgat cccgcttagc tccaccaaat ttccaaccct cgctgca      117

<210> SEQ ID NO 71
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 71
aggggcgtag ttcaattggt agagcaccgg tctccccaaa ccgggtgttg ggagttcgag    60
tctctccgcc cctgcca                                                  77

<210> SEQ ID NO 72
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 72
gccgaagtgg cgaaatcggt agacgcagtt gattaccgaa tcaaccgtag aaatacgtgc    60
cggttcgagt ccggccttcg gcacca                                         86

<210> SEQ ID NO 73

```
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 73
ggagcggtag ttcagtcggt tagaatacct gcctgtccac gcaggggtc gcgggttcga    60 gtcccgtccg ttccgcca                                                  78

<210> SEQ ID NO 74
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 74
tcctctgtag ttcagtcggt agaacggcgg actatttaat ccgtatgtca ctggttcgag    60
tccagtcaga ggagcca                                                   77

<210> SEQ ID NO 75
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 75 ggcccctag ctcagtggtt agagcaggcg acttctaaat cgcttggtcg ctggttcaag    60
tccagcaggg gccacca                                                   77

<210> SEQ ID NO 76
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 76
ggagagatgc cggagcggct gaacggaccg gtctatgcaa accggagtag gggcaactct    60
accgggggtt caaatccccc tctctccgcc a                                   91

<210> SEQ ID NO 77
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 77
tcctctgtag ttcagtcggt agaacggcgg actaccgaat ccgtatgtca ctggttcgag    60
tccagtcaga ggagcca                                                   77

<210> SEQ ID NO 78
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 78
tcctctgtag ttcagtcggt agaacggcgg actcctgaat ccgtatgtca ctggttcgag    60
```
tccagtcaga ggagcca                                                          77

<210> SEQ ID NO 79
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 79
tcctctgtag ttcagtcggt agaacggcgg actaattaat ccgtatgtca ctggttcgag    60
tccagtcaga ggagcca                                                          77

<210> SEQ ID NO 80
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 80
ggctacgtag ctcagttggt tagagcacat cacttctaaa tgatggggtc acaggttcga    60
atcccgtcgt agccacca                                                         78

<210> SEQ ID NO 81
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 81
tcctctgtag ttcagtcggt agaacggcgg actggttaat ccgtatgtca ctggttcgag    60
tccagtcaga ggagcca                                                          77

<210> SEQ ID NO 82
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 82
tcctctgtag ttcagtcggt agaacggcgg actccctaat ccgtatgtca ctggttcgag    60
tccagtcaga ggagcca                                                          77

<210> SEQ ID NO 83
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 83
ggagcggtag ttcagtcggt tagaatacct gcctgcctac gcaggggtc gcgggttcga    60 gtcccgtccg ttccgcca                                                         78

<210> SEQ ID NO 84
<211> LENGTH: 77
<212> TYPE: DNA
<213> ORGANISM: Artificial Sequence
<220> FEATURE:

<223> OTHER INFORMATION: Synthetic Oligonucleotide

<400> SEQUENCE: 84
tcctctgtag ttcagtcggt agaacggcgg acttgtaaat ccgtatgtca ctggttcgag    60
tccagtcaga ggagcca                                                   77

<210> SEQ ID NO 85
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 85
ggctacgtag ctcagttggt tagagcacat cactccataa tgatggggtc acaggttcga    60
atcccgtcgt agccacca                                                  78

<210> SEQ ID NO 86
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 86
ggccccttag ctcagtggtt agagcaggcg actccataat cgcttggtcg ctggttcaag    60
tccagcaggg gccacca                                                   77

<210> SEQ ID NO 87
<211> LENGTH: 78
<212> TYPE: DNA
<213> ORGANISM: Artificial Sequence
<220> FEATURE:
<223> OTHER INFORMATION: Synthetic Organism

<400> SEQUENCE: 87
cgcggggtgg agcagcctgg tagctcgtcg ggcttctaaa cccgaaggtc gtcggttcaa    60
atccggcccc cgcaacca                                                  78

<210> SEQ ID NO 88
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 88
gcatccgtag ttcagctgga tagagcactc ggcttctaaa ccgatcggtc ggaggttcga    60
atcctcccgg atgcacca                                                  78

<210> SEQ ID NO 89
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 89
aggggcgtag ttcaattggt agaacaccgg tcttctaata ccgggtgttg ggagttcgag    60
tctctccgcc cccgcca                                                   77

```
<210> SEQ ID NO 90
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 90
ggagagatgc cggagcggct gaacggaccg gtatccgaac accggagtag gggcaactct    60
accgggggtt caaatccccc tctctccgcc a                                   91

<210> SEQ ID NO 91
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 91
gtccccttcg tctagaggcc caggacaccg cccttctaat ggcggtaaca ggggttcgaa    60
tcccctaggg gacgcca                                                    77

<210> SEQ ID NO 92
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 92
gcccggatag ctcagtcggt agagcagggg acttctaatt ccccgtgtcc ttggttcgat    60
tccgagtccg ggcacca                                                    77

<210> SEQ ID NO 93
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 93
gcccggatag ctcagtcggt agagcagggg aattctagct ccccgtgtcc ttggttcgat    60
tccgagtccg ggcacca                                                    77

<210> SEQ ID NO 94
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 94
gcccggatag ctcagtcggt agagcagggg agttctagtt ccccgtgtcc ttggttcgat    60
tccgagtccg ggcacca                                                    77

<210> SEQ ID NO 95
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 95
```
gcgggcgtag ttcaatggta gaacgagagc cttctagtgc tctatacgag ggttcgattc    60
ccttcgcccg ctcca    75

<210> SEQ ID NO 96
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 96
gtggctatag ctcagttggt agagccctgg acttctaatt ccagttgtcg tgggttcgaa    60
tcccattagc caccca    77

<210> SEQ ID NO 97
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 97
gtggctatag ctcagttggt agagccctgg agttctaatt ccagttgtcg tgggttcgaa    60
tcccattagc caccca    77

<210> SEQ ID NO 98
<211> LENGTH: 77
<212> TYPE: RNA
<213> ORGANISM: Artificial Sequence
<220> FEATURE:
<223> OTHER INFORMATION: Synthetic Oligonucleotide

<400> SEQUENCE: 98 gggggguaucg ccaagcggua aggcaccgga uuccugauu ccggcauucc gagguucgaa    60
uccucguacc ccagcca    77

<210> SEQ ID NO 99
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 99 uggggguaucg ccaagcggua aggcaccgga cuucuaauuc cggcauuccg agguucgaau    60
ccucguaccc cagcca    76

<210> SEQ ID NO 100
<211> LENGTH: 75
<212> TYPE: RNA
<213> ORGANISM: Artificial Sequence
<220> FEATURE:
<223> OTHER INFORMATION: Synthetic Oligonucleotide

<400> SEQUENCE: 100 uggggguaucg ccaagcggua aggcaccgga cuucuaauuc cggcauccga gguucgaauc    60
cucguacccc agcca    75

<210> SEQ ID NO 101
<211> LENGTH: 86
<212> TYPE: RNA
<213> ORGANISM: Artificial Sequence

```
<220> FEATURE:
<223> OTHER INFORMATION: Synthetic Oligonucleotide

<400> SEQUENCE: 101 gguggguuc ccgagcggcc aaagggagca gaacucuaaa ucugccguca ucgacuucga    60
agguucgaau ccuuccccca ccacca                                       86

<210> SEQ ID NO 102
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 102
gcauccguag ucagcugga uagaguacuc ggcuucuaaa ccgaucgguc ggagguucga    60
auccucccgg augcacca                                                78

<210> SEQ ID NO 103
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 103
gcauccguag uucagcugga uagagcacuc ggcuucuaaa ccgaucgguc ggagguucga    60
auccucccgg augcacca                                                78

<210> SEQ ID NO 104
<211> LENGTH: 77
<212> TYPE: RNA
<213> ORGANISM: Artificial Sequence
<220> FEATURE:
<223> OTHER INFORMATION: Synthetic Oligonucleotide

<400> SEQUENCE: 104
aggggcguag uucaauuggu agaacaccgg ucuucuaaua ccggguguug ggaguucgag    60
ucucuccgcc cccgcca                                                 77

<210> SEQ ID NO 105
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 105
ggagagaugc cggagcggcu gaacggaccg gucucgaaaa ccgaguagg ggcaacucua    60 ccgggggguuc aaauccccu cucuccgcca                                   90

<210> SEQ ID NO 106
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 106
ggucuucuaa aacc                                                    14

<210> SEQ ID NO 107
```

```
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 107
gguauucuaa cacc                                                     14

<210> SEQ ID NO 108
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 108
gggauucuaa cccc                                                     14

<210> SEQ ID NO 109
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 109

Met Gln Arg Thr Thr Ile Ile Leu Trp Arg Trp Arg
1               5                   10

<210> SEQ ID NO 110
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 110
atgcaacgta ccactattat attatggcgg tggcggtagc acctaa                   46

<210> SEQ ID NO 111
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Quadruplet-encoded amino acid
<220> FEATURE:
<221> NAME/KEY: MISC_FEATURE
<222> LOCATION: (4)..(4)
<223> OTHER INFORMATION: Quadruplet-encoded amino acid

<400> SEQUENCE: 111

Met Gln Arg Xaa Leu Leu Tyr Tyr Gly Gly Gly Gly Ser Thr
1               5                   10

<210> SEQ ID NO 112
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 112
gaaagttgtt tagcaaaaac gccatacaga aaattcattt                          40
```

<210> SEQ ID NO 113
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 113
aaatgaattt tctgtatgcc gttttttgcta aacaactttc          40

<210> SEQ ID NO 114
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(7)
<223> OTHER INFORMATION: Quadruplet-encoded amino acid

<400> SEQUENCE: 114

Glu Ser Cys Leu Ala Lys Xaa His Thr Glu Asn Ser Phe
1               5                   10

<210> SEQ ID NO 115
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 115
gttgtttagc aaaatagaca tacagaaaat tc          32

<210> SEQ ID NO 116
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 116
tgaattttct gtatgtctat tttgctaaac aacc          34

<210> SEQ ID NO 117
<211> LENGTH: 11
<212> TYPE: PRT
<213> ORGANISM: Artificial Sequence
<220> FEATURE:
<223> OTHER INFORMATION: Synthetic Oligonucleotide
<220> FEATURE:
<221> NAME/KEY: MISC_FEATURE
<223> OTHER INFORMATION: Quadruplet codon-encoded amino acid
<220> FEATURE:
<221> NAME/KEY: MISC_FEATURE
<222> LOCATION: (6)..(6)
<223> OTHER INFORMATION: Quadruplet codon-encoded amino acid

<400> SEQUENCE: 117

Ser Cys Leu Ala Lys Xaa His Thr Glu Asn Ser
1               5                   10

<210> SEQ ID NO 118
<211> LENGTH: 77
<212> TYPE: RNA
<213> ORGANISM: Artificial Sequence
<220> FEATURE:

```
<223> OTHER INFORMATION: Synthetic Oligonucleotide

<400> SEQUENCE: 118
aggggcguag uucaauuggu agaacaccgg ucuucuaaua ccggguguug ggaguucgag      60
ucucuccgcc cccgcca                                                    77

<210> SEQ ID NO 119
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 119

Leu Glu Tyr Asn Phe Asn Ser His Asn Val Tyr Ile Thr Ala Asp Lys
1               5                   10                  15

<210> SEQ ID NO 120
<211> LENGTH: 77
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: mutation
<222> LOCATION: (39)..(39)
<223> OTHER INFORMATION: U
<220> FEATURE:
<221> NAME/KEY: mutation
<222> LOCATION: (73)..(73)
<223> OTHER INFORMATION: C

<400> SEQUENCE: 120
aggggcguag uucaauuggu agagcaccgg ucuucuaaaa ccggguguug ggaguucgag      60
ucucuccgcc ccugcca                                                    77

<210> SEQ ID NO 121
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 121

Met Tyr Ser Arg Arg Ser Leu Thr
1               5

<210> SEQ ID NO 122
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 122
atgtattaga agacgttaga ctaacctaa                                       29

<210> SEQ ID NO 123
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 123
tcatagatag atcatcatca tca                                             23
```

<210> SEQ ID NO 124
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 124
tgatgatgat gatctatcta tga                                        23

<210> SEQ ID NO 125
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 125
tcatagatca tagatcatca tca                                        23

<210> SEQ ID NO 126
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 126
tgatgatgat ctatgatcta tga                                        23

<210> SEQ ID NO 127
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 127
tcatagatca tcatagatca tca                                        23

<210> SEQ ID NO 128
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 128
tgatgatcta tgatgatcta tga                                        23

<210> SEQ ID NO 129
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 129
tcatagatca tcatcataga tca                                        23

<210> SEQ ID NO 130
<211> LENGTH: 23
<212> TYPE: DNA
<213> ORGANISM: Artificial Sequence
<220> FEATURE:

<223> OTHER INFORMATION: Synthetic Oligonucleotide

<400> SEQUENCE: 130
tgatctatga tgatgatcta tga                                           23

<210> SEQ ID NO 131
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 131
ggggctatag ctcagctggg agagcgcttg cttccctagg caagaggtca gcggttcgat    60
cccgcttagc tccacca                                                  77

<210> SEQ ID NO 132
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 132
ggagagatgc cggagcggct gaacggaccg gtctccctat accggagtag gggcaactct    60
accgggggtt caaatccccc tctctccgcc a                                  91

<210> SEQ ID NO 133
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 133
gcgggcgtag ttcaatggta gaacgagagc ctccctatgc tctatacgag ggttcgattc    60
ccttcgcccg ctcca                                                    75

<210> SEQ ID NO 134
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 134
ggagcggtag ttcagtcggt tagaatacct gcgtccctaa gcaggggggtc gcgggttcga   60 gtcccgtccg ttccgcca                                                 78

<210> SEQ ID NO 135
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 135
gcccggatag ctcagtcggt agagcagggg agtgccgatt ccccgtgtcc ttggttcgat    60
tccgagtccg ggcacca                                                  77

<210> SEQ ID NO 136
<211> LENGTH: 78

```
<212> TYPE: DNA
<213> ORGANISM: Artificial Sequence
<220> FEATURE:
<223> OTHER INFORMATION: Synthetic Oligonucleotide

<400> SEQUENCE: 136
gcatccgtag ttcagctgga tagagtactc gggtgccgaa ccgagcggtc ggaggttcga      60
atcctcccgg atgcacca                                                   78

<210> SEQ ID NO 137
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 137
gtggctatag ctcagttggt agagccctgg agttgtaatt ccagttgtcg tgggttcgaa      60
tcccattagc cacccca                                                    77

<210> SEQ ID NO 138
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 138
ggagagatgc cggagcggct gaacggaccg gtattgtaaa accggagtag gggcaactct      60
accgggggtt caaatccccc tctctccgcc a                                    91

<210> SEQ ID NO 139
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 139
gcccggatag ctcagtcggt agagcagggg aattctaaat ccccgtgtcc ttggttcgat      60
tccgagtccg ggcacca                                                    77

<210> SEQ ID NO 140
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 140
gcccggatag ctcagtcggt agagcagggg aattctaaat cctcgtgtcc ttggttcgat      60
tccgagtccg ggcacca                                                    77

<210> SEQ ID NO 141
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 141
gtggctatag ctcagttggt agagccctgg atttctaatt ccagtgtcgt gggttcgaat     60
```

```
cccattagcc acccca                                              76

<210> SEQ ID NO 142
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 142
gtggctatag ctcagttggt agagccctgg acttctaatt ccagtgtcgt gggttcgaat    60
cccattagcc acccca                                              76

<210> SEQ ID NO 143
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 143
gtggctatag ctcagttggt agagccctgg acttctaatt ccagttgtgt gggttcgaat    60
cccattagcc acccca                                              76

<210> SEQ ID NO 144
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 144
ggagagatgc cggagcggct gaacggaccg gtcttctaat accggagtag gggcaactct    60
accgggggtt caaatccccc tctctccgcc a                             91

<210> SEQ ID NO 145
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 145
ggagagatgc cggagcggct gaacggaccg gtcttctaaa atcggagtag gggcaactct    60
accgggggtt caaatccccc tctctccgcc a                             91
```

FRAMESHIFT SUPPRESSOR tRNA COMPOSITIONS AND METHODS OF USE

RELATED APPLICATIONS

This application claims the benefit under 35 U.S.C. § 119(e) of U.S. Provisional application Ser. No. 62/989,920 filed Mar. 16, 2020, U.S. Provisional application Ser. No. 62/936,734 filed Nov. 18, 2019, and U.S. Provisional application Ser. No. 62/858,717 filed Jun. 7, 2019, the disclosure of each of which is incorporated by reference herein in its entirety.

GOVERNMENT INTEREST

This invention was made with government support under DP5 OD024590 and F31 AI145181 awarded by the National Institutes of Health, and NNH17ZDA001N awarded by the National Aeronautics and Space Administration. The government has certain rights in the invention.

FIELD OF THE INVENTION

This disclosure relates generally to suppressor tRNA compounds, compositions comprising suppressor tRNA compounds, and methods to identify, evolve, and use suppressor tRNA compounds.

BACKGROUND OF THE INVENTION

Every living organism uses a genetic code in which three base pairs are translated into one amino acid. The origin of triplet codon universality is intriguing given that naturally occurring four-base codons can be translated by cognate quadruplet decoding tRNAs. Previous studies attempting to use quadruplet decoding to incorporate unnatural amino acids have proven less effective than triplet decoding approaches such as amber suppression, and the basis for this difficulty, and means to improve quadruplet decoding remain unknown.

Previous suppressor tRNAs often contain a one-bp insertion in their anticodon loop, and generate a frameshift during translation, effectively causing them to decode a 'quadruplet codon' [Atkins, J. F. & Björk, G. R. *Microbiol. Mol. Biol. Rev.* 73, 178-210 (2009)]. Puzzlingly, some suppressor tRNAs only require Watson-Crick matching between the first three-bases of the four-base codon [Bossi, L. & Roth, J. R. *Cell* 25, 489-496 (1981) and Wang, N., et al., *Sci. Rep.* 6, 21898 (2016)], while others benefit from all four-bases matching [Magliery, T. J., et al., (Edited by M. Gottesman). *J. Mol. Biol.* 307, 755-769 (2001); Curran, J. F. & Yarus, M. *Science* 238, 1545-1550 (1987); and Gaber, R. F. & Culbertson, M. R. *Mol. Cell. Biol.* 4, 2052-2061 (1984)].

Studying suppressor tRNAs has been further complicated by their dependence on transcript sequence context [Salser, W. *Mol. Gen. Genet.* 105, 125-130 (1969); Fluck, M. M., et al., *Mol. Gen. Genet.* 151, 137-149 (1977); Salser, W., et al., *Cold Spring Harb. Symp. Quant. Biol.* 34, 513-520 (1969); Yahata, H., et al., *Mol. Gen. Genet.* 106, 208-212 (1970); Akaboshi, E., Inouye, M. & Tsugita, A. *Mol. Gen. Genet.* 149, 1-4 (1976); Feinstein, S. I. & Altman, S. *J. Mol. Biol.* 112, 453-470 (1977); Colby, D. S., et al., *Cell* November: 9(3):449-63 (1976); Feinstein, S. I. & Altman, S. *Genetics* 88, 201-219 (1978); and Fluck, M. M. & Epstein, R. H. *Mol. Gen. Genet.* 177, 615-627 (1980)] and low efficiency in vivo [Italia, J. S., et al., (2019) J. Am. Chem. Soc. April 17; 141(15):6204-6212]. Quadruplet codons have already been used together with amber suppressors to site-specifically integrate two distinct Non-Canonical Amino Acids (NCAAs) into a single protein chain [Neumann, H., et al., *Nature* 464, 441-444 (2010)]. Quadruplet decoding is an attractive strategy for genetic code expansion because exclusive quadruplet translation offers, in theory, 256 unique codons. However, it is unclear whether exclusive quadruplet translation is possible, and the existing state of the art is far from this goal. Indeed, all quadruplet decoding tRNAs used for NCAAs involve just eight quadruplet codons: UAGN, AGGN; hardly an expanded codon set. All quadruplet decoding tRNAs that have been used for quadruplet decoding engineering in bacteria are based on just five distinct tRNA scaffolds: Serine from *E. coli* 4; Tyrosine [Wang, L., et al., *J. Am. Chem. Soc.* 122, 5010-5011 (2000)] and Leucine; [Wang, L., et al., *J. Am. Chem. Soc.* 122, 5010-5011 (2000) 18] from *M. jannaschii*; Pyrrolysine from *M. mazei* or *M. barkeri* [Nozawa, K. et al. *Nature* 457, 1163-1167 (2009); Fekner, T. & Chan, M. K. *Curr. Opin. Chem. Biol.* 15, 387-391 (2011], and a consensus Archaeal Lysine based on *P. horikoshii* [Anderson, J. C. et al. *Proc. Natl. Acad. Sci. U S A.* 101, 7566-7571 (2004)]. In comparison, stop codon suppressor engineering has been comprehensively studied [Kleina, L. G., et al., *J. Mol. Biol.* 213, 705-717 (1990); Normanly, J., et al., *Proc. Natl. Acad. Sci. U S A.* 83, 6548-6552 (1986); Normanly, J., et al., *J. Mol. Biol.* 213, 719-726 (1990); and Hoesl, M. G. & Budisa, N. *Biotechnol.* 23, 751-757 (2012)], and is generally higher efficiency, making it preferred for NCAA incorporation today. It is thus important to determine whether the challenges of inefficiency, context dependence, and potentially heterogeneous mechanism can be overcome, or if they cause quadruplet decoding to be unsuitable for engineering applications.

SUMMARY OF THE INVENTION

According to one aspect of the invention, a composition is provided, the composition including a suppressor tRNA, wherein the suppressor tRNA is encoded by a sequence set forth as any one of SEQ ID NOs: 1-21, 28-67, 88-97, and 131-145. In certain embodiments, the composition also includes a detectable label. In some embodiments, the suppressor tRNA includes the detectable label.

According to an aspect of the invention; a cell is provided that includes the composition of any one of the aforementioned embodiments of the composition aspect of the invention. In some embodiments, the cell is a bacterial cell. In some embodiments, the cell is a mammalian cell, and optionally is a human cell. In certain embodiments, the cell is an engineered cell.

According to an aspect of the invention a composition is provided, the composition including a polynucleotide molecule, the sequence of which is set forth as one of SEQ ID NOs: 1-21, 28-67, 88-97, and 131-145. In some embodiments, the composition also includes a vector sequence. In certain embodiments, the polynucleotide molecule is part of a vector molecule.

According to an aspect of the invention, a cell is provided, the cell including at least one polynucleotide molecule, the sequence of which is set forth as one of SEQ ID NOs: 1-21, 28-67, 88-97, and 131-145. In some embodiments, the cell is a bacterial cell. In some embodiments, the cell is a mammalian cell, and optionally is a human cell. In certain embodiments, the cell is an engineered cell.

According to an aspect of the invention, a vector is provided, the vector including at least one sequence set forth as one of SEQ ID NOs: 1-21, 28-67, 88-97, and 131-145.

According to an aspect of the invention, a cell is provided, the cell including an embodiment of the aforementioned vector. In some embodiments, the cell is a bacterial cell. In some embodiments, the cell is a mammalian cell, and optionally is a human cell. In some embodiments, the cell is an engineered cell.

According to another aspect of the invention, a composition is provided, the composition including a variant LuxAB reporter molecule encoded with an independently selected quadruplet codon at one or more residues of a LuxAB protein sequence. In certain embodiments, the variant LuxAB reporter protein sequence is encoded by the sequence set forth as SEQ ID NO: 26. In some embodiments, the variant LuxAB reporter molecule is encoded with an independently selected quadruplet codon at one or both of residue 164 and residue 357 of the LuxAB protein sequence. In certain embodiments, the one or more residues of the LuxAB protein sequence include one or both residues corresponding to residues 164 and 357, respectively, of the LuxAB protein sequence set forth as SEQ ID NO: 26. In some embodiments, the variant LuxAB reporter protein sequence is encoded by the sequence set forth as SEQ ID NO: 27.

According to another aspect of the invention, an assay method is provided, the assay method including the composition of any aforementioned aspects of the invention.

According to another aspect of the invention, a method of engineering an evolved quadruplet decoding suppressor tRNA is provided, the method including: engineering an evolved quadruplet decoding suppressor tRNA from a preselected quadruplet decoding suppressor tRNA, wherein a means of the engineering comprises a phage-assisted continuing evolution (PACE) method. In certain embodiments, the PACE method comprises a bacteriophage-based directed evolution method. In some embodiments, the PACE method includes determining the presence of a successfully evolved quadruplet decoding suppressor tRNA. In some embodiments, a means for determining the presence of the successfully evolved quadruplet decoding suppressor tRNA includes detecting a phage propagation reporter, wherein successful quadruplet decoding by the evolved suppressor tRNA results in phage propagation. In certain embodiments, a means for determining the presence of the successful evolved quadruplet decoding suppressor tRNA comprises: (a) challenging (i) an essential phage protein encoded with one or more quadruplet codons and (ii) an evolved quadruplet decoding suppressor tRNA encoded on a phage from which the essential phage protein has been deleted, to infect a plurality of *E. coli*; and (b) detecting a functional phage produced in the challenged *E. coli*, wherein the functional phage produced indicates the presence of one or more successful quadruplet decoding(s) by the evolved quadruplet decoding suppressor tRNA. In some embodiments, the essential phage protein is a pIII phage protein.

According to another aspect of the invention, a composition is provided, the composition including a nucleic acid molecule set forth as SEQ ID NO: 25, or a functional variant thereof. In certain embodiments, the nucleic acid sequence is in a vector.

According to another aspect of the invention, a vector is provided, the vector including the composition of any embodiment of the aforementioned composition comprising a nucleic molecule set forth as SEQ ID NO: 25 or a variant thereof.

According to another aspect of the invention, a cell is provided, the cell comprising any embodiment of the aforementioned vector that includes a nucleic molecule set forth as SEQ ID NO: 25 or a variant thereof. In some embodiments, the cell is a bacterial cell. In certain embodiments, the cell is a mammalian cell, and optionally is a human cell. In some embodiments, the cell is an engineered cell.

According to another aspect of the invention, a method of generating a suppressor tRNA is provided. The method including: initiating transcription of a nucleic acid sequence encoding a suppressor tRNA with a PproK-lacO promoter sequence set forth as SEQ ID NO: 25, or functional variant thereof.

According to another aspect of the invention, a suppressor tRNA is provided, wherein the suppressor tRNA is encoded by a sequence set forth as any one of SEQ ID NOs: 1-21, 28-97 and 131-145.

According to another aspect of the invention, a cell that includes the suppressor tRNA of any embodiment of an aforementioned aspect of the invention is provided. In some embodiments, the cell is a bacterial cell. In certain embodiments, the cell is a mammalian cell, and optionally is a human cell. In some embodiments, the cell is an engineered cell.

According to another aspect of the invention, a method of protein translation is provided, the method including: preparing a DNA sequence that includes a quadruplet codon encoding one or more amino acids, decoding the quadruplet codon with a suppressor tRNA encoded by a sequence set forth as any one of SEQ ID NOs: 1-21, 28-67, 88-97, and 131-145; and translating the DNA sequence to produce a protein comprising the encoded amino acids. In certain embodiments, the protein translation includes both triplet and quadruplet codons. In some embodiments, the protein translation is an all-quadruplet protein translation. In some embodiments, the method also includes assessing one or more of the structure and function of the translated protein product. In certain embodiments, the decoding is performed in a cell. In some embodiments, the cell is a bacterial cell. In some embodiments, the cell is a mammalian cell, and optionally is a human cell. In certain embodiments, the cell is an engineered cell.

According to yet another aspect of the invention, a method of translating a single DNA sequence into one or more distinct protein products is provided, the method including: decoding a DNA sequence with one or more suppressor tRNAs encoded by a sequence set forth as any one of SEQ ID NOs: 1-21, 28-68, 88-97, and 131-145 wherein the presence of the one or more suppressor tRNAs determines the translated protein product of the contacted DNA sequence; and translating the decoded DNA sequence into the translated protein product. In some embodiments, the method also includes assessing one or more of the structure and function of the translated protein product. In some embodiments, the DNA sequence includes one or more quadruplet codons encoding canonical amino acids. In certain embodiments, the decoding step is under suitable conditions for translation of the DNA sequence. In some embodiments, the decoding is performed in a cell. In certain embodiments, the cell is a bacterial cell. In some embodiments, the cell is a mammalian cell, and optionally is a human cell. In some embodiments, the cell is an engineered cell.

According to another aspect of the invention, a composition including a suppressor tRNA, wherein the suppressor tRNA is encoded by a sequence set forth as any one of SEQ ID NOs: 1-97 and 131-145 is provided. According to another aspect of the invention a cell including any embodiment of an aforementioned composition is provided.

BRIEF DESCRIPTION OF THE DRAWINGS

FIG. 1 shows sequences encoding suppressor tRNA sequences. SEQ ID NOs: 1-15 are novel sequences identified as described elsewhere herein. SEQ ID NOs: 22 and 23 are previously described sequences.

FIG. 2 shows sequences encoding evolved suppressor tRNAs. SEQ ID NOs: 16-21 are novel sequences identified as described herein. SEQ ID NO: 24 is a previously described sequence.

FIG. 3 provides information about previously identified suppressors including the literature references for each listed suppressor.

FIG. 4A-I provides schematic diagrams, graphs, and a table that provide details of certain embodiments of a luciferase-based reporter of quadruplet decoding. FIG. 4A illustrates elements of two plasmids. Top schematic shows plasmid constitutively that expressed a luciferase that was encoded using a quadruplet codon at permissive residue(s) 164 or 357. Lower schematic shows second plasmid that included an IPTG inducible promoter. FIG. 4B is a schematic that illustrates how the reporter works. FIG. 4C shows results of a validation study of luciferase-based quadruplet decoding reporter that demonstrated successful validation of engineered quadruplet decoding tRNA Ser-AGGA, (data point on left). FIG. 4C also shows results of two negative controls—one prepared with a reporter containing a mismatching quadruplet codon (center data point) and one expressing a wild type Serine tRNA that did not result in luminescence (data point at right). FIG. 4D is a graph showing that naturally occurring suppressors have low quadruplet decoding efficiency. Graph indicates low or no measurable activity in this assay. Some resulted in high toxicity. FIG. 4E is a graph showing quadruplet decoding efficiency of naïve TAGA suppressors. The graph provides measurements of quadruplet decoding tRNAs that decode TAGA. FIG. 4F provides a group of quadruplet decoding efficiency of naïve XYZZ suppressors. The graph provides measurements of quadruplet decoding tRNAs that decode XYZZ, where XYZ was the original codon corresponding to each tRNA scaffold. Induction of 7 of these tRNA results in high toxicity, as indicated by X. FIG. 4G provides a table identifying minimally functional suppressors showing that the experimental results of studies revealed at least one naive quadruplet decoding tRNA with detectable activity for 13/20 canonical amino acids. FIG. 4H-I provide graphs of results of tests of functionality and toxicity levels of engineered set of UAGA and XYZZ suppressors. FIG. 4H shows results with UAGA quad codon. FIG. 4I shows results with XYZZ quad codon.

FIG. 5A illustrates elements of a construct that was designed for phage propagation reporter. FIG. 5B shows schematic of the reporter activity. FIG. 5C shows images of validation study results. FIG. 5D shows luminescence reporter readout trends with phage reporter with the graphs showing page enrichment versus % wild type luminescence.

FIG. 6A-F provides graphs and diagrams of results of experiments relating to continuous directed evolution of quadruplet decoding tRNAs. FIG. 6A shows results including graphs showing phage titers (left axis, solid lines) and population dilution rate (right axis, dashed lines). FIG. 6B provides bar graphs showing results indicating that phage plaquing improved with evolution. FIG. 6C provides diagrams showing sequences of certain evolved tRNA variants. Evolved tRNA variant Q-CAGG Evo1 is represented by SEQ ID NO: 98, Q-TAGA Evo1 by SEQ ID NO: 99, Q-TAGA Evo2 by SEQ ID NO: 100, Y-TAGA Evo by SEQ ID NO: 101, R-TAGA Evo1 by SEQ ID NO: 102, R-TAGA Evo2 by SEQ ID NO: 103, and R-TAGA Evo3 by SEQ ID NO: 104. FIG. 6D is a graph showing comparison of % efficiency of naïve versus evolved UAGA suppressors. FIG. 6E-F shows a schematic diagram and bar graph illustrating aspects of developed selection circuit that links activity to virus propagation and results of the selection. FIG. 6E provides diagram of frameshift and FIG. 6F provides bar graph showing phage titer results.

FIG. 7A-E provides graphs and diagrams of strategy and results of continues directed evolution of S-UAGA tRNA. FIG. 7A is a graph of results of continuous evolution of Serine-TAGA. FIG. 7B shows results indicating that plaquing of S-TAGA phage improved with evolution. FIG. 7C provides diagrams of sequences of evolved variants of the SerU-UAGA tRNA. WT tRNA SerU is represented by SEQ ID NO: 105. SEQ ID NO: 106 is the loop portion shown in the box labeled Naïve, SEQ ID NO: 107 is the loop portion shown in the boxes labeled Evolved 1 and Evolved 2, and SEQ ID NO: 108 is the loop portion shown in the box labeled Evolved 3. FIG. 7D provides a graph showing results of evolved serine suppressors indicating % translation efficiency resulting in the indicated tests. FIG. 7E provides a graph of results of crosstalk analysis of Serine Evolved 3.

FIG. 9A-C shows additional novel sequences encoding suppressor tRNA sequences. SEQ ID NOs: 28-97 are novel sequences that were identified using methods as described herein. FIG. 9A shows sequences (SEQ ID NOs: 28-67), each of which encodes either a minimally functional (<1% of WT activity) or functional (>1% of WT activity) suppressor tRNA. FIG. 9B shows (1) sequences encoding suppressor tRNAs that were either extremely toxic (SEQ ID Nos: 68-72) or (2) nonfunctional (<0% of WT activity; SEQ ID NOs: 73-87). FIG. 9B also shows 25 evolved tRNA encoding sequences that were identified (SEQ ID NOs: 88-97 and 131-145). Sequences in FIGS. 9A and 9B are naïve sequences, except for SEQ ID NOs: 88-97 and 131-145, all 25 of which are evolved sequences. FIG. 9C provides plasmid information for the sequences as indicated.

FIG. 11A is a schematic diagram showing luciferase reporter for quadruplet decoding. SEQ ID NOs:

109 is an amino acid sequence transcribed from the example sequence (SEQ ID NO: 110) in the absence of quadruplet decoding, whereas SEQ ID NO: 111 is an amino acid sequence transcribed in the presence of quadruplet decoding. FIG. 11B is a graph illustrating validation of luciferase reporter. FIG. 11C is a table of codon reassignment to TAGA. FIG. 11D is a table of codon reassignment based on original codon.

FIG. 12A-G provides graphs and tables illustrating a strategy for reporter development and rationally engineering quad tRNAs, also referred to herein as: qtRNAs. FIG. 12A shows result from inducible tRNA promoter. FIG. 12B shows results of luxAB residue 357 permissivity test. FIG. 12C shows graph of results of reporter stringency testing. FIG. 12D shows graph of results of a study examining % translation efficiency compared to triplet codon. FIG. 12E-G show % translation efficiency of various quadruplet codons.

FIG. 13A is a schematic diagram showing pIII selection for functional qtRNAs that decode a specific codon. FIG. 13B provides photos of results if pIII selection validation—plaquing methods. FIG. 13C provides a graph or results from pIII selection validation—enrichment. FIG. 13D is a schematic diagram showing selections performed with pIII reporter. FIG. 13E is a plot showing representative pIII selection results for AGGG reporter.

FIG. 14A-C provides a diagram and tables showing strategy for an M13-based library selection for efficient qtRNAs. FIG. 14A shows possible cheater quad codons. SEQ ID NOs: 112 and 113 show forward and reverse strands, respectively, of a reporter sequence comprising a quadruplet codon and encoding amino acid sequence SEQ ID NO: 114. FIG. 14B shows results of cross of library of tRNAs for every canonical amino acid with eight different M13-selection reporters. Fold enrichment or de-enrichment relative to the input phage titer for each selection is shown. FIG. 14C shows results of Sanger sequencing of two plaques to determine the anticodon identity.

FIG. 15A is a schematic diagram showing repeated application of pIII reporter results in continuous directed evolution. SEQ ID NOs: 115 and 116 show forward and reverse strands, respectively, of a reporter sequence comprising a quadruplet codon and encoding amino acid sequence SEQ ID NO: 117. FIG. 15B is a graph showing that the produced evolved qtRNAs are an order of magnitude more efficient versus their pre-evolved efficiencies. FIG. 15C illustrates that additional evolution on a harder goal resulted in further improvement.

FIG. 16A shows graphs of results of evolving five tRNA qtRNAs in continuous culture. FIG. 16B provides bar graphs showing comparison of initial and final tRNA variants against a ladder of phage activity reports of increasing difficulty ("med." is medium). FIG. 16C is a graph of results of continuous evolution of Serine-TAGA. WT tRNA SerU is represented by SEQ ID NO: 105. SEQ ID NO: 106 is the loop portion shown in first upper box, SEQ ID NO: 107 is the loop portion shown in the second and third upper boxes, and SEQ ID NO: 108 is the loop portion shown in the fourth upper box. FIG. 16D is a bar graph comparing initial and final qtRNA variants of S-TAGA against a ladder of phage activity reporters of increasing difficulty. FIG. 16E provides diagrams showing the sequences of the evolved qtRNAs from the experiments. Evolved tRNA variant Q-CAGG Evo1 is represented by SEQ ID NO: 98, Q-TAGA Evo1 by SEQ ID NO: 99, Q-TAGA Evo2 by SEQ ID NO: 100, Y-TAGA Evo by SEQ ID NO: 101, R-TAGA Evo1 by SEQ ID NO: 102, R-TAGA Evo2 by SEQ ID NO: 103, and W-TAGA Evo1 by SEQ ID NO: 118.

FIG. 17A shows a diagram of a pipeline for quantifying qtRNA charging. SEQ ID NO: 119 is an amino acid sequence from sfGFP wherein the second Y residue (open downward arrow) was provided using a qtRNA-TAGA scaffold. FIG. 17B shows mischarging evolution of W-TAGA. FIG. 17C provides an image showing analysis of W-TAGA identity elements, shown by SEQ ID NO: 120.

FIG. 18A-B illustrates data from experiments measuring crosstalk. FIG. 18A illustrates crosstalk profiles of evolved qtRNAs and shows results of measured crosstalk between evolved variants and fourth-base mismatch codons, or the amber stop codon. FIG. 18B shows results from assessing crosstalk between a set of five different qtRNAs and illustrates that qtRNAs are orthogonal. Values are in units of luminescence counts (AU); the induced tRNA is subtracted from the background suppressed tRNA value.

FIG. 19A provides a chart showing representative scaffolds for all 20 canonical amino acids can support four-base codon translation. FIG. 19B is a diagram illustrating translation of a linker entirely encoded with adjacent quadruplet codons. Experimental results showed that the evolved serine qtRNA can translate a linker of 5 adjacent quadruplet codons inserted at luxAB-357 and the efficiency of translation scales exponentially with length. FIG. 19C shows methods using a three plasmid system to perform translation through the orthogonal ribosome and constructs for utilizing qtRNAs together with an orthogonal ribosome. SEQ ID NO: 122 is an example sequence comprising two quadruplet codons and encoding the example amino acid sequence of SEQ ID NO: 121. FIG. 19D is a graph illustrating luciferase reporter translation through orthogonal ribosome and shows experimental results indicating that evolved qtRNAs can be used to suppress multiple quadruplet codons during translation through the orthogonal ribosome. Expression of the orthogonal-rRNA (O-rRNA) and qtRNA results in translation of a luciferase. Positive control is a WT luxAB encoded entirely with triplet codons.

FIG. 20A shows results of test of efficiency impact of encoding two quadruplet adjacent to one another in contrast to separation from each other by one or more triplet codons. FIG. 20B shows reporter design strategy used in some studies. FIG. 20B top box shows zero triplet codons in between the two quadruplets (shown in capital letters in sequence); second box from top shows one triplet codon in between the two quadruplets (shown in capital letters in sequence); third box from top shows two triplet codons in between the two quadruplets (shown in capital letters in sequence); and fourth box from top shows three triplet codons in between the two quadruplets (shown in capital letters in sequence). FIG. 20B shows examples of reporter designs used in certain adjacency tests and encoded by SEQ ID NOs: 123-130.

BRIEF DESCRIPTION OF CERTAIN SEQUENCES

Figure 4A:
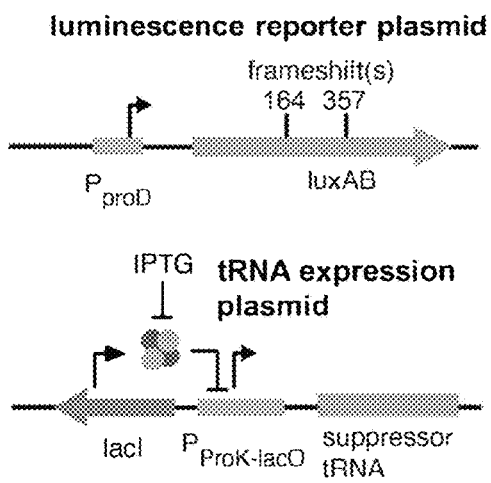

SEQ ID NO: 1-15 shown in FIG. 1.
SEQ ID NO: 16-21 shown in FIG. 2.
SEQ ID NO: 22 and 23 shown in FIG. 1.
SEQ ID NO: 24 shown in FIG. 2.

```
SEQ ID NO: 25: ProK-lacO promoter Sequence (lacO
site shown in uppercase letters):
tgtgcttctcaaatgcctgaggccagtttgctcaggctctccccgtggag
gtaataattgacgatatgatcagtgcacggctaactaagcggcctgctga
ctttctcgccgatcaaaaggcattttgctattaagggattgacgagggcg
tatctgcgcagtaagatAATTGTGAGCGGATAACAATT.

SEQ ID NO: 26: encodes xLuxAB sequence [which is
also referred to herein as LuxAB, see Nat Chem
Biol. 2014 March; 10(3): 216-222)]:
atgaaatttggaaactattgcttacataccaacctccccaattacccaaa
cagaggtaatgaaacgtttggttaaattaggtcgcatctctgaggagtgt
ggttttgataccgtatggttactggagcatcatttcacggagtttggttt
gcttggtaacccttatgtcgctgctgcatatttacttggcgcgactaaaa
aattgaatgtaggaactgccgctattgttcttcccacagcccatccagta
cgccaacttgaagatgtgaatttattggatcaaatgtcaaaaggacgatt
tcggtaggtatttgccgagggctttacaacaaggactttcgcgtattcgg
aacagatatgaataacagtcgcgccttagcggaatgctggtacgggctga
taaagaatggcatgacagagggatatatggaagctgataatgaacatatc
aagttccataaggtaaaagtaaaccccgcggcgtatagcagaggtggcgc
accggtttatgtggtggctgaatcagcttcgacgactgagtgggctgctc
aatttggcctaccgatgatattaagttggattataaatactaacgaaaag
aaagcacaacttgagctttataatgaagtggctcaagaatatgggcacga
tattcataatatcgaccattgcttatcatatataacatctgtagatcatg
actcaattaaagcgaaagagatttgccggaaatttctggggcattggtat
gattcttatgtgaatgctacgactattttttgatgattcagaccaaacaag
aggttatgatttcaataaagggcagtggcgtgactttgtattaaaaggac
ataaagatactaatcgccgtattgattacagttacgaaatcaatcccgtg
ggaacgccgcaggaatgtattgacataattcaaaaagacattgatgctac
aggaatatcaaatatttgttgtggatttgaagctaatggaacagtagacg
aaattattgcttccatgaagctcttccagtctgatgtcatgccatttctt
aaagaaaaacaacgttcgctattatattggcggtggcggtagcggcgg
tggcggtagcggcggtggcggtagcggcggtggcggtagcaaatttggat
tgttcttccttaacttcatcaattcaacaactgttcaagaacagagtata
gttcgcatgcaggaaataacggagtatgttgataagttgaattttgaaca
gattttagtgtatgaaaatcattttcagataatggtgttgtcggcgctc
ctctgactgtttctggttttctgctcggtttaacagagaaaatttaaaatt
ggttcattaaatcacatcattacaactcatcatcctgtccgcatagcgga
ggaagcttgcttattggatcagttaagtgaagggagatttatttttagggt
ttagtgattgcgaaaaaaagatgaaatgcattttttttaatcgcccggtt
gaatatcaacagcaactatttgaagagtgttatgaaatcattaacgatgc
tttaacaacaggctattgtaatccagataacgattttttatagcttccct
aaatatctgtaaatccccatgcttatacgccaggcggacctcggaaata
gtaacagcaaccagtcatcatattgttgagtgggcggccaaaaaaggta
tcctctcatctttaagtgggatgattctaatgatgttagatatgaatatg
ctgaaagatataaagccgttgcggataaatatgacgttgacctatcaga
atagaccatcagttaatgatattagttaactataacgaagatagtaataa
agctaaacaagagacgcgtgcatttattagtgattatgttcttgaaatgc
accctaatgaaatttcgaaaataaacttgaagaaataattgcagaaaac
gctgtcggaaattatacggagtgtataactgcggctaagttggcaattga
aaagtgtggtgcgaaaagtgtattgctgtcctttgaaccaatgaatgatt
tgatgagccaaaaaaatgtaatcaatattgttgatgataatattaagaag
taccacacggaatatacctaa.

SEQ ID NO: 27 encodes a modified xluxAB sequence
(UAGA reporter at residue 357, shown in uppercase
letters):
atgaaatttggaaactattgcttacataccaacctccccaattacccaaa
cagaggtaatgaaacgtttggttaaattaggtcgcatctctgaggagtgt
ggttttgataccgtatggttactggagcatcatttcacggagtttggttt
gcttggtaacccttatgtcgctgctgcatatttacttggcgcgactaaaa
aattgaatgtaggaactgccgctattgttcttcccacagcccatccagta
cgccaacttgaagatgtgaatttattggatcaaatgtcaaaaggacgatt
tcggtaggtatttgccgagggctttacaacaaggactttcgcgtattcgg
aacagatatgaataacagtcgcgccttagcggaatgctggtacgggctga
taaagaatggcatgacagagggatatatggaagctgataatgaacatatc
aagttccataaggtaaaagtaaaccccgcggcgtatagcagaggtggcgc
accggtttatgtggtggctgaatcagcttcgacgactgagtgggctgctc
aatttggcctaccgatgatattaagttggattataaatactaacgaaaag
aaagcacaacttgagctttataatgaagtggctcaagaatatgggcacga
tattcataatatcgaccattgcttatcatatataacatctgtagatcatg
actcaattaaagcgaaagagatttgccggaaatttctggggcattggtat
gattcttatgtgaatgctacgactattttttgatgattcagaccaaacaag
aggttatgatttcaataaagggcagtggcgtgactttgtattaaaaggac
ataaagatactaatcgccgtattgattacagttacgaaatcaatcccgtg
ggaacgccgcaggaatgtattgacataattcaaaaagacattgatgctac
aggaatatcaaatatttgttgtggatttgaagctaatggaacagtagacg
aaattattgcttccatgaagctcttccagtctgatgtcatgccatttctt
aaagaaaaacaacgtTAGActattatattatggcggtggcggtagcggcg
gtggcggtagcggcggtggcggtagcggcggtggcggtagcaaatttgga
ttgttcttccttaacttcatcaattcaacaactgttcaagaacagagtat
agttcgcatgcaggaaataacggagtatgttgataagttgaattttgaac
agattttagtgtatgaaaatcattttcagataatggtgttgtcggcgct
cctctgactgtttctggttttctgctcggtttaacagagaaaattaaaat
tggttcattaaatcacatcattacaactcatcatcctgtccgcatagcgg
aggaagcttgcttattggatcagttaagtgaagggagatttatttttaggg
tttagtgattgcgaaaaaaagatgaaatgcatttttttaatcgcccggt
tgaatatcaacagcaactatttgaagagtgttatgaaatcattaacgatg
ctttaacaacaggctattgtaatccagataacgattttttatagcttccct
aaaatatctgtaaatccccatgcttatacgccaggcggacctcggaaata
tgtaacagcaaccagtcatcatattgttgagtgggcggccaaaaaaggta
ttcctctcatctttaagtgggatgattctaatgatgttagatatgaatat
gctgaaagatataaagccgttgcggataaatatgacgttgacctatcaga
gatagaccatcagttaatgatattagttaactataacgaagatagtaata
aagctaaacaagagacgcgtgcatttattagtgattatgttcttgaaatg
caccctaatgaaatttcgaaaataaacttgaagaaataattgcagaaaa
cgctgtcggaaattatacggagtgtataactgcggctaagttggcaattg
aaaagtgtggtgcgaaaagtgtattgctgtcctttgaaccaatgaatgat
ttgatgagccaaaaaaatgtaatcaatattgttgatgataatattaagaa
gtaccacacggaatatacctaa.
```

SEQ ID NOs: 28-67 shown in FIG. 9A.
SEQ ID Nos: 68-97 and 131-145 shown in FIG. 9B.

DETAILED DESCRIPTION

The invention, in part, includes novel suppressor tRNA molecules and methods of using same. The invention also includes reporters and assays with which to verify function of designed suppressor tRNA molecules, and the invention, in part includes methods to identify, design, and evolve efficient and effective suppressor tRNA molecules, which are also referred to herein as "tRNA suppressor molecules."

To explore the feasibility of efficient quadruplet codon translation, studies were undertaken to engineer quadruplet decoding tRNA variants for every *E. coli* tRNA. To identify starting points, known suppressors were tested, and a number of rationally engineered suppressors using two different codon reassignment strategies were prepared and tested. To improve upon the resulting minimally functional quadruplet decoding tRNAs, aspects of the invention included use of rapid continuous directed evolution methods to evolve suppressors with improved quadruplet decoding efficiency for different tRNA scaffolds and different quadruplet codons. In every case, tRNA variants arose that exhibited substantial improvements in quadruplet decoding. The most efficient of the suppressors that were evolved using methods of the invention was determined to be capable of efficiently translating a protein that contained four frameshifts.

The invention, in part, includes quadruplet decoding tRNAs based on a representative *E. coli* tRNA scaffold for each of the 20 canonical amino acids. Information disclosed herein demonstrates that any tRNA can be converted to decode a four-base codon. Although quadruplet codon translation is generally much less efficient than triplet codon translation, directed evolution of the quadruplet tRNAs can result in substantial improvements. Many quadruplet tRNAs continue to be selectively charged by the cognate amino acid of the parent scaffold. Results of studies such as those disclosed herein indicate feasibility of creating a synthetic genetic code based entirely on quadruplet codons.

Embodiments of methods of the invention were used to prepare a catalog of 63 novel naïve suppressors, which constitute the most comprehensive effort to engineer quadruplet decoding tRNAs to date. Methods of the invention were also used to determine that the anticodon loop sides frequently contributed to improved quadruplet decoding, and to demonstrate the extent to which codon size was controlled at the tRNA level. Embodiments of methods of the invention have been used to confirm that the ready access to higher activity variants that decode quadruplet codons in multiple contexts reveals inherent three-versus four-base promiscuity in translation machinery. Thus, methods of the invention offer a tractable strategy for genetic code expansion. As used herein the terms: "quad" and "quadruplet" may be used interchangeably. Quad tRNAs are also referred to herein qtRNAs herein and are named as "amino acid identity of tRNA scaffold-codon"; for example a serine tRNA with the 5'-TCTA-3' anticodon is referred to as "S-TAGA".

Methods of the invention include a novel strategy to overcome codon conflict by implementing an orthogonal translation apparatus in E. coli that exclusively and unambiguously translates four-base-codons, and cannot translate triplet codons. This apparatus requires a full complement of tRNAs that decode canonical amino acids using four-base codons. Methods of the invention have been used to prepare exclusive quadruplet-codon translation by engineering quadruplet-tRNAs for all of the 20 canonical amino acids. In these methods, the anticodon was manipulated in a representative E. coli tRNA scaffold corresponding to each of the 20 canonical amino acids and it was determined that all 20 can support four-base translation. Methods of the invention also include application of directed evolution to optimize the tRNA scaffold to contain the new anticodon. Mutations to the bases flanking the anticodon significantly improved quadruplet codon translation efficiency, usually with minimal impact on amino acid charging fidelity. It has now been shown that these engineered tRNAs can be used together with an orthogonal ribosome to translate a protein containing quadruplet codons. These results suggest that a dedicated quadruplet-codon translation apparatus as a feasible approach for genetic code expansion. See Rackham, O. & Chin, J. Nat Chem Biol 1, 159-166 (2005) for additional information on orthogonal RNAs.

Certain embodiments of methods of the invention were designed to be used to compare different suppressor tRNAs. Thus, some embodiments of the invention include a quantification technique that was designed to be capable of independently quantifying toxicity and quadruplet decoding efficiency. In certain embodiments of the invention reporter assays are provided. Certain embodiments of reporter assays of the invention can be used for one or more of reporting and quantifying toxicity and quadruplet decoding efficiency. Methods of the invention may include use of a frameshift-dependent bacterial luciferase reporter, which in some embodiments is prepared by integrating a quadruplet codon within xluxAB [xLuxAB is version of LuxAB that is covalently linked with short (GGGGS)4 linker, (see Nat Chem Biol. 2014 March; 10(3): 216-222), the sequence of xLuxAB that encodes the polypeptide, is set forth as SEQ ID NO: 26]. Failure to decode this codon leads to premature termination, versus in the event of successful frameshift suppression—luminescence results. In some embodiments of the reporter assay, luciferases are used. Luciferases are catalytic and do not experience maturation lag, which allows them to act as fast reporters that are especially sensitive in the low-activity range. Certain embodiments of the invention comprise a two-plasmid reporter system in which a suppressor tRNA is inducibly expressed from one plasmid and luciferase transcript is constitutively expressed from a second plasmid. In order to robustly compare toxic and non-toxic tRNAs in certain embodiments of the invention, luminescence measurements were measured kinetically, and internally standardized to the growth rate of the host bacteria. The reporter of the invention was validated using a previously reported engineered suppressor, and results confirmed that luminescence relied on codon-anticodon interactions and the presence of a quadruplet decoding tRNA, thus validating the reporter and methods of its use in assays such as those set forth herein. In a non-limiting example, certain embodiments of reporter assays of the invention have been used to identify that certain sequences encode "suppressors" that are one or both of toxic and lacking function, such as SEQ ID NOs: 68-87 set forth in FIG. 9B.

Additional aspects of the invention include designing and confirming methods of comprehensively engineering quadruplet decoding tRNAs through rational design and directed evolution. Methods of the invention in part, included identifying suppressor tRNAs' naturally occurring E. coli scaffolds, and methods of evolving these and other minimally functional suppressor tRNAs and improving their efficiency to decode quadruplet codons. Certain aspects of the invention also comprise a bacteriophage-based continuous directed evolution methods for use in methods of evolving translation components for improved quadruplet decoding translation. Use of such methods of the invention have at least several benefits. One, the use of phage activity reporters containing frameshifts in multiple locations reduced the risk of evolving transcript sequence-context specific cheaters. Also, it was identified that several evolved variants exhibit stem-recoding, confirming that this method is capable of evolving functional RNA that depends on secondary structure. Finally, certain embodiments of methods of the invention can be used to avoid the requirement of discrete library creation and screen steps. Methods of the invention can be used for tRNA evolution, and have shown they can be used to prepare suppressor tRNA variants with substantially improved quadruplet decoding efficiency.

Suppressor tRNAs of the invention and their encoding sequences can be used to translate a single DNA sequence that contains a quadruplet codon or codons into several distinct protein products by manipulating the presence of suppressor tRNAs rather than the DNA sequence. Methods of using suppressor tRNAs of the invention and their encoding sequences in include, but are not limited to preparing molecular sensors, circuits, and reporters. Prior methods used in genetic code expansion suffer from low incorporation efficiency and impure translated protein products due to promiscuity between triplet and quadruplet codon codes. Suppressor tRNAs of the invention can be used as the basis for encoding canonical amino acids in an exclusively quadruplet codon code, eliminating crosstalk between canonical and expanded genetic code and enabling high-fidelity all-quadruplet protein translation. Use of suppressor tRNAs of their encoding molecules permits expansion to an exclusively-quadruplet codon code and thus makes available an additional 235 free codons that can be assigned to non-canonical amino acids using additional exogenous tRNA/aminoacyl-tRNA synthetase (aaRS) pairs.

Transfer RNA (tRNA)

The terms "transfer RNA" or tRNA as used herein refer to a small RNA chain that transfers a specific amino acid to a growing peptide chain at the ribosomal site of protein synthesis during translation. A tRNA has a 3' terminal site for amino acid attachment. This covalent linkage is catalyzed by an aminoacyl tRNA synthetase. The tRNA also comprises a three-base region called the anticodon that can base-pair to the corresponding three base codon region on mRNA. In certain embodiments of the invention, a tRNA is a suppressor tRNA.

Four Base Codon Code and Suppressor tRNAs and Variants Thereof

The canonical genetic code uses three-base codons to encode proteins containing the 20 canonical amino acids. Synthetic biologists have proposed switching over to a four-base codon code, which could accommodate up to 255 different amino acids. This could enable addition of up to 235 non-canonical amino acids (NCAAs), which have been shown to be useful for creating protein therapeutics with enhanced properties. Achieving this system requires a complete set of tRNAs that incorporate the 20 canonical amino acids using four base codons ("Frameshift suppressors"). Existing frameshift suppressors were inefficient and incomplete and new frameshift suppressors are provided herein that have been prepared and tested.

A suppressor tRNA, also referred herein as a "frameshift suppressor" is a tRNA with a sequence element in the anticodon that allows it to recognize a stop codon and insert an amino acid in its place. Embodiments of the invention comprise use of suppressors having four-base codons. Generally, four-base (or Quadruplet) suppressor tRNAs have an expanded anticodon loop that is not a substrate for an endogenous synthetase and it decodes a quadruplet versus triplet codon. The four-base codon does not code for one of the natural amino acids.

A suppressor tRNA is a tRNA that alters the reading of a messenger RNA (mRNA) in a given translation system, for instance, by providing a mechanism for incorporating an amino acid into a peptide chain in response to a selector codon. For example, a suppressor tRNA of the invention can read a four-base codon. Exemplary modified suppressor tRNAs are provided herein including those encoded by sequences set forth as SEQ ID NOs: 1-21, 28-67, 88-97, and 131-145.

In some embodiments of the invention, a suppressor tRNA molecule is a variant of a suppressor tRNA molecule disclosed herein. In a non-limiting example, a variant suppressor tRNA of the invention may be a fragment, homolog, or fusion sequence that retains an ability to transfer the amino acid cysteine to a growing polypeptide chain. In certain embodiments of the invention, a variant of a suppressor tRNA molecule has at least 80%, 81%, 82%, 83%, 84%, 85%, 86%, 87%, 88%, 89%, 90%, 91%, 92%, 93%, 94%, 95%, 96%, 97%, 98%, or 99% identity to the sequence of a suppressor tRNA molecule set forth herein, which may also be referred to herein as the "parent" sequence of its variant. In variants of a sequence encoding a tRNA molecule set forth here, the anticodons are not varied from the parent to the variant. In certain embodiments of the invention, a variant of a sequence encoding a suppressor tRNA molecule has at least 80%, 81%, 82%, 83%, 84%, 85%, 86%, 87%, 88%, 89%, 90%, 91%, 92%, 93%, 94%, 95%, 96%, 97%, 98%, or 99% identity to the sequence of the sequence encoding a suppressor tRNA molecule set forth herein, which may also be referred to herein as the "parent" sequence of its variant.

In some embodiments of the invention, a nucleic acid molecule encoding a suppressor tRNA molecule is a variant of a suppressor tRNA encoding molecule disclosed herein. In a non-limiting example, a variant suppressor tRNA encoding molecule of the invention may be a fragment, homolog, or fusion sequence that retains an ability encode a tRNA that is able to transfer the amino acid cysteine to a growing polypeptide chain. In certain embodiments of the invention, a variant of a suppressor tRNA-encoding molecule has at least 80%, 81%, 82%, 83%, 84%, 85%, 86%, 87%, 88%, 89%, 90%, 91%, 92%, 93%, 94%, 95%, 96%, 97%, 98%, or 99% identity to the sequence of a suppressor tRNA-encoding molecule set forth herein, which may also be referred to herein as the "parent" sequence of its variant. In variants of a sequence encoding a tRNA molecule set forth here, the anticodons are not varied from the parent to the variant. In certain embodiments of the invention, a variant of a sequence encoding a suppressor tRNA molecule has at least 80%, 81%, 82%, 83%, 84%, 85%, 86%, 87%, 88%, 89%, 90%, 91%, 92%, 93%, 94%, 95%, 96%, 97%, 98%, or 99% identity to the sequence of the sequence encoding a suppressor tRNA molecule set forth herein, which may also be referred to herein as the "parent" sequence of its variant.

tRNA Structure and Anticodons

Transfer RNA has a primary structure, a secondary structure (referred to as a cloverleaf structure), and a tertiary structure (an L-shaped three-dimensional structure that allows the tRNA to fit into appropriate sites of the ribosome). In a quadruplet suppressor tRNA an anticodon is a unit made up of four nucleotides that correspond to the four bases of the mRNA codon. Each quad tRNA contains a specific anticodon quad sequence that can base-pair to one or more quad codons for an amino acid. For example, one quadruplet codon for lysine is UCUA; the anticodon tRNA might be TAGA.

Suppressor tRNA Molecules

Some embodiments of the invention include compositions that include a suppressor tRNA molecule encoded by a sequence set forth as one of SEQ ID NOs: 1-21, 28-67, 88-97, and 131-145. A composition may include one or more independently selected suppressor tRNA-encoding sequences and a composition of the invention may include one or more suppressor tRNAs of the invention. In certain embodiments, a composition comprising a suppressor tRNA or its encoding sequence may also include a detectable label. In some embodiments, the suppressor tRNA, or its encoding sequence comprises a detectable label. Non-limiting examples of detectable label polypeptides that may be included in a composition of the invention fluorescent labels, luminescent labels, or other suitable detectable art-known labels.

In some embodiments of the invention, a sequence encoding a suppressor tRNA of the invention, for example a sequence set forth as one of: SEQ ID NOs: 1-21, 28-67, 88-97, and 131-145, is included in a vector. In certain embodiments more than one encoding sequence may be included in the vector. A vector used to generate a suppressor tRNA may also include a promoter sequence. A non-limiting example of a promoter that may be included is a PproK-lacO promoter sequence, or a functional variant thereof. A PproK-lacO promoter sequence is set forth herein as SEQ ID NO: 25. A skilled artisan will recognize other promoters suitable for use in a vector used in an embodiment of the invention.

LuxAB Reporter

According to another aspect of the invention, compositions are provided that include a variant LuxAB reporter molecule encoded with an independently selected quadruplet codon at one or more residues of a LuxAB protein sequence. The LuxAB reporter protein sequence is encoded by the sequence set forth as SEQ ID NO: 26. In certain embodiments, the variant LuxAB reporter molecule is encoded by a Lux reporter molecule that also includes an independently selected quadruplet codon at one or both of residue 164 and residue 357 of the LuxAB protein sequence. SEQ ID NO: 27 is an example of a variant LuxAB reporter molecule that includes the sequence set forth as SEQ ID NO: 26 with inclusion of a quadruplet codon at residue corresponding to 357 of expressed Lux. In some aspects of the invention an assay method is provided, the method comprising any embodiment of an aforementioned variant LuxAB composition.

Vectors/Promoters/Engineering Elements

Various vectors, cells, and other elements are used in certain embodiments of methods and compositions of the invention. As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert a mutant light-activated ion channel polypeptides and variants thereof of the invention, into dividing and non-dividing cells and can insert mutant light-activated ion channel polypeptides and variants thereof of the invention to cells that are in vivo, in vitro, or ex vivo cells. The terms: "protein" and "polypeptide" may be used interchangeably herein.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein. In certain embodiments of the invention, a vector may be a lentivirus comprising the gene for a mutant light-activated ion channel or variant thereof of the invention. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a mutant light-activated ion channel polypeptide or variant thereof in a wide variety of cell types—thus a promoter for a gene that is widely expressed in a variety of cell types, for example a "housekeeping gene" can be used to express a mutant light-activated ion channel polypeptide, or variant thereof, in a variety of cell types. Non-limiting examples of general promoters are provided elsewhere herein and suitable alternative promoters are well known in the art.

In certain embodiments of the invention, a promoter may be an inducible promoter, examples of which include, but are not limited to a PproK-lacO promoter, as described herein.

Engineering Evolved Suppressor tRNAs

Methods of the invention also include engineering evolved quadruplet decoding suppressor tRNAs. Engineering methods of the invention include, in some embodiments, engineering an evolved quadruplet decoding suppressor tRNA from a preselected quadruplet decoding suppressor tRNA. In certain embodiments of the invention a method of evolving quadruplet decoding suppressor tRNA include a phage-assisted continuing evolution (PACE) method, which in certain embodiments of the invention, is a bacteriophage-based directed evolution method. In some embodiments of the invention a method of evolving suppressor tRNAs includes a means of determining the presence of a successfully evolved quadruplet decoding suppressor tRNA. A non-limiting example of a means for determining the presence of the successfully evolved quadruplet decoding suppressor tRNA includes detecting a phage propagation reporter, wherein successful quadruplet decoding by the evolved suppressor tRNA results in phage propagation. Examples of the preparation and use of phage propagation reporter are provide elsewhere herein, including in the Examples section and Figures. In certain embodiments of the invention, a means for determining the presence of the successful evolved quadruplet decoding suppressor tRNA includes: (a) challenging (i) an essential phage protein encoded with one or more quadruplet codons and (ii) an evolved quadruplet decoding suppressor tRNA encoded on a phage from which the essential phage protein has been deleted, to infect a plurality of *E. coli*. The challenging may then be followed by detecting a functional phage produced in the challenged *E. coli*, wherein the functional phage produced indicates the presence of one or more successful quadruplet decoding(s) by the evolved quadruplet decoding suppressor tRNA. In some embodiments, the essential phage protein is a pIII phage protein.

Methods of the invention include in some embodiments, Phage Assisted Continuous Evolution (PACE). PACE methods may be used in methods of the invention which to evolve a suppressor tRNA. In one embodiment, a sample to be evolved may include one or more suppressor tRNA molecules of interest to evolve. A sample in a receptacle in a system or method of the invention may also include one or more of a cell, fluid, an inducer, and other components appropriate for PACE methods. Additional general and specific examples of components that may be included in samples are provided elsewhere herein and additional art-known molecules are suitable to include in samples in embodiments of systems and methods of the invention. For additional details regarding PACE set up and use that can be used in conjunction with methods of the invention, see: Esvelt, K. M., et al., *Nature* 472, 499-503 (2011); Bryson, D. I., et al., (2017). Nat. Chem. Biol. December; 13(12):1253-1260; Packer, M. S., et al., *Nat. Commun.* 8, 956 (2017); Dickinson, B. C., et al., *Nat. Commun.* 5, 5352 (2014); Wang, T., et al., *Nat. Chem. Biol.* 14, 972-980 (2018); Zinkus-Boltz, J. & Dickinson, B. C. *Nat. Chem. Biol.* 13, 432-438 (2017); and Hu, J. H., et al., (2018). Nature April 5; 556(7699):57-63. Nature April 5; 556(7699):57-63. Nature April 5; 556(7699):57-63, each of which is incorporated herein in its entirety by reference].

Samples and Cells

Cells included in certain embodiments of systems and methods of the invention may be interchangeably referred to herein as "cells" or "host cells." In certain embodiments of the invention, a host cell is a bacterial cell, a non-limiting example of which is a bacterial cell that can be infected with M13. Continuous evolution procedures in embodiments of systems and methods of the invention comprise F+ bacteria that are amenable to M13 infection. As is understood in the art, F+ bacteria possess F factor as a plasmid independent of the bacterial genome. A non-limiting example of a host cell that is used in some embodiments of methods and systems of the invention is an *E. coli* cell. Additional bacterial cells that are amenable to M13 infection are known in the art and are suitable for use in methods and systems of the invention. Bacteria can be used as cells and host cells in certain embodiments of the invention, including but not limited to embodiments comprising use of phage-assisted continuous evolution (PACE) methods. Additional information about and examples of bacteria suitable for use in methods and systems of the invention are known in the art, see for example, U.S. Pat. No. 9,394,537, the teaching of which is incorporated by reference herein in its entirety. It will be understood that in certain embodiments of the invention cells may include non-PACE methods and in such embodiments cells other than bacterial cells may be used. For example though not intended to be limiting, in some embodiments of the invention, non-bacterial cells can be used in other types of continuous directed evolution and tRNAs evolved using a similar approach to that disclosed herein. See for example, for yeast [Ravikumar, A. et al, (2014) Nature Chemical Biology, Vol. 10, March 2014, 175-177 and online methods: doi:10.1038/nchembio.143]) and mammalian cells (English, J. G. et al. (2019), Cell Vol. 178, 748-761, Jul. 25, 2019 and online methods). In some embodiments of the invention a cell is a eukaryotic cell. In some embodiments of the invention a cell is an invertebrate cell. In some embodiments of the invention, a cell is a vertebrate cell. In certain embodiments of the invention, a cell is an engineered cell, and is not a naturally occurring cell.

A host cell included in a system or method of the invention may be a cell comprising a horizontally transferable nucleic acid. In some embodiments, a host cell is provided that comprises at least one viral gene encoding a protein required for the generation of infectious viral particles under the control of a conditional promoter. As a non-limiting example, a host cell may comprise an accessory plasmid comprising a gene required for the generation of infectious phage particles, for example, M13 gIII, wherein the required gene is under the control of a conditional promoter, as described elsewhere herein. In some embodiments of the invention a conditional promoter is inserted into the genome of a host cell, wherein the genome of the host cell also includes a gene required to produce infectious viral particles.

Continued directed evolution systems and methods of the invention may include use of a phage, a viral vector, or naked DNA (e.g., a mobilization plasmid) for delivery or transfer of a gene of interest into a cell, or between cells, respectively. Transfer of a gene of interest from one host cell to a second host cell may be accomplished in a number of ways. For example, though not intended to be limiting, a transfer may occur using a transfer vector that is a virus that infects a cell, such as, but not limited to a bacteriophage or a retroviral vector. In certain embodiments, a viral vector is a phage vector that infects bacterial host cells. In certain embodiments of continuous evolution methods, a transfer vector is a conjugative plasmid transferred from one bacterial cell to a second bacterial cell. It will be understood that in some aspects of the invention, transfer of a gene of interest from one cell to a second cell is dependent on an activity of the gene of interest.

Protein Production

In some embodiments of the invention, suppressor tRNAs of the invention and/or their encoding sequences can be used in methods to prepare a plurality of different proteins from the same DNA sequence. As used herein the term "plurality" means more than one, for example, at least: 2, 3, 4, 5, 6, 7, 8, 9 10, or more. Certain embodiments of methods of the invention include using a plurality of different suppressor tRNA sequences to decode the same DNA sequence. In this way, the sequence of each of the plurality of suppressor tRNA may decode the DNA sequence, thereby directing translation of the DNA sequence. The different decoding of the DNA sequence by the plurality of suppressor tRNAs, produces a plurality of different protein products. Certain embodiments of the invention include a composition comprising a plurality of selected suppressor tRNAs of the invention that are expressed and decode DNA sequences also present in the composition. It will be understood that embodiments of methods of the invention may be carried out under conditions suitable for one or more of: tRNA expression, decoding, and translation.

Methods to prepare multiple different proteins from the same DNA are possible because different suppressor tRNA molecules of the invention result in different translated protein products. In a non-limiting example, a method of the invention may include preparing a DNA sequence that includes a quadruplet codon encoding one or more amino acids, decoding the quadruplet codon with a suppressor tRNA of the invention, for example, a tRNA encoded by a sequence set forth as any one of SEQ ID NOs: 1-21, 28-67, 88-97, and 131-145. Following the decoding, the DNA sequence is translated to produce a protein comprising the encoded amino acids. In some embodiments, the protein product that is produced includes both triplet and quadruplet codons, and in certain embodiments of methods of the invention, the protein translation is an all-quadruplet protein translation.

In another non-limiting example, a method of the invention includes translating a single DNA sequence into one or more distinct protein products. In such methods, if one suppressor tRNA of the invention is used, the single DNA sequence will be translated into one distinct protein product. If a plurality of suppressor tRNAs of the invention are used to translate a single DNA sequence, the single DNA sequence may be translated into a plurality of protein products. Examples of suppressor tRNAs that may be used in methods of the invention include, but are not limited to suppressor tRNAs encoded by one of SEQ ID NOs: 1-21, 28-68, 88-97, and 131-145. The specific suppressor tRNA(s) expressed determine the amino acids sequence of proteins produced by translating the DNA sequence.

It will be understood that methods of the invention that include expressing tRNAs, decoding DNA sequences, and translating DNA sequences are performed under suitable conditions for the expression, decoding, and translation, respectively. Conditions suitable for expression, decoding, and translation are described herein and additional art-known conditions may be used. In some embodiments of the invention, the decoding is performed in a cell, which may be, for example, though not intended to be limiting, a bacterial cell, an invertebrate cell, a plant cell, a yeast cell, a vertebrate cell, or other suitable cell type. It will be understood that in some embodiments the decoding is performed in a non-natural, or engineered cell. Certain methods of the invention also include assessing a protein produced for characteristics such as, but not limited to: function of the protein produced and the structure of the protein product produced. Means to assess protein characteristics, non-limiting examples of which are: structure, function, stability, etc. are well known and routinely practiced in the art, and can be used to assess proteins produced using methods of the invention. In some embodiments of methods of the invention for translating a DNA sequence, the protein product includes both triplet and quadruplet codons, and in certain embodiments of methods of the invention, the protein product is an all-quadruplet protein translation.

EXAMPLES

Example 1-8

Examples 1-8 describe experiments and studies performed to produce and test engineered tRNAs that support quadruplet codon translation. From the studies sequences encoding suppressors were generated and tested, and included sequences set forth herein as: SEQ ID NOs: 1-21, for sequences see FIG. 1 and FIG. 2. SEQ ID NOs: 1-15 are non-evolved and SEQ ID NOs: 16-21 are evolved sequences.

General Materials and Methods for Examples 1-8.
Materials

Antibiotics (Gold Biotechnology) were used at the following working concentrations: carbenicillin, 50 µg/mL; spectinomycin, 100 µg/mL; chloramphenicol, 40 µg/mL; kanamycin, 30 µg/mL; tetracycline, 10 µg/mL; streptomycin, 50 µg/mL. Water was purified using a MilliQ puri cation system (Millipore). Phusion U Hot Start DNA polymerase (Thermo Fisher Scientific) was used for all PCRs. Plasmids and bacteriophage were cloned by USER assembly. tRNA genes were amplified directly from E. coli genomic DNA. Plasmids were cloned and amplified using either Mach1 (Thermo Fisher Scientific) or Turbo (New England BioLabs) cells. Unless otherwise noted, plasmid or bacteriophage DNA was amplified using the Illustra TempliPhi 100 Amplification Kit (GE Healthcare Life Sciences) before Sanger sequencing. Information is provided in FIG. 9C about plasmids used in certain embodiments of the invention.

Preparation and Transformation of Chemically Competent Cells

Strain S2060 was used in all luciferase, phage propagation, and plaque assays, as well as in all PACE experiments. To prepare competent cells, an overnight culture was diluted 1,000-fold into 50 mL of 2×YT media (United States Biologicals) supplemented with appropriate antibiotics and grown at 37° C. with shaking at 230 r.p.m. to OD600 ~0.4-0.6. Cells were pelleted by centrifugation at 6,000 g for 10 min at 4° C. The cell pellet was then resuspended by gentle stirring in 5 mL of TSS (LB media supplemented with 5% v/v DMSO, 10% w/v PEG 3350, and 20 mM $MgCl_2$). The cell suspension was stirred to mix completely, aliquoted and frozen on dry ice, and stored at −80° C. until use. To transform cells, 100 µL of competent cells thawed on ice. To this, plasmid (2 µL each; up to two plasmids per transformation) and 100 µL KCM solution (100 mM KCl, 30 mM $CaCl_2$, and 50 mM $MgCl_2$ in $H_2O$) were added and stirred gently with a pipette tip. The mixture was incubated on ice for 10 min and heat shocked at 42° C. for 90 s before 850 µL of 2×YT media was added. Cells were allowed to recover at 37° C. with shaking at 230 r.p.m. for 0.75 h, streaked on 2×YT media+1.5% agar (United States Biologicals) plates containing the appropriate antibiotics, and incubated at 37° C. for 16-18 h.

Kinetic Luminescence Assay

S2060 cells were transformed with the luciferase-based activity reporter and tRNA expression plasmids of interest as described above. Overnight cultures of single colonies grown in DRM media supplemented with maintenance antibiotics were diluted 500-fold into DRM media with maintenance antibiotics in a 96-well deep well plate, with or without IPTG inducer. The plate was sealed with a porous sealing film and grown at 37° C. with shaking at 230 r.p.m. for 1 h. 175 µL of cells were transferred to a 96-well black-walled clear-bottom plate (Costar), and then 600 nm absorbance and luminescence were read using an ClarioSTAR (BMG Labtech) over the course of 8 h, during which the cultures were incubated at 37 C. Calculation of % WT occurs as follows. Begin with three values, the luminescence at OD=0.3 of the WT luciferase positive control (P), the induced tRNA (i), and the suppressed tRNA (s). % WT= (P−s)/(i−s).

Phage Cloning.

To clone bacteriophage, PCR fragments were assembled as usual using USER assembly. The annealed fragments are transformed into competent E. coli S2060 cells that already bear a plasmid containing pIII under control of the phage shock promoter, pJC175e. Transformants were recovered overnight, centrifuged at 8,000 g for 2 min and supernatant filtered through a 0.22 µm PVDF Ultrafree centrifugal filter (Millipore). The filtered supernatant containing phage was plagued, and clonal plaques were expanded overnight and Sanger sequenced.

Phage Plaque Assays

S2060 cells were transformed with the phage activity reporters of interest as described above. Overnight cultures of single colonies grown in 2×YT media supplemented with maintenance antibiotics were diluted 1,000-fold into fresh 2×YT media with maintenance antibiotics and grown at 37° C. with shaking at 230 r.p.m. to OD600 ~0.6-0.8 before use. Bacteriophage were serially diluted 100-fold (4 dilutions total) in H2O. 100 µL of cells were added to 100 µL of each phage dilution, and to this 0.85 mL of liquid (70° C.) top agar (2×YT media+0.6% agar) supplemented with 2% Bluogal (Gold Biotechnology) was added and mixed by pipetting up and down once. This mixture was then immediately pipetted onto one quadrant of a quartered Petri dish already containing 2 mL of solidified bottom agar (2×YT media+1.5% agar, no antibiotics). After solidification of the top agar, plates were incubated at 37° C. for 16-18 h.

Phage Enrichment Assays

S2060 cells were transformed with the phage activity reporters of interest as described above herein. Overnight cultures of single colonies grown in 2×YT media supplemented with maintenance antibiotics were diluted 1,000-fold into DRM media with maintenance antibiotics and grown at 37° C. with shaking at 230 r.p.m. to OD600 ~0.4-0.6. Cells were then infected with bacteriophage at a starting titer of $10^5$ pfu/mL. Cells were incubated for another 16-18 h at 37° C. with shaking at 230 r.p.m., then centrifuged at 8,000 g for 2 min and filtered through a 0.22 µm PVDF Ultrafree centrifugal filter (Millipore). The filtered supernatant containing phage was removed and stored at 4° C. The phage titer of these samples was measured in an activity-independent manner using a plaque assay containing E. coli bearing pJC175e.

Continuous Flow PACE

Unless otherwise noted, PACE apparatus, including host cell strains, lagoons, chemostats, and media, were all used as previously described. Chemically competent S2060s were transformed with the phage propagation reporter and MP6 as described above, plated on 2×YT media+1.5% agar supplemented with 25 mM glucose (to prevent induction of mutagenesis) in addition to maintenance antibiotics, and grown at 37° C. for 18-20 h. Four colonies were picked into 1 mL DRM each in a 96-well deep-well plate, and this was diluted five-fold eight times serially into DRM. The plate was sealed with a porous sealing film and grown at 37° C. with shaking at 230 r.p.m. for 16-18 h. Dilutions with OD600 ~0.4-0.8 were then used to inoculate a turbidostat containing 300 mL DRM. The turbidostat maintains the growing culture at OD600 ~0.7-0.8.

Prior to bacteriophage infection, lagoons were continuously diluted with culture from the turbidostat at 1 lagoon vol/h and pre-induced with 10 mM arabinose for at least 45 minutes. Samples (500 µL) of the SP population were taken at indicated times from lagoon waste lines. These were centrifuged at 8,000 g for 2 min, and the supernatant was passed through a 0.22 µm PVDF Ultrafree centrifugal filter (Millipore) and stored at 4° C. Lagoon titers were determined by plaque assays using S2060 cells transformed with pJC175e.

Example 1

Suppressor tRNA Sequences (See Materials and Methods Above Herein)

Procedures were carried out to engineer quadruplet decoding tRNA variants for every *E. coli* tRNA. To identify starting points, suppressor tRNAs reported in the literature were tested. Also tested were rationally engineered suppressors using two different codon reassignment strategies, and a library-based selection method was also developed and used. Functional suppressor tRNAs were identified, and further steps were carried out to increase their function.

To improve upon the identified functional quadruplet decoding tRNAs, rapid continuous directed evolution was used and successfully evolved suppressors with improved quadruplet decoding efficiency for five different tRNA scaffolds and two different quadruplet codons. In every case, tRNA variants arose that exhibited substantial improvements in quadruplet decoding. The most efficient evolved suppressor is capable of efficiently translating a protein that contains four frameshifts, breaking the existing three-frameshift record.

The resulting catalog of 21 novel suppressors constitute the most comprehensive effort to engineer quadruplet decoding tRNAs to date, reveal that the anticodon loop sides frequently contribute to improved quadruplet decoding, and demonstrate the extent to which codon size is controlled at the tRNA level. The ready access to higher activity variants that decode quadruplet codons in multiple contexts reveals inherent three-versus four-base promiscuity in translation machinery that offers a tractable strategy for genetic code expansion.

Suppressor tRNAs

A number of suppressor tRNAs were developed, engineered, and tested. Sequences that encode certain of the identified suppressor tRNAs were identified and their nucleic acid sequences are set forth herein as SEQ ID NOs: 1-21, (see FIGS. 1 and 2)

Figure 10:
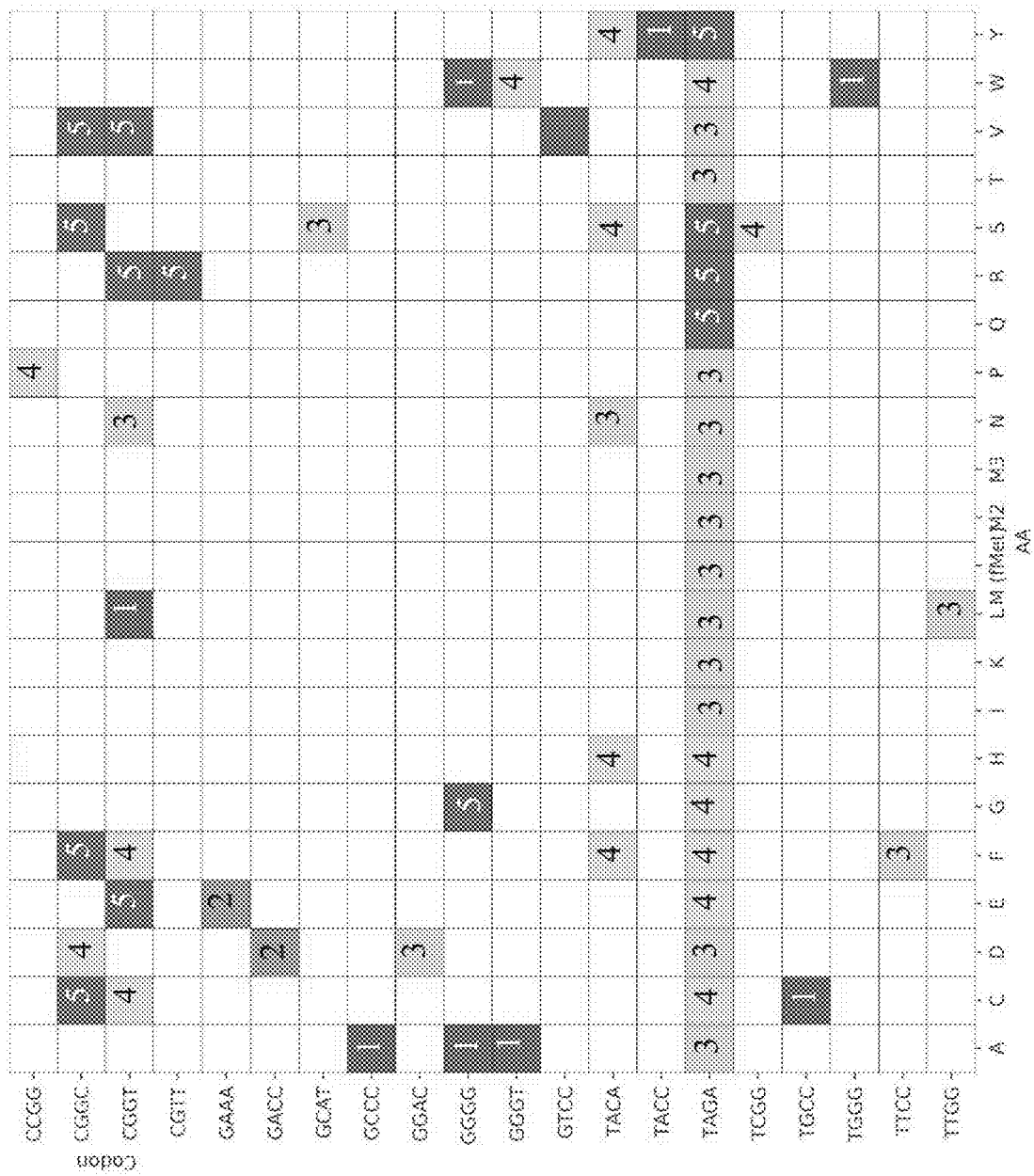
FIG. 10 shows a graphical representation of the results from codon reassignment studies. Key for boxes is: (#1) identifies extremely toxic, (#2) identifies toxic, (#3) identifies nonfunctional, (#4) identifies minimally functional (<1% of wild type) and (#5) identifies functional (>1% of wild type). Note one box is marked "4-5" to indicate result midway between minimally functional and functional.

Thirty-four suppressor tRNA-encoding sequences that were assessed for toxicity and function were determined to be non-functional, toxic, or extremely toxic when tested, see Table 1, and FIG. 10.

TABLE 1

Non-functional, toxic, and extremely toxic suppressor tRNAs

| Non-functional | | Toxic | Extremely toxic |
|---|---|---|---|
| D-TAGA | E-AGGC | D-GACC | A-GCCC |
| I-TAGA | Y-CAAG | E-GAAA | C-TGCC |
| K-TAGA | | Y-CCAT | H-CACC |
| L-TAGA | | Y-CATG | M-ATGG |
| N-TAGA | | Y-CCCT | V-GTCC |
| P-TAGA | | Y-CCTC | W-TGGG |
| T-TAGA | | Y-CCCC | Y-TACC |
| V-TAGA | | Y-AAGC | |
| F-TTCC | | Y-CTGC | |
| I-ATCC | | Y-CCAG | |
| K-AAAA | | D-CACC | |
| L-TTGG | | H-CAAC | |
| N-AACC | | | |

Example 2

Assays—Luciferase Reporter: Design and Validation Studies (See Materials and Methods Above Herein)

A luminescent assay system was prepared and tested. Experiments performed included preparing constructs for a two-plasmid luminescence reporter system of quadruplet decoding.

(a) As illustrated in FIG. 4A, one plasmid was prepared that constitutively expressed a luciferase that had been encoded using a quadruplet codon at permissive residue(s) 164 or 357. A second plasmid was prepared from which a tRNA was expressed from a using an IPTG inducible promoter.

Figure 4B:
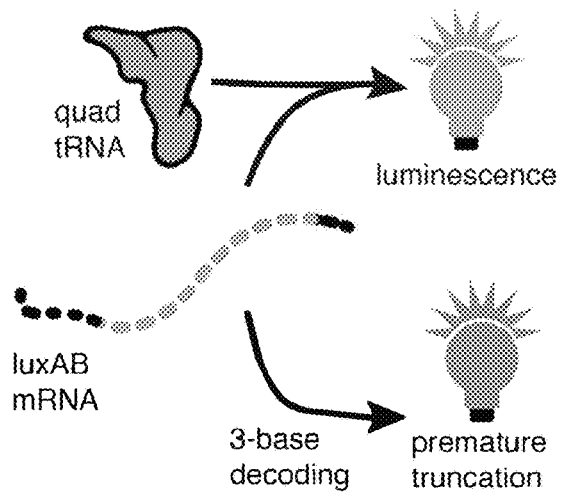

(b) Successful decoding of the quadruplet codon resulted in translation of full-length luciferase and thereby luminescence. Failure to decode the quadruplet codon resulted in a frameshift, premature termination, and a truncated, non-functional luciferase. A schematic diagram of the reporter process is shown in FIG. 4B.

Figure 4C:
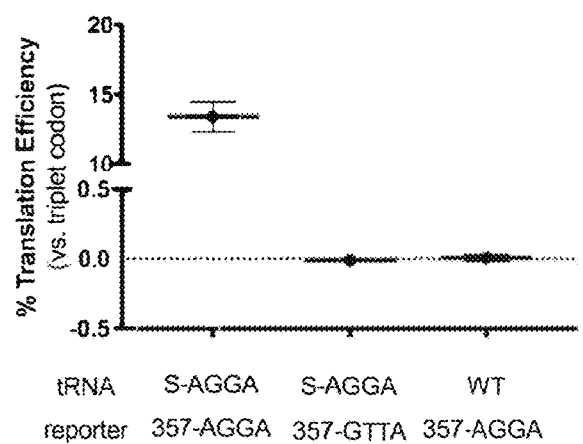

(c) This reporter was validated using two previously reported engineered quadruplet decoding tRNAs, Ser-AGGG and Ser-AGGA, [Magliery, T. et al., (2001) J. Bol. Vol. 307:755-769, the content of which is incorporated herein in its entirety by reference]. FIG. 4C shows results of the validation of the Ser-AGGA (first data point). When induced, both tRNAs could decode the quadruplet codon in the matching reporter, but not a reporter containing a mismatching quadruplet codon (FIG. 4C, second data point). As another negative control, expressing a wild type Serine tRNA did not result in luminescence (FIG. 4C, third data point).

(d) Additional experiments were performed to measure quadruplet decoding tRNAs reported in the literature. Several had no measurable activity in this assay, or resulted in high toxicity. Results are show in FIG. 4D.

(e) Measurements were taken of quadruplet decoding tRNAs that decode TAGA. Results shown in FIG. 4E indicate the % translation efficiency (Y axis) for a number of decoding tRNAs that decode TAGA, which are shown on the X axis.

(f) Measurements were taken of quadruplet decoding tRNAs that decode XYZZ, where XYZ was the original codon corresponding to each tRNA scaffold. Results shown in FIG. 4F indicate the % translation efficiency (Y axis) for a number of decoding tRNAs that decode XYZZ, which are shown on the X axis. Induction of seven of these tRNA, results in high toxicity, as indicated on graph with "X".

(g) Together, these approaches revealed at least one naive quadruplet decoding tRNA with detectable activity for 13/20 canonical amino acids. These naive tRNAs can be used as starting points for directed evolution. General results are show in FIG. 4G.

Example 3

Evolving Suppressor tRNAs—(See Materials and Methods Above Herein)

Figure 4D:
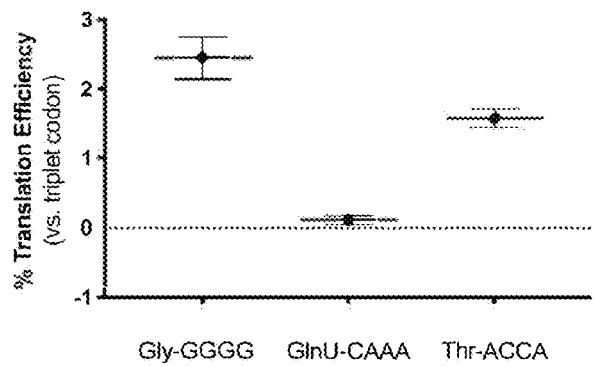

A major challenge in any directed evolution campaign is identifying starting components with sufficient initial activity to begin evolution. For simplicity of the resulting system, the initial experiments were focused on suppressor tRNAs that could be charged endogenously in E. coli. A first step was to measure the efficiency of known quadruplet decoding tRNAs using the luciferase reporter (see Example 3). Seven naturally occurring suppressor tRNAs have previously been reported in bacteria: sufD (incorporates Gly, GGGG anticodon) [Riddle, D. L. & Carbon, J. Nat. New Biol. 242, 230-234 (1973); Yourno, J. & Tanemura, S. Nature 225, 422-426 (1970).], hopR (Val, GUNA) [O'Connor, M., et al., EMBO J. 8, 4315-4323 (1989)], sufB (Pro, CCCC) [Sroga, G. E., et al., Nucleic Acids Res. 20, 3463-3469 (1992)], sufJ (Thr, ACCN) [Bossi, L. & Smith, D. M. Proc. Natl. Acad. Sci. U S. A. 81, 6105-6109 (1984)], suf16 (Gly, GGGG) [Gaber, R. F. & Culbertson, M. R. Gene 19, 163-172 (1982)], sufG (Gln, CAAA) [O'Connor, M. Nucleic Acids Res. 30, 1985-1990 (2002)], su6 (Leu, UAGG) [Moore, B., et al., J. Mol. Biol. 298, 195-209 (2000)], and su7 (Gln, UAGG) [Curran, J. F. & Yarus, M. Science 238, 1545-1550 (1987)]. These seven suppressor tRNAs were measured in S2060 E. coli using the luciferase reporter (FIG. 4D). Many of these suppressors are toxic and nonfunctional in the assay. In total, a search of the literature identified minimally functional suppressor tRNAs for 4/20 canonical amino acids (FIG. 4G). (The content of each reference indicated in this paragraph is incorporated by reference herein in its entirety.)

To expand the catalog of minimally functional suppressor tRNAs to more comprehensively cover the canonical amino acids, studies were performed using rational engineering. A straightforward approach to converting a naturally occurring triplet-decoding tRNA into a quadruplet decoding one is as simple as replacing the anticodon. Two strategies for codon reassignment were tested.

Previous efforts to engineer a complete set of amber suppressor tRNAs were largely successful [Magliery, T. J., et al., Edited by M. Gottesman. J. Mol. Biol. 307, 755-769 (2001) and Lee, B. S., et al., Biochim. Biophys. Acta 1861, 3016-3023 (2017)]. TAGA, a quadruplet codon that begins with the amber stop codon, has been used successfully several times previously. TAGA suppressors compete with the amber stop codon TAG, the lowest-usage codon in E. coli's genome [Zhang, S. P., et al., Gene 105, 61-72 (1991)], potentially explaining TAGA suppressor efficiency. Experiments were performed and a complete set of 20 E. coli TAGA suppressors were engineered by replacing the anticodon in each tRNA with 5'-TCTA-3'. The efficiency and toxicity of these suppressors was measured using the luciferase reporter (FIG. 4E). 11/20 TAGA suppressors showed detectable efficiency. (The content of each reference indicated in this paragraph is incorporated by reference herein in its entirety.)

It was observed that duplication of the third base of the codon is a common motif in naturally occurring quadruplet decoding tRNAs (if XYZ is the original codon, XYZZ is the quadruplet codon) [Curran, J. F. & Yarus, M. Science 238, 1545-1550 (1987); Riddle, D. L. & Carbon, J. Nat. New Biol. 242, 230-234 (1973); Yourno, J. & Tanemura, S. Nature 225, 422-426 (1970); Sroga, G. E., et al., Nucleic Acids Res. 20, 3463-3469 (1992); Gaber, R. F. & Culbertson, M. R. Gene 19, 163-172 (1982); O'Connor, M. Nucleic Acids Res. 30, 1985-1990 (2002); and Moore, B., et al., J. Mol. Biol. 298, 195-209 (2000)]. 18/20 synthetases must charge tRNAs that decode codons with different third bases [Sonneborn, T. M. In Evolving Genes and Proteins (eds. Bryson, V. & Vogel, H. J.) 377-397 (Academic Press, 1965)], potentially explaining plasticity in this area of tRNA identity elements. Given that this strategy for codon reassignment minimally disrupts the anticodon, a complete set of "XYZZ suppressors" were engineered. 6/20 XYZZ showed detectable efficiency with the luciferase reporter (FIG. 4F). Additionally, 7/20 XYZZ suppressors were more toxic than could be quantified using the doubling time assay. (The content of each reference in this paragraph is incorporated by reference herein in its entirety.)

It was also identified that not all quadruplet codons could be successfully integrated into all tRNA scaffolds. This rational engineering approach required the user to guess-and-check individual tRNA scaffold/quadruplet codon pairs to discover successful codon reassignments. In addition, these mutated tRNAs might no longer have been specifically charged with a single amino acid. Overall, the methods to rationally engineer suppressors resulted in 12/20 starting points for directed evolution (FIG. 4G).

Figure 4H:
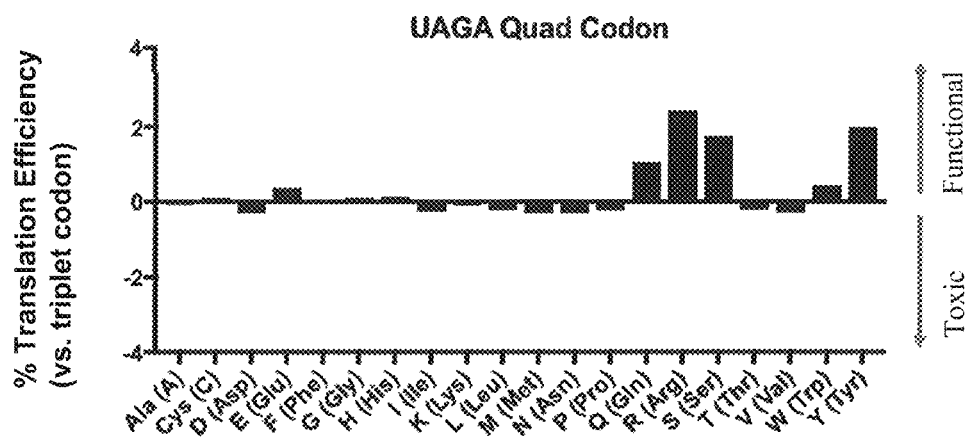
Figure 4I:
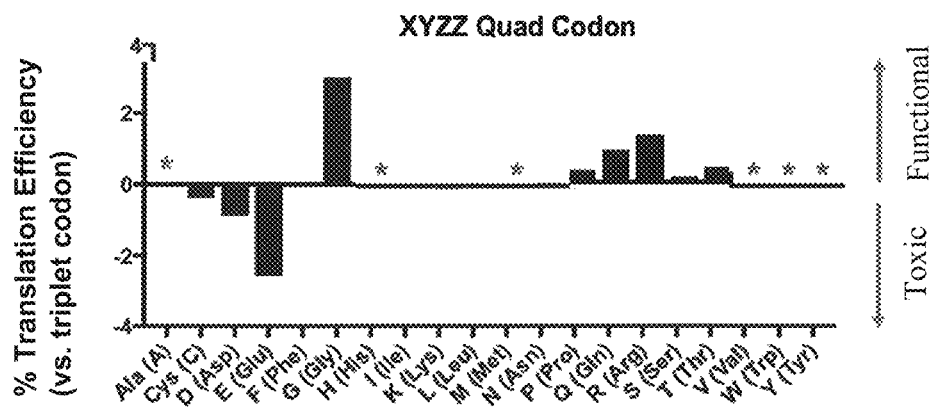

It was observed that certain attempts to perform codon reassignment resulted in a nonfunctional or toxic suppressor for several potential reasons: (1) 17/20 AARSs identify their tRNA by recognizing bases in the anticodon loop 45 and may be unable to recognize or charge a tRNA with a quadruplet anticodon; (2) the new anticodon must be compatible with the bases in the tRNA scaffold [Kleina, L. G., et al., J. Mol. Biol. 213, 705-717 (1990) and Yarus, M. Science 218, 646-652 (1982)]; (3) mutated tRNAs may act as a competitive inhibitor for endogenous tRNAs for AARSs; (4) functional frameshift suppressor tRNAs may disrupt translation of the host proteome and thereby exhibit high toxicity; and (5) EF-Tu checks anticodon/AA before allowing translation [Shepherd, J. & Ibba, M. FEMS Microbiol. Rev. 39, 280-300 (2015), the contents of which is incorporated herein by reference in its entirety]. Studies were performed to determine whether any one of these effects were correlated with trends in the success or failure of the suppressor engineering. Based on the results of studies performed, the following observations were made:

(a) E. coli AARSs for alanine and leucine do not interact with the anticodon loop [Giegé, R., et al., Nucleic Acids Res. 26, 5017-5035 (1998); the contents of which is incorporated herein by reference in its entirety]. However, functional suppressors were not able to be obtained for these amino acids. Additionally, the attempts did not generate toxic tRNAs. This indicated that item (1) (above) was not the only factor limiting discovery of suppressor tRNAs based on diverse scaffolds (b) Tests were performed to assess codon reassignment strategies. FIG. 4H shows results of % transcription efficiency (versus triplet codon) for UAGA Quad Codons, indicating functional and toxic results. FIG. 4I provides results of tests indicating that among the codon reassignment strategies tested, the XYZZ suppressors were more likely to exhibit very high toxicity.

All the suppressors discovered to this point are referred to as "naïve" suppressors. It is possible that the remaining seven canonical amino acids are not amenable to being charged endogenously, and will require evolution of the *E. coli* AARS, or that a tRNA/AARS pair be imported from another organism.

Example 4

Directed Evolution of Suppressor tRNAs—M13 Phage Propagation Reporter
(See Materials and Methods Above Herein).

(a) A construct was designed for phage propagation reporter. The reporter plasmid was prepared that encoded pIII, an essential phage protein, which was encoded with one or more quadruplet codons at permissive residue(s) 29 or 34. The quadruplet decoding tRNA was encoded on an M13 phage from which pIII deleted. (See FIG. 5A).

(b) When challenged to infect *E. coli* bearing the reporter plasmid, the Selection Phage entered the cell. Successful decoding of the quadruplet codon resulted in translation of full-length pIII and thereby infectious phage progeny. Failure to decode the quadruplet codon resulted in a frameshift, premature termination, and a truncated, non-functional pIII. (See FIG. 5B).

(c) This reporter was validated using two highly active quadruplet decoding tRNAs that had been identified: R-CGTT-naive and R-TAGA-naive. Phage bearing both these suppressors were capable of forming plaques when challenged to infect *E. coli* bearing a phage propagation reporter with a matching quadruplet codon, but not with a non-matching quadruplet codon. Both phage could plaque in *E. coli* that supply pIII in response to phage infection (PSP-pIII). M13 phage from which pIII had not be deleted could form plaques regardless of phage propagation reporter. (See FIG. 5C).

(d) To determine the relationship between the luciferase and phage propagation reporter results, nine functional TAGA suppressors were tested with a TAGA phage propagation reporter. Suppressors that measured at least 1% wild type (WT) activity in the luminescence assay reliably supported phage propagation at levels sufficient for directed evolution. (See FIG. 5D).

Results

Figure 5A:
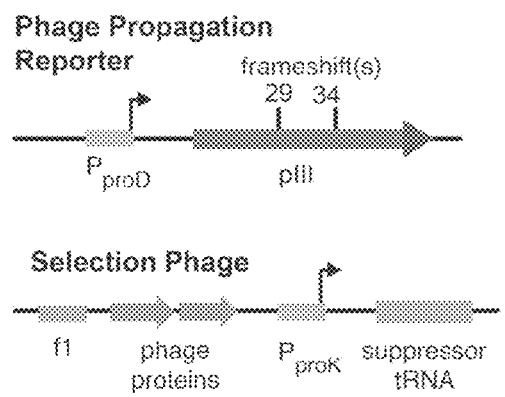
FIG. 5A-D provides schematic diagrams, images, and a graph illustrating an M13 phage propagation reporter of quadruplet decoding.
Figure 5B:
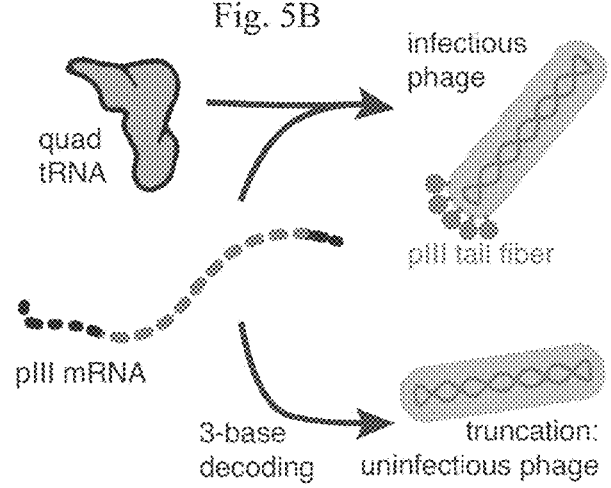
Figure 5C:
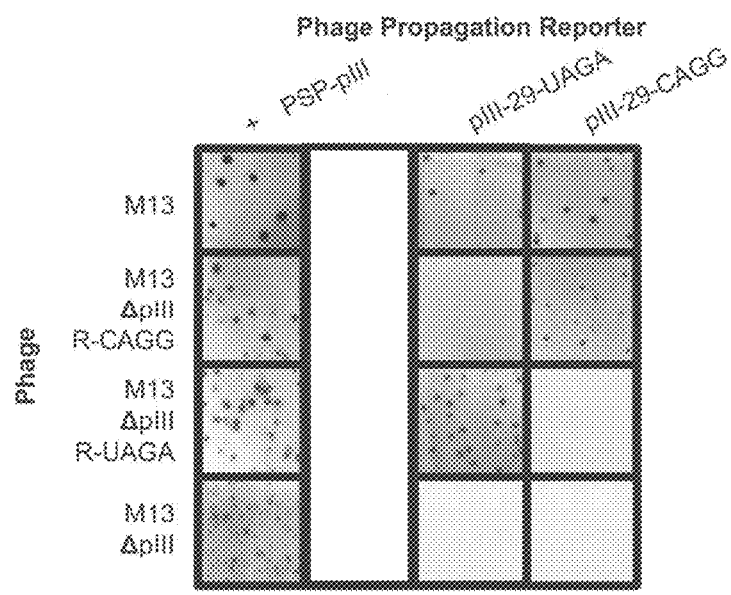

To evolve the identified minimally functional quadruplet decoding tRNAs studies were performed using an M13-bacteriophage based directed evolution technique [Esvelt, K. M., et al., *Nature* 472, 499-503 (2011)]. First, a phage propagation reporter was prepared that tied successful quadruplet decoding to M13 phage propagation. In this system, an essential phage protein pIII was encoded with one or more quadruplet codons. A quadruplet decoding tRNA was encoded on an M13 phage from which pIII has been deleted (FIG. 5A). When challenged to infect *E. coli* bearing the pIII-containing reporter plasmid, functional phage were produced in proportion to quadruplet decoding activity (FIG. 5B). Previously another approach had been used to tie phage propagation to three-base codon amber suppression integrated at permissive residue pIII-P29 [Bryson, D. I., et al., (2017). Nat. Chem. Biol. December; 13(12):1253-1260, the contents of which is incorporated herein by reference in its entirety]. Studies were performed and this reporter was validated in the quadruplet codon context by integrating a CGTT or TAGA quadruplet codon at pIII-29 and then verifying that phage bearing the R-CGTT-naive or R-TAGA-naive suppressors shows phage propagation in the form of plaquing (FIG. 5C); control experiments with mismatched quadruplet anticodons or lacking the suppressor tRNA confirm the requirements for cognate codon/anticodon interactions for phage propagation. These experiments confirmed that phage propagation was tied to quadruplet decoding activity.

Example 5

Continuous Directed Evolution of Quadruplet Decoding tRNAs
(See Materials and Methods Above Herein)

(a) Five tRNA suppressors were evolved in continuous culture. FIG. 6A shows results included graphs showing phage titers (left axis, solid lines) and population dilution rate (right axis, dashed lines). Phage titers generally remained flat or rose over the course of evolution. In two instances, Q-NNNN and R-NNNN, the experiments were seeded with phage bearing a randomized anticodon loop rather than a clonal variant; in both cases the final population was overtaken by phage bearing the expected anticodon.

Figure 6B:
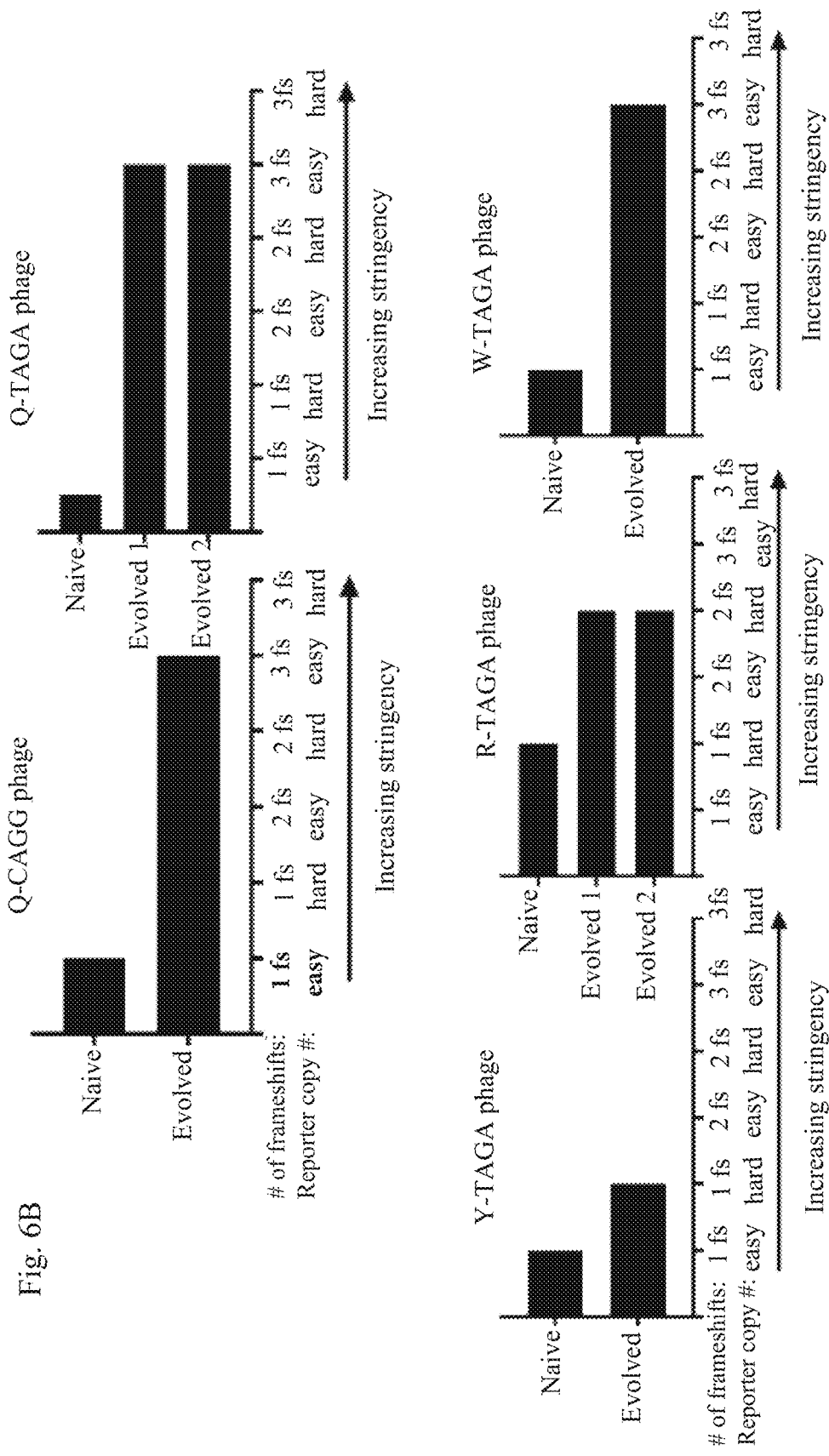

(b) To determine the results of evolution, initial and final tRNA variants were compared against a ladder of phage activity reporters of increasing difficulty. Phage were initially capable of efficiently producing infectious progeny that require production of pIII that contains 1 quadruplet codon; in contrast, the evolved phage are capable of relying on a pIII that requires 3 quadruplet codons. Results of some studies are shown in FIG. 6B.

Figure 6C:
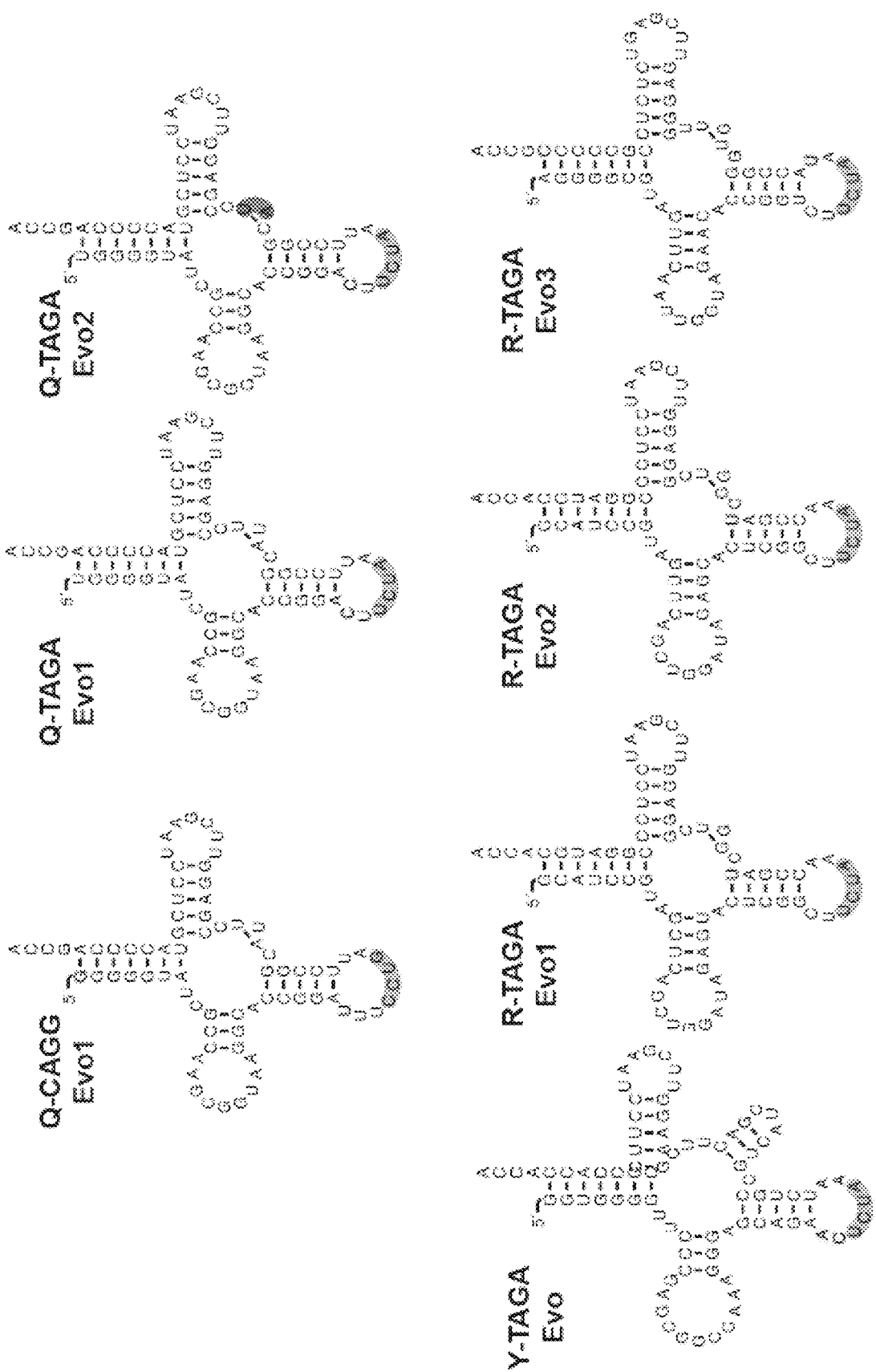

(c) Sequences of evolved tRNA variants. Of the 5 variants, 4 of them involved mutations to the sides of the anticodon loop. These set include deletions (Q-TAGA-Evo2), insertion (Q-CAGG-Evo1), and recoding of base-paired regions (R-TAGA-Evo2). Results of some studies are shown in FIG. 6C.

Figure 6D:
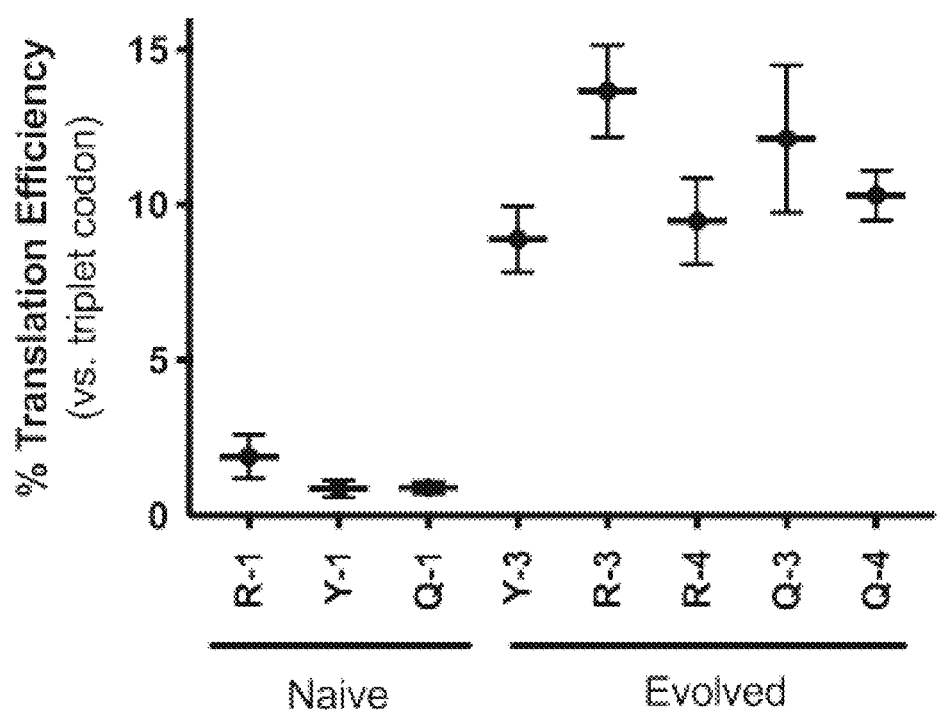

(d) To measure the properties of these tRNA variants independent of potential changes in the phage backbone, the tRNA variants were subcloned into the inducible tRNA expression plasmid and measured using the luminescence reporter. Efficiency of the evolved variants were measured relative to their naive evolutionary starting points. The efficiency of each evolved suppressor was higher than the original, showing generally about an order of magnitude improvement. (Results certain studies are shown in FIG. 6D).

Results

Figure 5D:
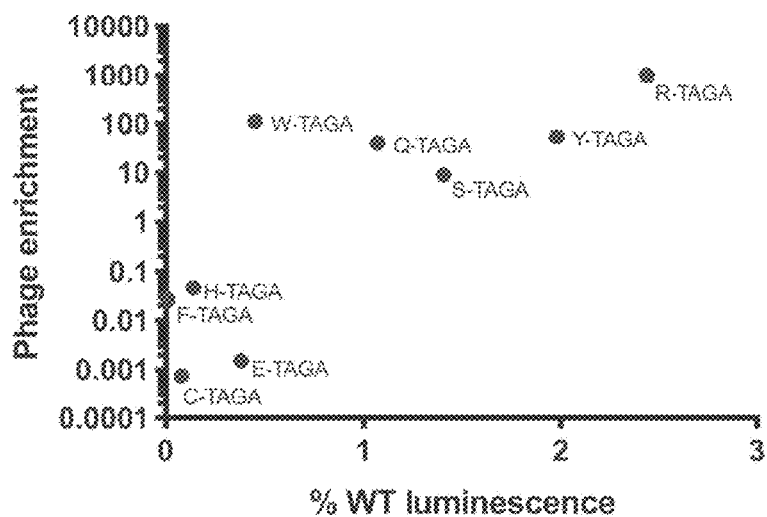

The existing catalog of naive quadruplet decoding tRNAs span a wide range of suppression efficiencies, from 0.1% to 20% of WT. The stringency of the phage propagation reporter was manipulated by changing the copy number of the plasmid [Peterson, J. & Phillips et al., *Plasmid* 59, 193-201 (2008)], the strength of the promoter [Davis, J. H., et al., *Nucleic Acids Res.* 39, 1131-1141 (2011)], and the number of frameshifts (SI: phage propagation); together, these modifications allowed reporters to be generated that challenged suppressors at a wide range of efficiencies. To establish a comparison between luminescence and phage propagation reporters, activity-dependent phage enrichment and plaquing was tested for the nine most efficient naive TAGA suppressors (FIG. 5D), using two most lenient reporters. There was good agreement between the results, and phage bearing suppressors around 1% of WT activity showed activity-dependent phage propagation (FIG. 5D). (The content of each reference recited in this paragraph is incorporated herein by reference in its entirety.)

To evolve the quadruplet decoding tRNA, procedures were carried out to repeatedly enrich populations of phage for functional variants using the phage propagation reporter. As the phage genome replicates, mutations arise, some of which may be in the quadruplet decoding tRNA. The studies employed an inducible mutagenesis plasmid [Badran, A. H. & Liu, D. R. Nat. Commun. 6, 8425 (2015)] to elevate this mutation rate to levels that rival that of traditional in vitro mutagenesis used in directed evolution. Thus, repeated enrichment of phage in E. coli carrying a phage propagation reporter construct resulted in directed evolution of the tRNA. This technique, known as Phage Assisted Continuous Evolution (PACE) [Esvelt, K. M., et al., Nature 472, 499-503 (2011)], has been used to evolve protease substrate specificity [Packer, M. S., et al., Nat. Commun. 8, 956 (2017) and Dickinson, B. C., et al., Nat. Commun. 5, 5352 (2014)], aminoacyl tRNA synthetases [Bryson, D. I., et al., (2017). Nat. Chem. Biol. December; 13(12):1253-1260], antibody solubility [Wang, T., Badran, et al., Nat. Chem. Biol. 14, 972-980 (2018)], biosensors [Pu, J., Zinkus-Boltz, J. & Dickinson, B. C. Nat. Chem. Biol. 13, 432-438 (2017)], and broad-PAM specificity Cas9 variants [Hu, J. H., et al., (2018). Nature April 5; 556(7699):57-63], amongst other applications. PACE biologically automates the traditional directed evolution workflow, compressing the multi-day process of library creation and screening into the rapid 20-minute lifecycle of a bacteriophage. (The content of each reference recited in this paragraph is incorporated herein by reference in its entirety.)

Studies performed included culturing phage bearing a Q-NNNN suppressor library continuous flow, challenging the population to propagate in bacteria bearing the MP6 mutagenesis plasmid and a phage propagation reporter containing pIII-29-CAGG. The expectation was that the Q-CAGG-naive suppressor, a member of the inoculating library, would be enriched. Additionally, evolved variants of Q-CAGG-naive might also emerge. Indeed, both events occurred after 45 hours of continuous evolution. A one-mutant of Q-CAGG-naive, Q-CAGG-Evo1, overtook the population (FIG. 6A). Studies were performed to compare the starting and ending fitness of the phage using enrichment assays, and it was determined that the evolved phage bearing Q-CAGG-Evo1 exhibits a substantially higher ability to decode quadruplet codons; it is capable of supporting phage propagation using a copy of pIII containing three frameshifts (FIG. 6B).

Figure 6E:
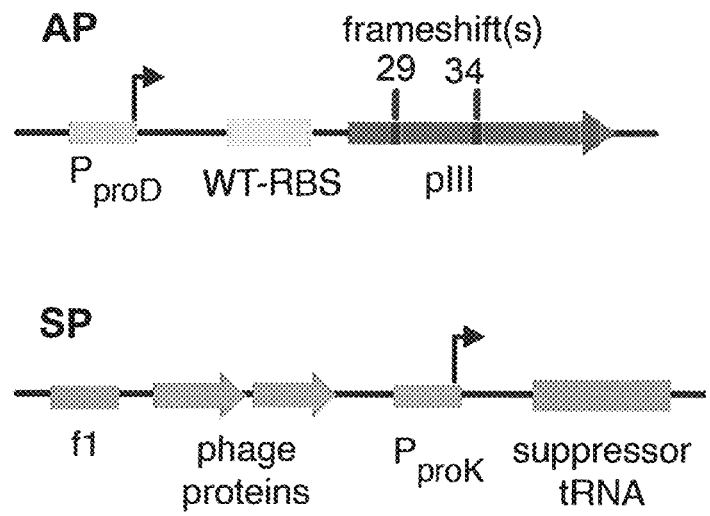
Figure 6F:
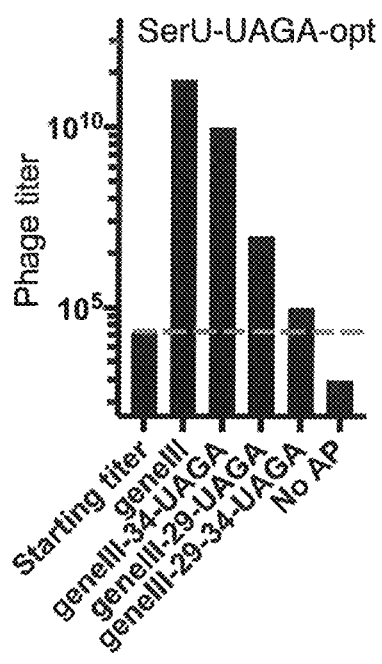

Studies were performed to assess frameshift suppression. FIG. 6E is a schematic diagram of strategy showing an accessory plasmid (top) with frameshifts indicated and a selection phage schematic (bottom). FIG. 6F illustrates results of phage enrichment and confirmed that propagation relied on quadruplet decoding.

Example 6

Continuous Directed Evolution of S-UAGA tRNA
(See Materials and Methods Above Herein)

(a) Studies were performed in which the Serine-UAGA tRNA was evolved in continuous culture, challenging it to decode one quadruplet codon for the first 24 hours and then to decode three quadruplet codons for the final 30 hours. Results show in FIG. 7A. Total phage titer (solid) generally fell and then rose over the course of each segment of the evolution. The population dilution rate (dashed) was used to increase selection pressure during the course of evolution.

(b) Studies were performed to compare the initial and final tRNA variants against a ladder of phage activity reporters of increasing difficulty. Evolved phage are capable of relying on a pIII that requires 4 quadruplet codons (see FIG. 7B).

(c) Sequences of evolved variants of the SerU-UAGA tRNA. Evolved 3 contains a stem-re-coding mutation (see FIG. 7C).

Figure 7A:
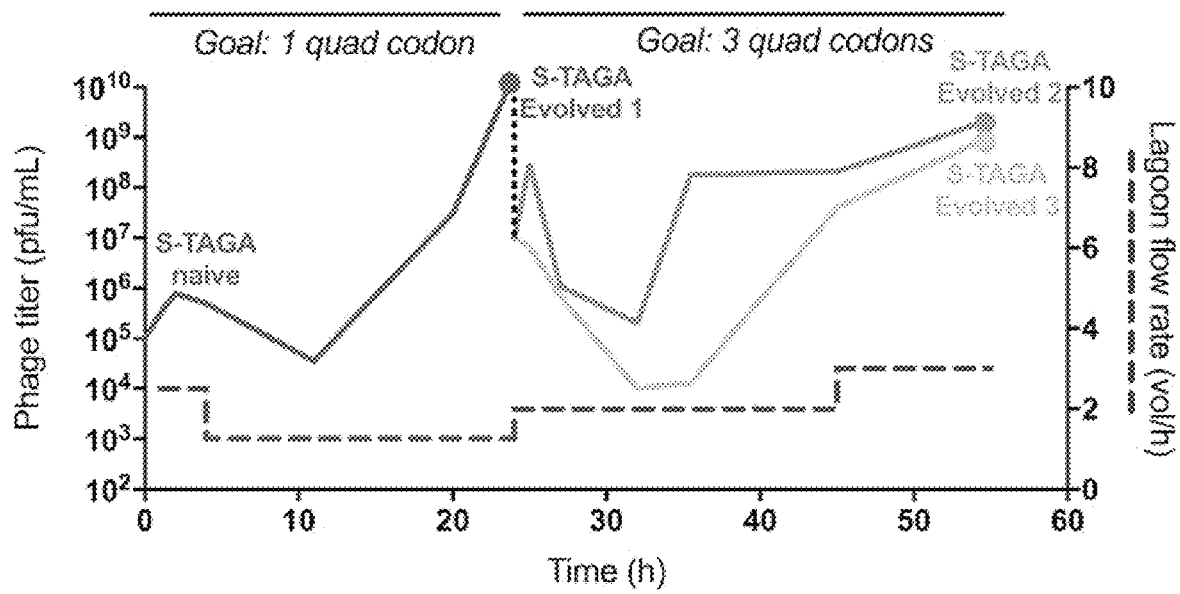
Figure 7B:
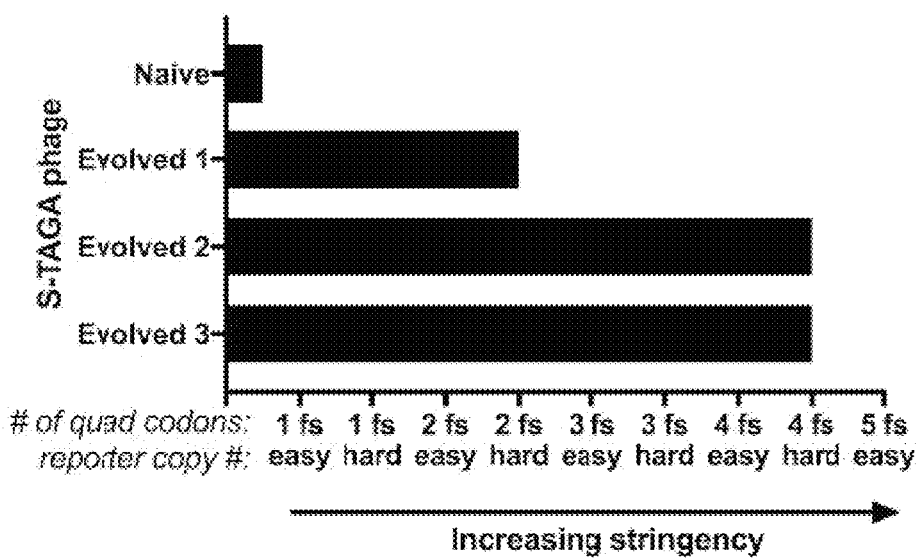

(d) These tRNA variants were subcloned into the inducible tRNA expression backbone and measured using the luminescence reporter. The efficiency of evolved suppressors has improved, as demonstrated by a kinetic luminesce assay. The most evolved suppressor variants are on-par with the Mj-Tyr tRNA/AARS pair in decoding UAG codons (see FIG. 7D).

Figure 7E:
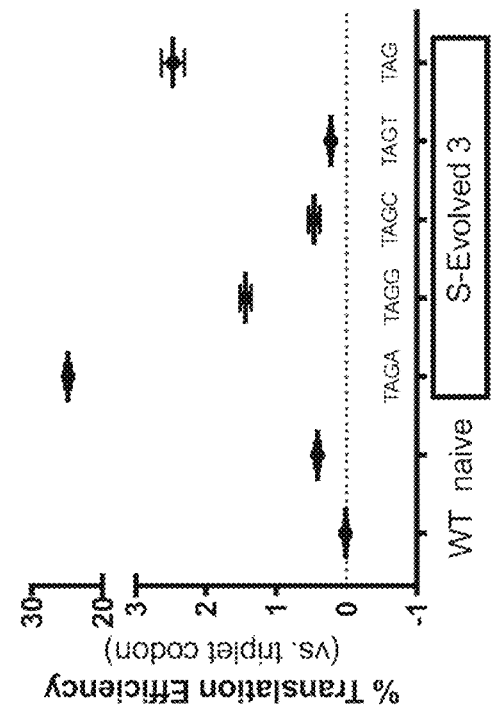
Figure 7D:
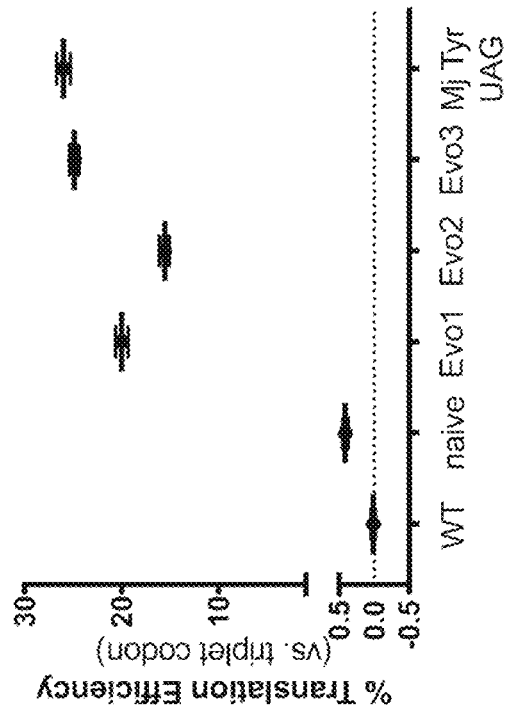

(e) Crosstalk between evolved variants and fourth-base mismatch codons, or the amber suppressor was measured. The evolved suppressor showed significant preference for decoding four-base codons with the matching fourth base. It showed measurable crosstalk with the three base codon TAG. As quadruplet decoding tRNAs are known to crosstalk with four-base codons with a mismatched fourth base [Gaber, R. F. & Culbertson, M. R. Mol. Cell. Biol. 4, 2052-2061 (1984); Anderson, J. C., Magliery, T. J. & Schultz, P. G. Chem. Biol. 9, 237-244 (2002); Curran, J. F. & Yarus, M. Science 238, 1545-1550 (1987); and Fagan, C. E., et al., RNA 20, 1944-1954 (2014)], tests for this crosstalk were performed (FIG. 7E). Additionally, the UAGA suppressors were tested for crosstalk with suppression of the amber stop codon (FIG. 7E). (The content of each reference recited in this paragraph is incorporated herein by reference in its entirety.)

Results

Studies were performed to determine whether the success of this technique was dependent on the CAGG codon, and to obtain results for a different quadruplet codon. Five of the most functional TAGA suppressors were evolved in continuous flow using a lenient TAGA phage reporter. Two independent experiments were performed, one each for Q and R, in both case one experiment was seeding with phage bearing the NNNN library, in the other with a clonal TAGA-naive suppressor (FIG. 6A, FIG. 7A). Some experiments experienced phage washout or evolution of phage-pIII recombinants due to low starting activity (SI: continuous evolution experiments). All other experiments, comprising at least one experiment for every tRNA scaffold tested, evolved tRNA variants that swept the population (FIG. 6A, FIG. 7A). Replicate experiments evolved similar mutations. Clonal phage bearing these evolved suppressors were characterized and it was found they all show improved activity, again supporting phage propagation using a pIII transcript requiring three frameshifts (FIG. 6B). Additionally, the evolved tRNAs were isolated and tested the side-by-side with their naive equivalents using the luminescence reporter; evolved variants generally show about an order of magnitude improvement in quadruplet decoding efficiency (FIG. 6D).

Studies were performed to determine whether higher efficiency variants could be produced through further evolution on a more difficult evolutionary goal. Additionally, the phage activity reporters used so far for evolution all contain a single frameshift at pIII-29, and tests were performed to determine if the evolved suppressors were specific for that transcript context. These tests included evolving S-TAGA-Evo1 on a substantially more challenging three-frameshift phage propagation reporter. Over the course of an additional 30 hours of evolution, two additional sweeping variants arose in the two parallel experiments, S-TAGA-Evo2, S-TAGA-Evo3 (FIG. 7A). These variants now showed activity on a phage activity reporter requiring four frameshifts (FIG. 7B). Analysis of these variants using the luminescence reporter show that the most evolved variant decodes the UAGA quadruplet codon at the same efficiency as a UAG suppressor.

Example 7

Reporter Development Method
(See Materials and Methods Above Herein)

Figure 8:
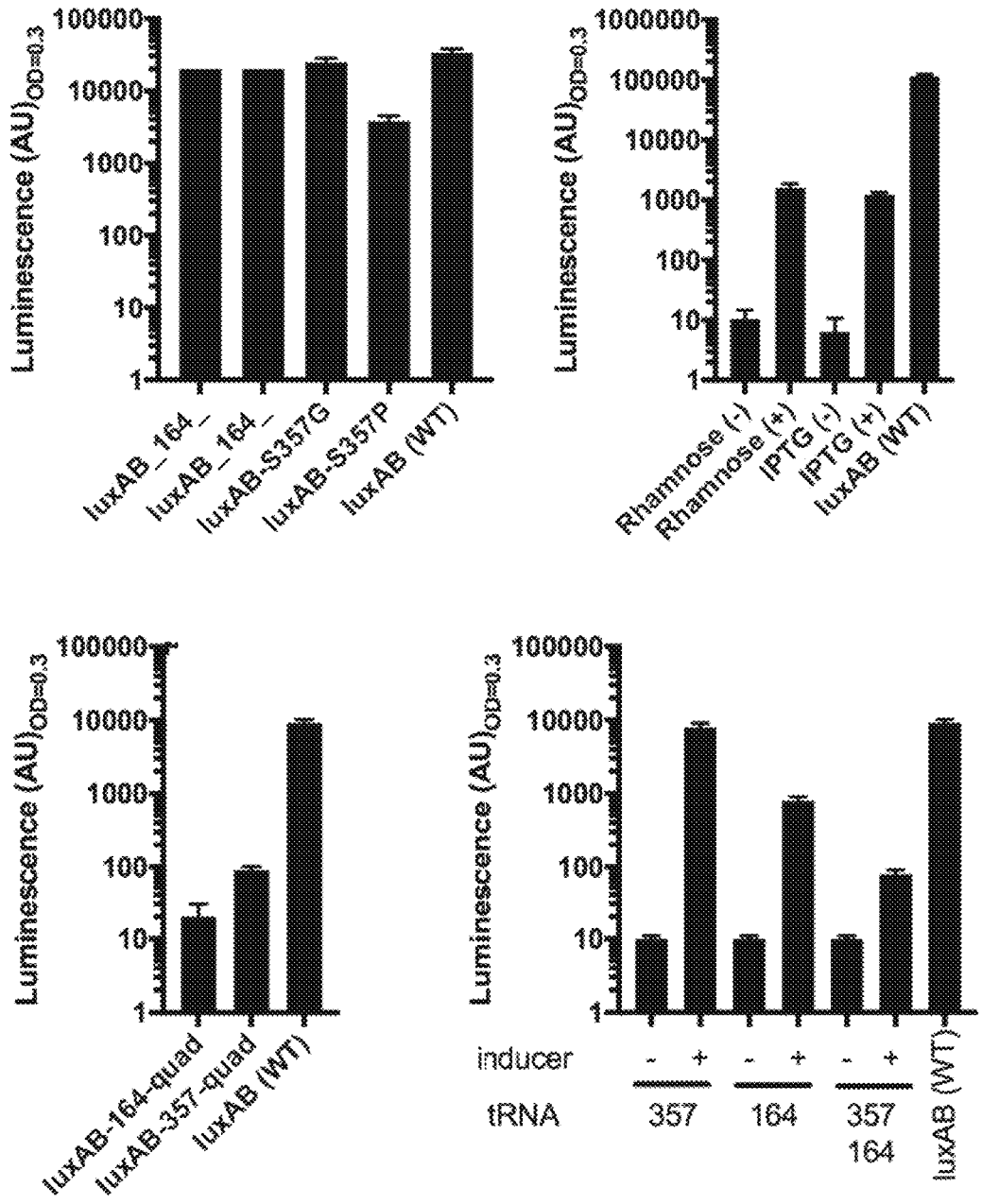
FIG. 8 provides four graphs indicating process and results of a luminescence reporter development. The left, top row graph shows results obtained from experiments that examined: permissive residue identification. The right, top row graph shows results obtained from experiments that examined inducible tRNA promoter. The left, bottom row graph shows results obtained from experiments that examined frameshift propensity. The right, bottom row graph shows results obtained from experiments that examined reporter stringency modulation.

In order to make this reporter usable for all the canonical amino acids, two permissive residues in luxAB were identified: 161 and 357 (residue positions in polypeptide encoded by SEQ ID NO: 26, by generating mutants with dissimilar amino acids and confirming that luminescence was not abolished. Results show in FIG. 8.

Two inducible promoters, $P_{rha}$ [Tate, C. G., et al., *J. Biol. Chem.* 267, 6923-6932 (1992)] and $P_{trc}$ [Amann, E. & Brosius, J. *Gene* 40, 183-190 (1985)] were tested but a new promoter, PproK-lacO was designed and used for IPTG induction because of its improved characteristics of low background and high dynamic range (SI).

It was observed that residues 164 and 357 of luxAB have different propensity for frameshifting (SI); consistent with frameshift suppression being dependent on sequence context [Salser, W. *Mol. Gen. Genet.* 105, 125-130 (1969); Fluck, M. M., et al., *Mol. Gen. Genet.* 151, 137-149 (1977); Salser, W., et al., *Cold Spring Harb. Symp. Quant. Biol.* 34, 513-520 (1969); Yahata, H., et al., *Mol. Gen. Genet.* 106, 208-212 (1970); Akaboshi, E., et al, *Mol. Gen. Genet.* 149, 1-4 (1976); Feinstein, S. I. & Altman, S. I *Mol. Biol.* 112, 453-470 (1977); Colby, D. S., et al., *Cell* November; 9(3): 449-63 (1976); Feinstein, S. I. & Altman, S. *Genetics* 88, 201-219 (1978); and Fluck, M. M. & Epstein, R. H. *Mol. Gen. Genet.* 177, 615-627 (1980); the content of each of which is incorporated herein in its entirety by reference.]

Experiments confirmed that a luciferase encoded with quadruplet codons at both residues 161 and 357 acts as a more stringent reporter.

Performance of this reporter to a GFP-based fluorescence reporter and a chloramphenicol acetyl transferase-based [Wang, K., et al., *Nat. Biotechnol.* 25, 770-777 (2007), the content of which is incorporated herein in its entirety by reference] antibiotic reporter (SI), and found that the suppressor tRNAs showed identical trends, but the luciferase-based reporter had lower background and higher dynamic range. (The content of each reference recited in Example 8 is incorporated herein by reference in its entirety.)

Example 8

PproK-lacO Promoter

A promoter sequence was designed and validated using certain methods provided in previous examples herein. The promoter, referred to herein as a PproK-lacO promoter, integrates the conventionally used PproK promoter for tRNA production. Use of the PproK-lacO promoter sequence was determined to further improve the utility of the conventional PproK promoter due at least in part to the inclusion of lacO sequence. Studies carried out using the PproK-lacO promoter demonstrated that the PproK-lacO promoter ensured lacI/IPTG-dependent tRNA transcription. The nucleic acid sequence of the PproK-lacO promoter is set forth herein as SEQ ID NO: 25.

Examples 9-14

Examples 9-14 describe experiments and studies performed to produce and test engineered tRNAs that support quadruplet codon translation. From the studies sequences encoding suppressors were generated and tested, and included sequences set forth herein as: SEQ ID NOs: 28-97 and 131-145, for sequences see FIG. 9A-B.

General Materials and Methods for Examples 9-14, See Also Example 8.

Materials

Antibiotics (Gold Biotechnology) were used at the following working concentrations: carbenicillin, 50 µg/mL; spectinomycin, 100 µg/mL; chloramphenicol, 40 µg/mL; kanamycin, 30 µg/mL; tetracycline, 10 µg/mL; streptomycin, 50 µg/mL. Water was purified using a MilliQ purification system (Millipore). Phusion U Hot Start DNA polymerase (Thermo Fisher Scientific) was used for all PCRs. Plasmids and bacteriophage were cloned by USER assembly [Geu-Flores et al., (2007) Nucleic Acids Research 35, e55-e55]. tRNA genes were amplified directly from *E. coli* genomic DNA. Plasmids were cloned and amplified using either Mach1 (Thermo Fisher Scientific) or Turbo (New England BioLabs) cells. Unless otherwise noted, plasmid or bacteriophage DNA was amplified using the Illustra TempliPhi 100 Amplification Kit (GE Healthcare Life Sciences) before Sanger sequencing.

Preparation and Transformation of Chemically Competent Cells

Strain S2060 was used in all luciferase, phage propagation, and plaque assays, as well as in all PACE experiments. To prepare competent cells, an overnight culture was diluted 1,000-fold into 50 mL of 2×YT media (United States Biologicals) supplemented with appropriate antibiotics and grown at 37° C. with shaking at 230 r.p.m. to OD600 ~0.4-0.6. Cells were pelleted by centrifugation at 6,000 g for 10 min at 4° C. The cell pellet was then resuspended by gentle stirring in 5 mL of TSS (LB media supplemented with 5% v/v DMSO, 10% w/v PEG 3350, and 20 mM $MgCl_2$). The cell suspension was stirred to mix completely, aliquoted and frozen on dry ice, and stored at −80° C. until use. To transform cells, 100 µl of competent cells were thawed on ice. To this, plasmid (2 µl each of miniprep-quality plasmid prep; up to two plasmids per transformation) and 100 µL KCM solution (100 mM KCl, 30 mM $CaCl_2$), and 50 mM $MgCl_2$ in $H_2O$) were added and stirred gently with a pipette tip. The mixture was incubated on ice for 10 min and heat shocked at 42° C. for 90 s before 850 µl of 2×YT media was added. Cells were allowed to recover at 37° C. with shaking at 230 r.p.m. for 0.75 h, streaked on 2×YT media+1.5% agar (United States Biologicals) plates containing the appropriate antibiotics, and incubated at 37° C. for 16-18 h.

Kinetic Luminescence Assay

S2060 cells were transformed with the luciferase-based activity reporter and tRNA expression plasmids interest as described above. Overnight cultures of single colonies grown in David Rich Medium (DRM) [Bryson, D. I., et al., (2017). Nat. Chem. Biol. December; 13(12):1253-1260] supplemented with maintenance antibiotics were diluted 500-fold into DRM media with maintenance antibiotics in a 96-well 2 mL deep well plate, with or without IPTG inducer. The plate was sealed with a porous sealing film and grown at 37° C. with shaking at 230 r.p.m. for 1 h. 175 µl of cells were transferred to a 96-well black-walled clear-bottom plate (Costar), and then 600 nm absorbance and luminescence were read using an ClarioSTAR (BMG Labtech) over the course of 8 h, during which the cultures were incubated at 37° C.

Calculation of % WT (η).

Begin with three values, the luminescence at OD=0.3 of the WT luciferase positive control (P), the induced tRNA (i), and the suppressed tRNA (s). η=(i−s)/(P−s).

M13 Selection Assay

Grow an overnight culture of the bacteria containing the AP. The next day, dilute culture 1:1000 in 2×YT and aliquot 500 uL each into a deep well 96-well plate. Inoculate each with 10 5 pfu/mL of phage containing the tRNA with randomized anticodon loops. Grow overnight. Filter phage supernatant and plaque activity-independent using pJC175e. Rank selections from lowest ending phage titer to highest ending phage titer. Pick selections for Sanger sequencing including all selections that enrich over 10×, or additional selections as desired. Sanger sequence two plaques for each selection.

Phage Cloning

To clone bacteriophage, PCR fragments were assembled as usual using USER assembly. The annealed fragments are transformed into competent *E. coli* S2060 cells that already bear a plasmid containing pIII under control of the phage shock promoter, pJC175e. Transformants are recovered overnight, centrifuged at 8,000 g for 2 min and supernatant filtered through a 0.22 µm centrifugal filter (Thomas Scientific or Corning). The filtered supernatant containing phage is plaqued, and clonal plaques are expanded overnight and Sanger sequenced.

Manual Phage Plaque Assays

S2060 cells were transformed with the phage activity reporters of interest as described above. Overnight cultures of single colonies grown in 2×YT media supplemented with maintenance antibiotics were diluted 1,000-fold into fresh 2×YT media with maintenance antibiotics and grown at 37° C. with shaking at 230 r.p.m. to OD600 ~0.6-0.8 before use. Bacteriophage were serially diluted 100-fold (4 dilutions total) in $H_2O$. 100 µl of cells were added to 100 µl of each phage dilution, and to this 0.85 mL of liquid (70° C.) top agar (2×YT media+0.6% agar) supplemented with 2% Bluogal (Gold Biotechnology) was added and mixed by pipetting up and down once. This mixture was then immediately pipetted onto one quadrant of a quartered Petri dish already containing 2 mL of solidified bottom agar (2×YT media+1.5% agar, no antibiotics). After solidification of the top agar, plates were incubated at 37° C. for 16-18 h.

Robotics-Accelerated Phage Plaque Assays

Follow the same procedure as above, except for plating of the plaque assays is done by a liquid handling robot by plating 20 µl of bacterial culture and 100 µl of phage dilution with 200 µl of soft agar onto a well of a 24-well plate already containing 235 µl of hard agar per well. To prevent premature cooling of soft agar, place the soft agar on the deck in a 70° C. heat block.

Phage Enrichment Assays

S2060 cells were transformed with the phage activity reporters of interest as described above. Overnight cultures of single colonies grown in 2×YT media supplemented with maintenance antibiotics were diluted 1,000-fold into DRM media with maintenance antibiotics and grown at 37° C. with shaking at 230 r.p.m. to OD600 ~0.4-0.6. Cells were then infected with bacteriophage at a starting titer of $10^5$ pfu/mL. Cells were incubated for another 16-18 h at 37° C. with shaking at 230 r.p.m., then centrifuged at 8,000 g for 2 min and filtered through a 0.22 µm PVDF Ultrafree centrifugal filter (Millipore). The filtered supernatant containing phage was removed and stored at 4° C. The phage titer of these samples is measured in an activity-independent using a plaque assay containing *E. coli* bearing pJC175e.

Continuous Flow PACE

Unless otherwise noted, PACE apparatus, including host cell strains, lagoons, chemostats, and media, were all used as previously described [Dickinson, B. C., et al., *Nat. Commun.* 5, 5352 (2014)]. Chemically competent S2060 s were transformed with the phage propagation reporter and MP6 as described above, plated on 2×YT media+1.5% agar supplemented with 25 mM glucose (to prevent induction of mutagenesis) in addition to maintenance antibiotics, and grown at 37° C. for 18-20 h. Four colonies were picked into 1 mL DRM each in a 96-well deep-well plate, and this was diluted five-fold eight times serially into DRM. The plate was sealed with a porous sealing film and grown at 37° C. with shaking at 230 r.p.m. for 16-18 h. Dilutions with OD600 ~0.4-0.8 were then used to inoculate a turbidostat containing 80 mL DRM. The turbidostat maintains the growing culture at OD600 ~0.7-0.8. Prior to bacteriophage infection, lagoons were continuously diluted with culture from the turbidostat at 1 lagoon vol/h and pre-induced with 10 mM arabinose for at least 45 minutes. Samples (500 µL) of the SP population were taken at indicated times from lagoon waste lines. These were centrifuged at 8,000 g for 2 min, and the supernatant was passed through a 0.22 µm PVDF Ultrafree centrifugal filter (Millipore) and stored at 4° C. Lagoon titers were determined by plaque assays using S2060 cells transformed with pJC175e.

Quantification of qtRNA Charging

Each qtRNA was co-expressed with C-terminal 6×His-tagged GFP-151-TAGA in S2060 cells. Four mL cultures were grown for 28 hours at 37° C. in DRM and purified using a Ni-NTA spin column (Qiagen). The resulting product was run on a 12% Bis-Tris PAGE gel (Invitrogen).

Sample Preparation for Mass Spectrometry

Silver stained SDS-PAGE gel lanes were subdivided into 7 regions and cut into ~2 mm squares. These were washed overnight in 50% methanol/water. These were washed once more with 47.5/47.5/5% methanol/water/acetic acid for 2 hours, dehydrated with acetonitrile and dried in a speed-vac. Reduction and alkylation of disulfide bonds was then carried out by the addition of 30 µl 10 mM dithiothreitol (DTT) in 100 mM ammonium bicarbonate for 30 minutes to reduce disulfide bonds. The resulting free cysteine residues were subjected to an alkylation reaction by removal of the DTT solution and the addition of 100 mM iodoacetamide in 100 mM ammonium bicarbonate for 30 minutes to form carbamidomethyl cysteine. These were then sequentially washed with aliquots of acetonitrile, 100 mM ammonium bicarbonate and acetonitrile and dried in a speed-vac. The bands were enzymatically digested by the addition of 300 ng of trypsin (or chymotrypsin for R or K qtRNAs) in 50 mM ammonium bicarbonate to the dried gel pieces for 10 minutes on ice. Depending on the volume of acrylamide, excess ammonium bicarbonate was removed or enough was added to rehydrate the gel pieces. These were allowed to digest overnight at 37 degrees Celsius with gentle shaking. The resulting peptides were extracted by the addition of 50 µl (or more if needed to produce supernatant) of 50 mM ammonium bicarbonate with gentle shaking for 10 minutes. The supernatant from this was collected in a 0.5 ml conical autosampler vial. Two subsequent additions of 47.5/47/5/5 acetonitrile/water/formic acid with gentle shaking for 10 minutes were performed with the supernatant added to the 0.5 ml autosampler vial. Organic solvent was removed and the volumes were reduced to 15 μl using a speed vac for subsequent analyses.

Chromatographic Separations

The digestion extracts were analyzed by reversed phase high performance liquid chromatography (HPLC) using Waters NanoAcquity pumps and autosampler and a ThermoFisher Orbitrap Elite mass spectrometer using a nano flow configuration. A 20 mm×180 micron column packed with 5 micron Symmetry C18 material (Waters) using a flow rate of 15 μl per minute for three minutes was used to trap and wash peptides. These were then eluted onto the analytical column which was a self-packed with 3.6 micron Aeris C18 material (Phenomenex) in a fritted 20 cm×75 micron fused silica tubing pulled to a 5 micron tip. The gradient was isocratic 1% A Buffer for 1 minute 250 nl min −1 with increasing B buffer concentrations to 15% B at 20.5 minutes, 27% B at 31 minutes and 40% B at minutes. The column was washed with high percent B and re-equilibrated between analytical runs for a total cycle time of approximately 53 minutes. Buffer A consisted of 1% formic acid in water and buffer B consisted of 1% formic acid in acetonitrile.

Mass Spectrometry

The mass spectrometer was operated in a dependent data acquisition mode where the 10 most abundant peptides detected in the Orbitrap Elite (ThermoFisher) using full scan mode with a resolution of 240,000 were subjected to daughter ion fragmentation in the linear ion trap. A running list of parent ions was tabulated to an exclusion list to increase the number of peptides analyzed throughout the chromatographic run. The resulting fragmentation spectra were correlated against custom databases using PEAKS Studio X (Bioinformatics Solutions). Calculation of Limit of Detection and relative abundance. The results were matched to a library of GFP variants with each of the 20 canonical amino acids at residue 151. Abundance of each species was quantified by calculating the area under the curve of the ion chromatogram for each peptide precursor. The limit of detection is $10^4$ [AU], the lower limit for area under the curve for a peptide on this instrument.

R2R for generating tRNA diagrams R2R was used to generate tRNA diagrams. R2R is free software available from www.bioinf.uni-leipzig.de/~zasha/R2R/.

Example 9

Rational Engineering of qtRNAs (See Methods Above Herein)

Figure 11A:
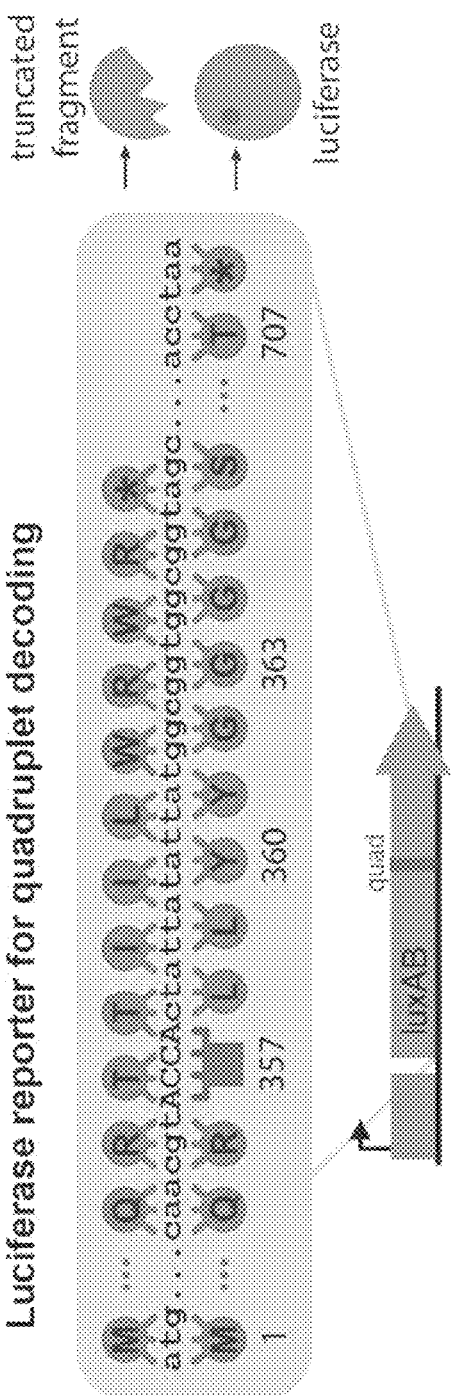
FIG. 11A-D provides schematic diagrams and tables showing a strategy of codon reassignment with rational engineering.

To compare qtRNA translation efficiency, a reporter for quadruplet codon translation was prepared by integrating a single quadruplet codon within the bacterial luciferase luxAB. Failure to decode this quadruplet codon leads to premature termination, whereas successful four base decoding results in full-length luxAB decoding and luminescence. To create a reporter of quadruplet decoding, a quadruplet codon was integrated at permissive residue 357 of a bacterial luciferase, luxAB. In the absence of a functional qtRNA, translation of the luciferase prematurely terminates due to the quadruplet codon generated by the quadruplet codon (top translation). In the presence of a functional qtRNA, full-length luciferase and thereby luminescence is generated (bottom translation) (FIG. 11A).

Figure 11B:
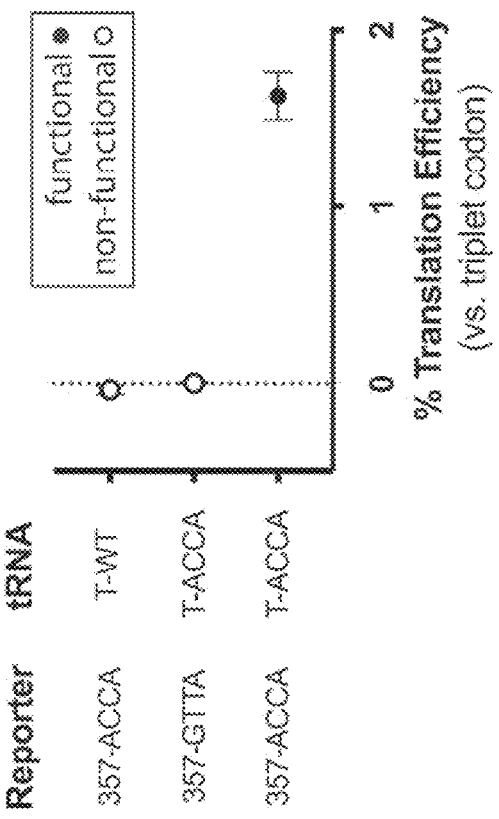

The approach was validated by measuring the quadruplet decoding efficiency of a threonine-ACCA qtRNA reported in the literature. Luminescence was only generated in the presence of the qtRNA and in the presence of a codon-matching reporter. To quantify these data, the increase in luminescence upon induction of the qtRNA was measured, and reported as a fraction of luminescence generated by a wild-type luxAB plasmid, see FIG. 11B. To create a broadly applicable reporter for qtRNAs that integrate chemically diverse amino acids, it was confirmed that residue 357 of luxAB is permissive to every canonical amino acid (FIG. 11B). Luminescence measurements were monitored kinetically, in order to robustly compare toxic and non-toxic qtRNAs, and activity was quantified using luminescence at a standard optical density (OD 600) to account for differential growth rates. Results indicated η, the increase in luminescence upon induction of the qtRNA measured relative to the luminescence of WT-luxAB, which is encoded entirely with triplet codons. This reporter was validated using a previously reported engineered qtRNA [Bossi, L. & Smith, D. M. *Proc. Natl. Acad. Sci. U S. A.* 81, 6105-6109 (1984)], which confirmed that luminescence relies on codon-anticodon interactions and the presence of a qtRNA (FIG. 11B).

Studies were performed using the luciferase reporter to measure the efficiency of known qtRNAs. qtRNAs throughout will be named as "AA identity of tRNA scaffold-codon"; for example a serine tRNA with the 5'-TCTA-3' anticodon is referred to as "5-TAGA". There are seven qtRNAs that have previously been reported in bacteria (Table 2) as well as engineered serine variants (Magliery, T. J., et al., (Edited by M. Gottesman). *J. Mol. Biol.* 307, 755-769 (2001).

TABLE 2 qtRNAs previously reported in bacteria

| Gene | qtRNA | Citation |
| --- | --- | --- |
| sufD | G-GGGG | Riddle, D. L. & Carbon, J. *Nat. New Biol.* 242,, 230-234 (1973); Yourno, J. & Tanemura, S. *Nature* 225, 422-426 (1970) |
| hop R | V-GTNA | O'Connor, M., et al., *EMBO J.* 8, 4315-4323 (1989) |
| sufB | P-CCCC | Sroga, G. E., et al., *Nucleic Acids Res.* 20, 3463-3469 (1992) |
| sufJ | T-ACCN | Bossi and Smith, PNAS *Sci. U.S.A.* 81, 6105-6109 (1984) |
| sufl 6 | G-GGGG | Gaber, R. F. & Culbertson, M. R. *Gene* 19, 163-172 (1982) |
| sufG | Q-CAAA | O'Connor, M. *Nucleic Acids Res.* 30, 1985-1990 (2002) |
| su6 | L-TAGG | Moore, B., et al., *J. Mol. Biol.* 298, 195-209 (2000)) |
| su7 | Q-TAGG | Curran, J. F. & Yarus, M. *Science* 238, 1545-1550 (1987) |

Figure 12B:
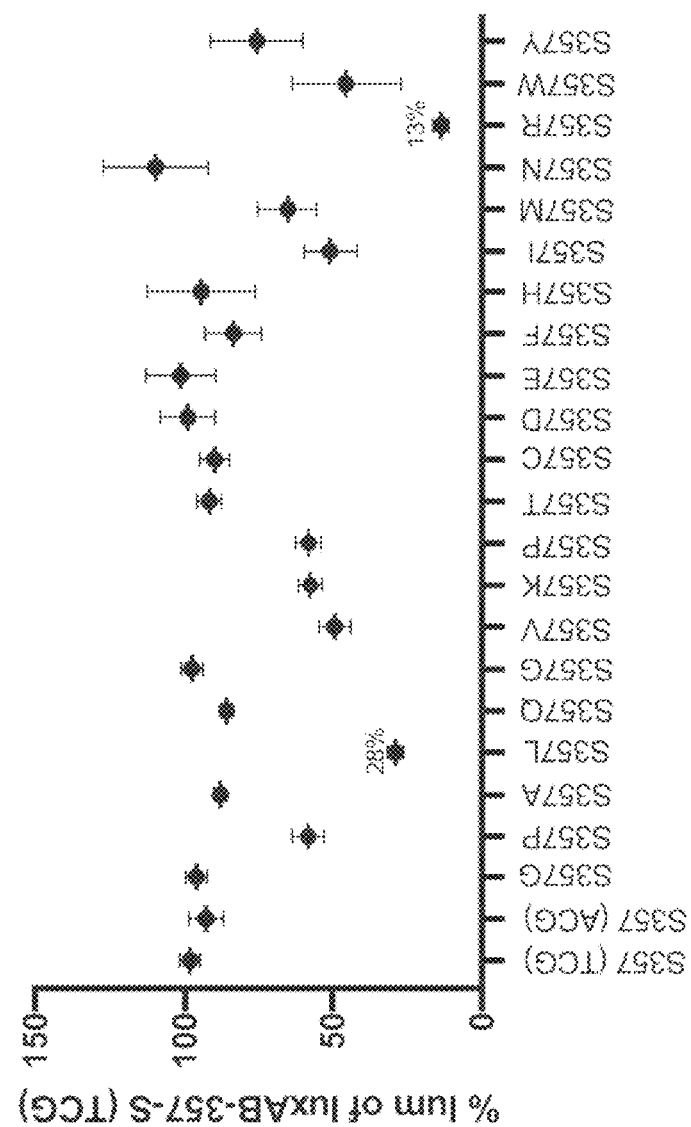
Figure 12A:
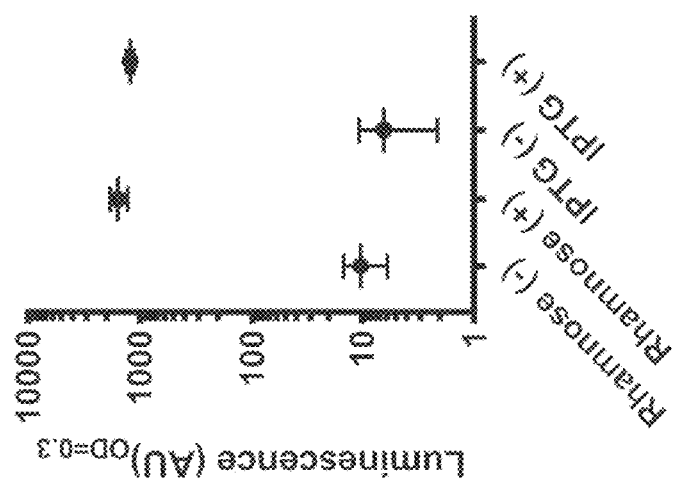

Experiments were performed to measure three of these qtRNAs in S2060 *E. coli* [Hubbard, B. P., et al., (2015) *Nat. Methods* 12, 939-942], a K12 derivative optimized for directed evolution, using luciferase reporters (FIG. 12D).

To expand the catalog of some known qtRNAs to more comprehensively cover canonical amino acid scaffolds, experiments were conducted using rational engineering. Twenty-one representative tRNA scaffolds from the *E. coli* genome were selected, one for each of the 20 canonical amino acids as well as an initiator methionine (Table 3), and techniques were used to convert these tRNAs into functional qtRNAs.

TABLE 3

Table of tRNA scaffolds

| A | Scaffold |
| --- | --- |
| A | |

TABLE 3-continued

Table of tRNA scaffolds

| | |
|---|---|
| A | Alanine tRNA (GGC) 2 |
| C | Cystine (GCA) 1 |
| D | Aspartic Acid (GTC) 1 |
| E | Glu (TTC) 1 |
| F | Phenyalanine (GAA) 1 |
| G | Glycine tRNA (CCC) 1 |
| H | Histidine (GTG) 1 |
| I | Isoleucine (GAT) 1 |
| K | LysQ: Lysine tRNA (UUU) |
| L | LeuX: Leucine tRNA (UAA) 5 |
| M (initiator) | fMet (CAT) 1 |
| M (elongation) | tRNA82 Met |
| N | Asparagine (GTT) 1 |
| P | ProL: Proline tRNA (GGG) 2 |
| Q | Glutamine tRNA (CTG) 1 |
| R | Arginine (ACG) 1 |
| S | SerU: Serine tRNA (CGA) 2 |
| T | ThrT: Threonine tRNA (GGU) 3 |
| V | Val (GAC) 1 |
| W | Trp (CAA) 1 |
| Y | Tyr (GTA) 1 |

Although numerous types of mutations can cause tRNAs to disrupt triplet reading frame maintenance [Atkins, J. F. (2018). *Proc. Natl. Acad. Sci. U.S.A.* 115, 11121-11123], one common motif amongst qtRNAs is an expansion from a 7-base to an 8-base anticodon loop, in which the middle four bases are the new quadruplet anticodon. Two strategies for selecting a new quadruplet codon to replace the triplet codon in qtRNAs of this format were tested.

Figure 11C:
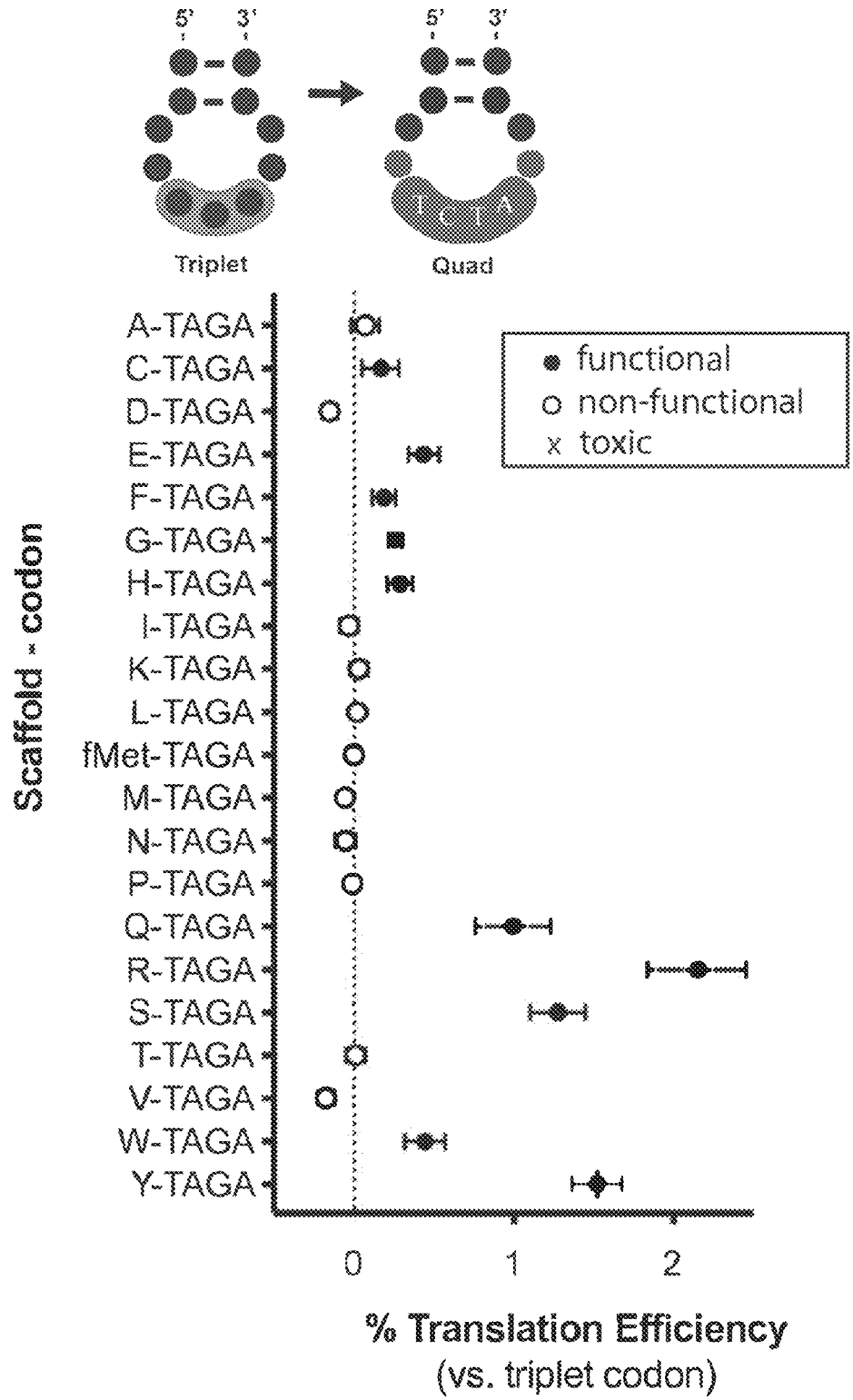

It was believed that TAGA would be a widely functional and efficient quadruplet codon because TAGA-decoding qtRNAs compete with the low-usage triplet stop codon TAG. A complete set of 21 *E. coli* TAGA-decoding qtRNAs was tested by replacing the anticodon in each native tRNA scaffold with 5'-TCTA-3', the reverse complement of TAGA. (FIG. 11C). The efficiency of these qtRNAs was measured using the luciferase reporter (FIG. 11C).

FIG. 11C shows data obtained when a TAGA anticodon was integrated into one scaffold for each of the 20 canonical amino acids and the quadruplet decoding efficiency was measured using a TAGA luciferase reporter. Some of these qtRNA showed decoding of the TAGA codon, at an efficiency of less than 3% of triplet translation. 10/20 of these engineered qtRNAs showed no detectable quadruplet decoding, as indicated by empty circles. The fMet initiator tRNAs was measured with the quadruplet codon integrated at residue 1 of luxAB. 11/21 TAGA qtRNAs showed modest ability to decode TAGA, at less than 2% the efficiency of triplet decoding. With the exception of D-TAGA, these qtRNAs did not cause measurable growth defects, indicating that expression of these qtRNAs is not toxic.

As a second strategy for codon reassignment, it was observed that duplication of the third base of the codon is a common motif in previously discovered qtRNAs (if XYZ is the original codon, XYZZ is the quadruplet codon) [Curran, J. F. & Yarus, M. *Science* 238, 1545-1550 (1987)]; Gaber, R. F. & Culbertson, M. R. *Gene* 19, 163-172 (1982); Moore, B., et al., *J. Mol. Biol.* 298, 195-209 (2000); O'Connor, M. *Nucleic Acids Res.* 30, 1985-1990 (2002); Riddle, D. L. & Carbon, J. *Nat. New Biol.* 242, 230-234 (1973); Sroga, G. E., et al., *Nucleic Acids Res.* 20, 3463-3469 (1992); Yourno, J. & Tanemura, S. *Nature* 225, 422-426 (1970). 18/21 synthetases must charge tRNAs that decode codons with different third bases [Sonneborn, T. M. In *Evolving Genes and Proteins* (eds. Bryson, V. & Vogel, H. J.) 377-397 (Academic Press, 1965)], potentially explaining plasticity in this area of tRNA identity elements. This strategy for codon reassignment minimally disrupts the anticodon because the modification is a point-insertion of a base that already occurs in that area of the tRNA. It was determined that this strategy might minimally disrupt tRNA-AARS recognition making it likely to produce charged qtRNAs. A complete set of XYZZ qtRNAs was tested against luciferase reporters bearing the corresponding codon at residue 357 (FIG. 11C). 6/21 XYZZ generated luminescence at around 2% efficiency. Additionally, 5/21 XYZZ qtRNAs were too toxic to be quantified.

These results showed that not all quadruplet codons could be successfully integrated into all tRNA scaffolds. One potential source of codon-scaffold incompatibility was that these qtRNA rely on host AARSs for aminoacylation, or "charging," the process of attaching an amino acid to the 3' end of the tRNA. All the bacterial AARSs except for L, A, and S rely on identity elements in the anticodon loop to recognize their tRNA, and may be unable to recognize a tRNA with a modified anticodon [Giegé, R., et al., *Nucleic Acids Res.* 26, 5017-5035 (1998)]. If aminoacylation was the only barrier to creation of a functional qtRNA, then all the L, A, and S qtRNAs would be functional. They are not: A-TAGA, L-TAGA, A-GCCC, and L-TTCC are all non-functional. This indicated that interaction with the AARS was not the only barrier to creation of a functional qtRNA. Indeed, adherence to AARS identity elements was not a dominant requirement for qtRNA functionality: the TAGA qtRNAs involved changes to many or all of the bases in the anticodon that were predicted as likely to be very disruptive to tRNA recognition, yet still resulted in functional qtRNAs. Together, there are no clear predictive trends that describe which codons are compatible with which scaffolds, or indeed whether the remaining 9 scaffolds are capable of supporting quadruplet codon translation at all. However, as described in studies set forth herein, testing 42 rationally engineered qtRNAs, resulted in the successful identification of functional qtRNAs based on 12 of the 21 target scaffolds.

Figure 11D:
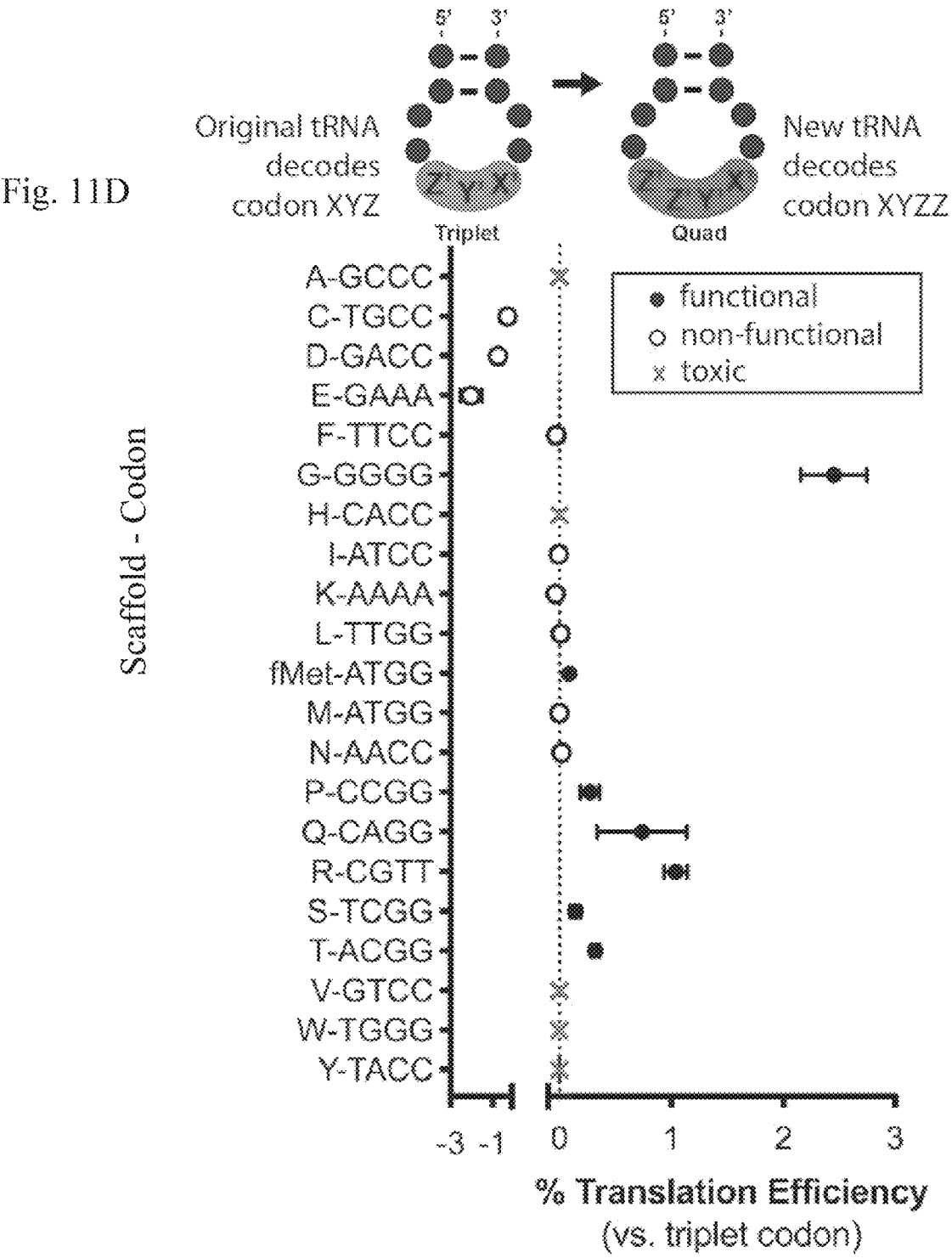

FIG. 11D shows results obtained in experiments that tested reassigning each tRNA to a four-base codon that is related to the codon it canonically decodes through replication of the third base (XYZ→XYZZ). This "XYZZ" anticodon was integrated into one scaffold for each of the 20 canonical amino acids and the quadruplet decoding efficiency was measured using the requisite luciferase reporter. Results indicated that 6/20 showed quadruplet decoding activity, 5/20 were nonfunctional (empty circles), and 9/20 exhibited cellular toxicity so high that it prevented us from quantifying the functionality (red). The fMet initiator tRNAs is measured with the quadruplet codon integrated at residue 1 of luxAB.

Example 10

Identifying and Testing Additional Suppressor tRNA Sequences—a pIII-Based Library Selection for Functional qtRNAs (See Methods Above Herein)

Procedures were carried out to engineer quadruplet decoding tRNA variants for every *E. coli* tRNA. To identify starting points, suppressor tRNAs reported in the literature were tested. Also tested were rationally engineered suppressors using two different codon reassignment strategies, and a library-based selection method was also developed and used. Functional suppressor tRNAs were identified, and further steps were carried out to increase their function.

Overview

Steps in the identification and testing process are shown in FIG. 13A-E. To select for functional qtRNAs amongst a libraries of tRNA with randomized anticodons, a selection approach was developed based upon the M13 bacteriophage tail fiber pIII. pIII is encoded with a quadruplet codon at permissive residue 29. qtRNAs are expressed from the genome of an M13 bacteriophage, from which pIII has been deleted. Only in the presence of a functional qtRNA can full length pIII, and thereby phage propagation, take place. See FIG. 13A.

The reporter was validated using two highly active qtRNAs that had been identified: R-CGTT and R-TAGA. Phage bearing both these qtRNAs are capable of forming plaques when challenged to infect E. coli bearing a phage propagation reporter with a matching quadruplet codon; control experiments with mismatched quadruplet anticodons or lacking the qtRNA confirmed the requirements for cognate nine codon/anticodon interactions for phage propagation. Controls included: pIII reporter positive control—E. coli that supply pIII in response to phage infection using pIII encoded under control of the phage shock promoter; pIII reporter negative control—S2060 E. coli lacking any plasmid bearing pIII; M13 phage positive control—a M13 phage that retains pIII on its genome; M13 negative control—M13 ΔpIII. See FIG. 13B.

Fold enrichment of clonal phage bearing the nine most efficient TAGA qtRNAs clonal phage was compared to the efficiency of each qtRNA in a luciferase assay. It was determined that translation efficiency trended with phage enrichment. See FIG. 13C.

Each of eight different clonal pIII reporters were crossed separately against each of 20 different 256-tRNA libraries, for a total of 160 separate library selections. See FIG. 13D.

Figure 13A:
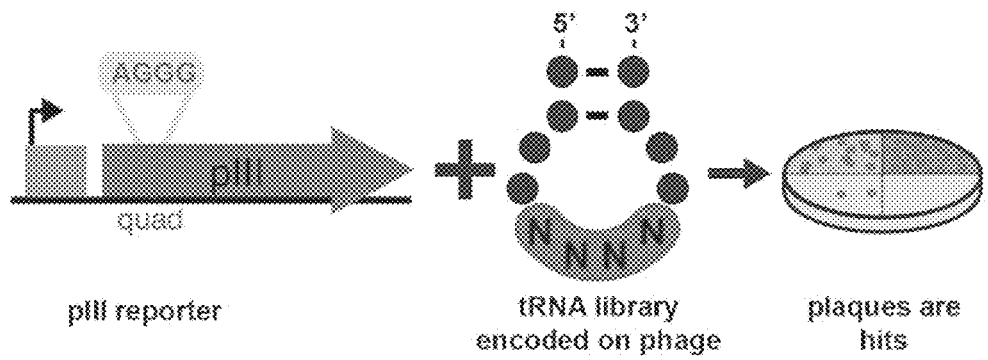
FIG. 13A-E provides schematic diagrams, images and graphs of results from studies including codon reassignment with pIII library selection.
Figure 13B:
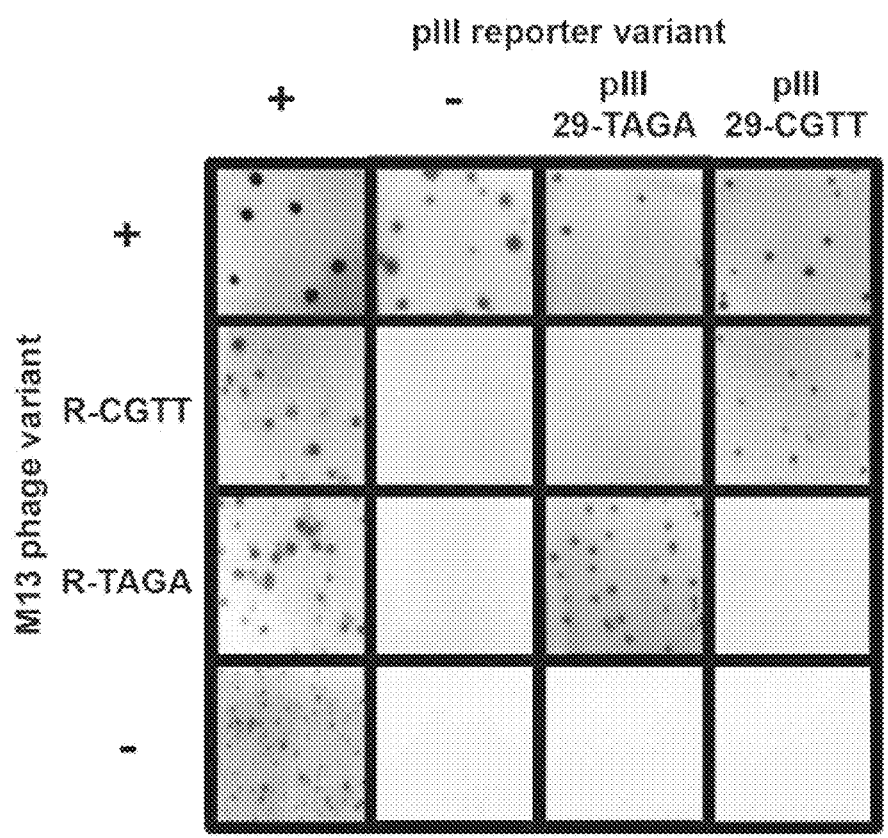
Figure 13C:
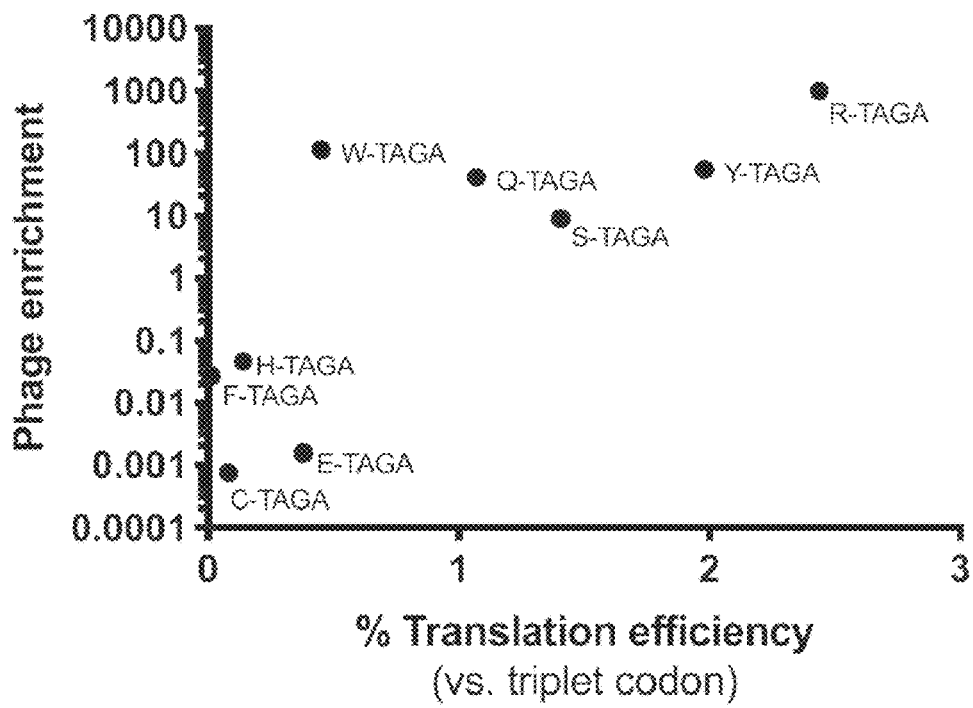
Figure 13D:
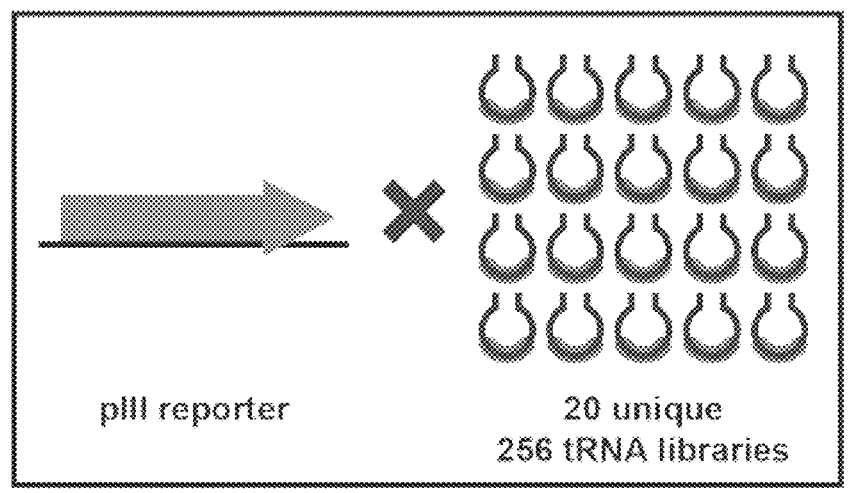
Figure 13E:
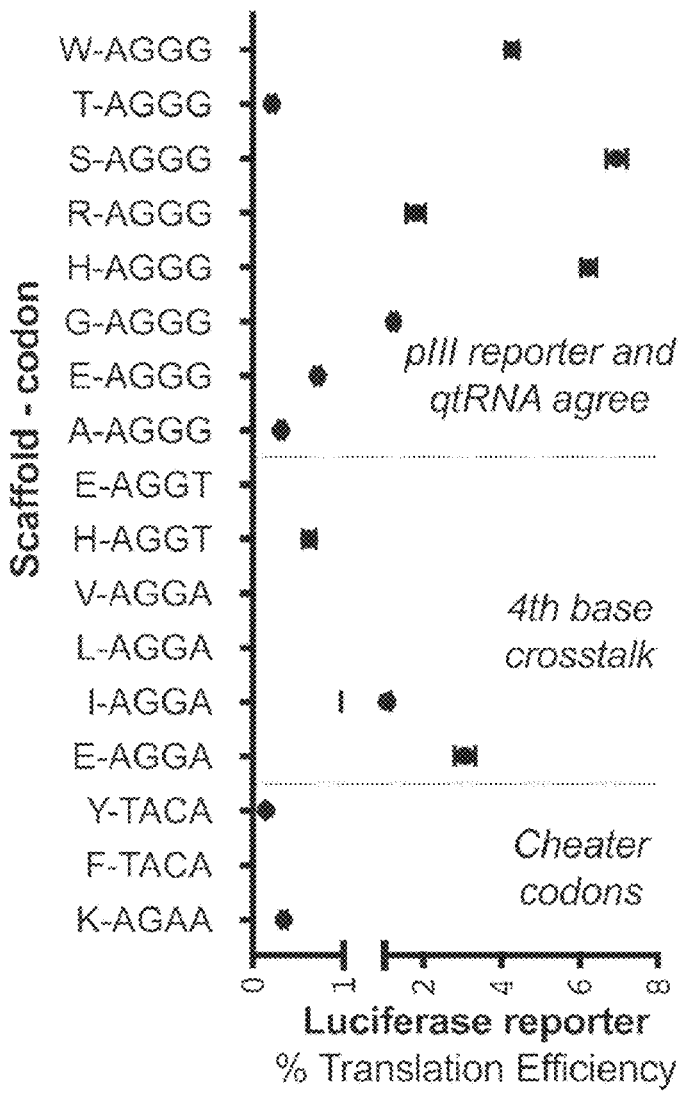

Example results for the AGGG reporter are shown in FIG. 13E. In this study 20 separate tRNA-NNNN libraries were enriched against the pIII-29-AGGG reporter and sequenced plaques from libraries showing high enrichment. qtRNA hits were subcloned into the tRNA expression plasmid and validated using the luminescence reporter. Identified hits fall into three categories: qtRNAs that decode AGGG, qtRNAs that decode quadruplet codons that mismatch from the codon in the reporter at the fourth position, and qtRNAs that decode other codons nearby residue 29 (see FIG. 14 for a map of cheater locations). For results for the other 7 quadruplet codons are shown in FIG. 14.

General Methods—Also See Methods Above Herein

A number of suppressor tRNAs were developed, engineered, and tested. Sequences that encode functional suppressor tRNAs were identified and are set forth herein as SEQ ID NOs: 28-67. Each of SEQ ID NOs: 28-67 was tested as described above herein for toxicity and function, and all were determined to be functional. FIG. 9A includes SEQ ID NOs: 28-67 and indicates each as: minimally functional or functional. These experiments also identified additional sequences encoding suppressor tRNAs, which are set forth herein as SEQ ID NO: 68-87. These additional sequences were tested as described above herein, and the toxicity and/or function of each was determined. Each of SEQ ID NOs: 68-87 was determined to be extremely toxic and/or non-functional. FIG. 9B includes SEQ ID NOs: 68-87 and indicates each as: extremely toxic or nonfunctional. In addition to naïve sequences SEQ ID NOs: 28-87, ten sequences, SEQ ID NO: 88-97, were evolved sequences.

With 20 different tRNA scaffolds and 256 possible quadruplet codons, there are 5120 possible scaffold-codon pairs. A major limitation of the rational engineering approach is that it requires a guess-and-check approach to individual scaffold-codon assignments, many of which are nonfunctional. To more efficiently navigate the space of possible codon reassignments, studies were performed using a library-based approach in which functional qtRNAs were selected using a quadruplet-dependent reporter from 20 different qtRNA-NNNN libraries, each containing a degenerate anticodon pool. This approach allowed rapid assessment of the efficiency of numerous scaffold-codon pairs.

For the studies pIII, the tail fiber of the M13 bacteriophage, was chosen as the basis for the reporter. A single quadruplet codon was integrated at permissive residue pIII-P29 [Bryson, D. I., et al., (2017). Nat. Chem. Biol. December; 13(12):1253-1260], which created a reporter that tied quadruplet codon translation to M13 phage propagation (FIG. 13A). FIG. 13A, illustrates a strategy used to select for functional qtRNAs amongst a libraries of tRNA with randomized anticodons, in which a selection was developed based upon the M13 bacteriophage tail fiber pIII. pIII is encoded with a quadruplet codon at permissive residue 29. qtRNAs are expressed from the genome of an M13 bacteriophage, from which pIII has been deleted. Only in the presence of a functional qtRNA can full length pIII, and thereby phage propagation, take place.

FIG. 13B shows validation data obtained for this reporter using two highly active qtRNAs that were identified: R-CGTT and R-TAGA. Phage bearing both these qtRNAs were determined to be capable of forming plaques when challenged to infect E. coli bearing a phage propagation reporter with a matching quadruplet codon; control experiments with mismatched quadruplet anticodons or lacking the qtRNA confirmed the requirements for cognate codon/anticodon interactions for phage propagation. Controls included: pIII reporter positive control—E. coli that supply pIII in response to phage infection using pIII encoded under control of the phage shock promoter; pIII reporter negative control—S2060 E. coli lacking any plasmid bearing pIII; M13 phage positive control—a M13 phage that retains pIII on its genome; M13 negative control—M13 ΔpIII. The qtRNA was expressed from the M13 phage genome. When challenged to infect E. coli bearing the pIII reporter plasmid, functional phage were produced in proportion to quadruplet codon translation. This reporter was validated by integrating a CGTT or TAGA quadruplet codon at pIII-29 and it was verified that phage bearing the R-CGTT or R-TAGA qtRNAs showed phage propagation in the form of plaquing, and phage lacking a functional or matching qtRNA did not plaque (FIG. 13B).

To further validate this approach, studies were performed using the nine most efficient TAGA qtRNAs to confirm that efficiency measured by the luminescence reporter correlated with phage enrichment (FIG. 13C). These results confirmed that M13 phage propagation was linked to qtRNA translation efficiency. FIG. 13C shows validation results obtained by comparing fold enrichment of clonal phage bearing the nine most efficient TAGA qtRNAs clonal phage to the efficiency of each qtRNA in a luciferase assay. Results demonstrated that translation efficiency trended with phage enrichment.

This reporter was used in studies to identify functional codon-scaffold pairs by using it to enrich functional qtRNAs from a library. Eight quadruplet codons were selected for testing, each of which corresponds to a functional XYZZ qtRNA, which was expected to be re-discovered as a positive control. For each codon, each of 20 qtRNA-NNNN phage libraries was enriched against the pIII reporter, effectively surveying 8×20=160 codon reassignments (FIG. 13D). FIG. 13D is a diagram showing selections performed with pIII reporter. In these studies each of eight different clonal pIII reporters was crossed separately against each of 20 different 256-tRNA libraries, for a total of 160 separate library selections.

Clonal phage from both high and low titer enrichments were Sanger sequenced. It was determined that high titer enrichments generally contained qtRNAs bearing anticodons that corresponded to the reporter while low titer enrichments were populated with the remnants of phage from the input library, with random anticodons (FIG. 14B-C). qtRNA hits were subcloned into the plasmid expression backbone for measurement using luciferase reporters. FIG. 14B provides results of a study in which a library of tRNAs for every canonical amino acid was crossed with eight different M13-selection reporters. The fold enrichment or de-enrichment was calculated relative to the input phage titer for each selection. FIG. 14C provides results of experiments in which, for every filled square, two plaques were Sanger sequenced in order to determine the anticodon identity. Results included instances in which the qtRNAs matched the reporter with four (FIG. 14C Column. AGGG: rows A, E, G, H, R, S, T, and W; Column CCGG: row Y; Column CAGG: rows A, L, Q, and Y; and Column CGGT: rows E, L, M3, R, and V) or the first three (FIG. 14C Column AGGG: rows I, L, and V; Column GGGG: rows A, G, and W; Column CAGG: row H, and Column CGGT: rows A, C, F, and S) bases, instances in which qtRNAs were discovered that suppressed a different quadruplet codon nearby residue 29 (TACA, AGAA, GCAT), or instances in which the qtRNA anticodon was unrelated to the reporter codon (mismatch).

Figure 14A:
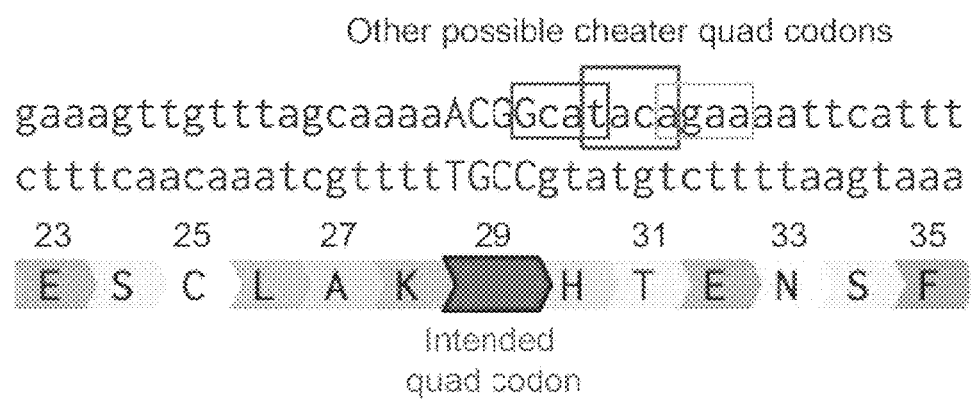
Figure 14B:
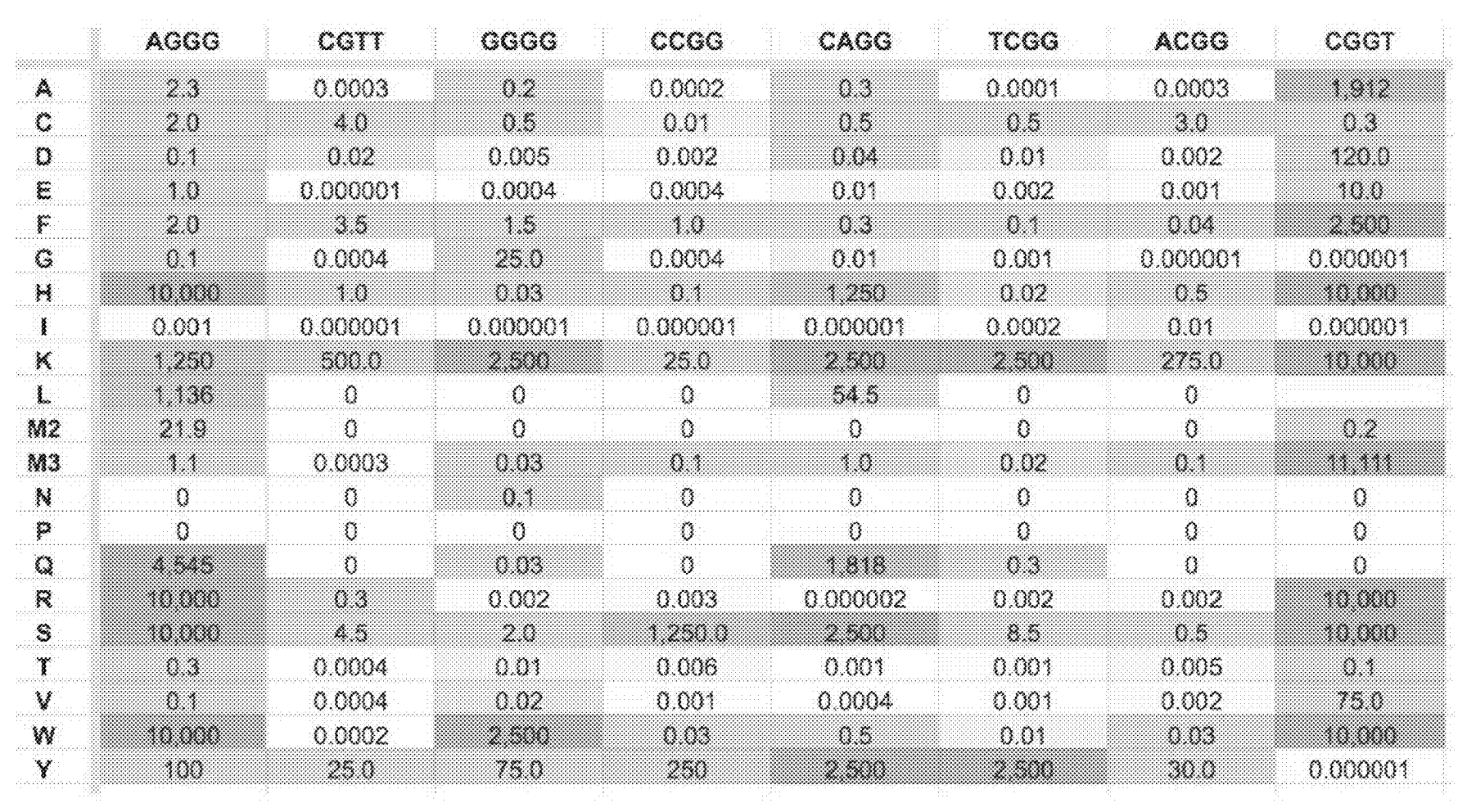

FIG. 13E provides example results for the AGGG reporter. In the studies, 20 separate tRNA-NNNN libraries were enriched against the pIII-29-AGGG reporter and plaques from libraries showing high enrichment were sequenced. qtRNA hits were subcloned into the tRNA expression plasmid and validated using the luminescence reporter. Hits fell into three categories: qtRNAs that decoded AGGG, qtRNAs that decoded quadruplet codons that mismatch from the codon in the reporter at the fourth position, and qtRNAs that decoded other codons nearby residue 29 (see FIG. 16 for a map of cheater locations). For results for the other 7 quadruplet codons, see FIG. 16. In analyzing results, it was determined that there were three categories of hits (FIG. 13E). First were hits where the codon and anticodon were exactly complementary. Second were hits where the codon and anticodon mismatched at the fourth base of the codon. These results corroborated previous reports that qtRNAs crosstalk with quadruplet codons that are mismatched at the fourth base (Anderson, J. C., Magliery, T. J. & Schultz, P. G. Chem. Biol. 9, 237-244 (2002); Curran, J. F. & Yarus, M. Science 238, 1545-1550 (1987); Fagan, C. E., et al., RNA 20, 1944-1954 (2014); Gaber, R. F. & Culbertson, M. R. Mol. Cell. Biol. 4, 2052-2061 (1984). Third, some 'cheater' hits were identified that appeared to decode a four-base codon that is near residue 29 but not the intended quadruplet codon (FIG. 14A). FIG. 14A illustrates certain cheater solutions that were identified. Although the intention was for the phage to suppress the quadruplet codon located at permissive residue 29 of pIII, in many instances the selection identified cheater solutions that suppressed a nearby quadruplet codon instead. In some cases, the cheater hits are functional qtRNAs based on scaffolds for which a functional qtRNA had otherwise not been found, such as K-AGAA.

Studies were performed to check whether this approach had successfully re-identified known qtRNAs from previous approaches. Each of the eight codons elected corresponded to a known XYZZ qtRNA. 6/8 of these qtRNAs were re-identified. Re-discovery of S-TCGG was occluded by more potent enrichment of S-GCAT. The remaining qtRNA, T-ACGG, was the lowest efficiency of the eight at 0.3% of WT efficiency. These data indicate that there may be functional qtRNAs at or below the 0.3% threshold that this assay cannot reliably identify, but above this threshold it reliably identifies functional qtRNAs. Two qtRNAs discovered in this method are toxic when expressed from a plasmid; this is because M13 selections favor variants that promote phage propagation, not cell viability. It was found that AGGG-decoding qtRNAs were more efficient than the other qtRNAs that were discovered, at up to 7% of WT. In general, this approach was an effective way to rapidly identify the most functional qtRNAs from 160 unique reassignment choices, and the efforts to this point yielded functional qtRNAs based on 18 of the 21 target scaffolds.

Figure 12F:
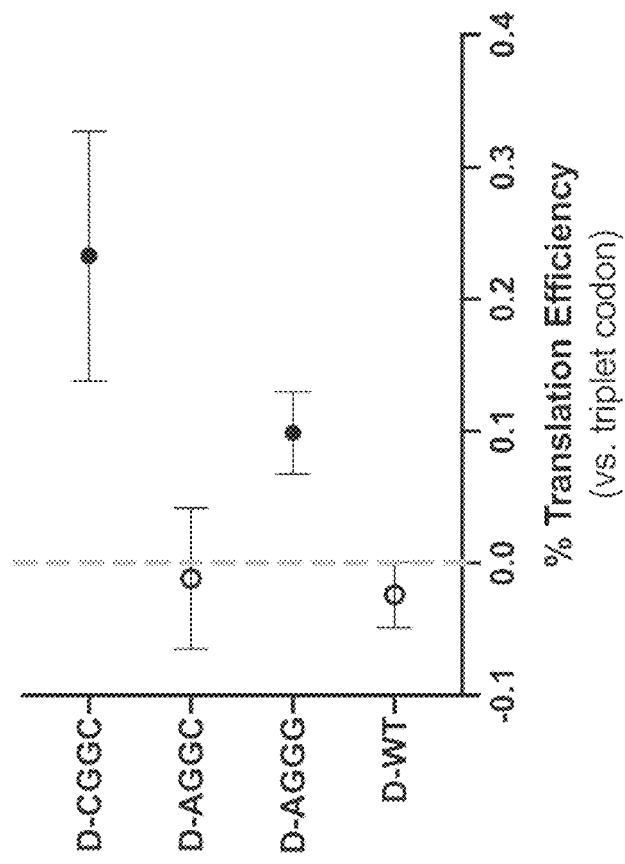
Figure 12G:
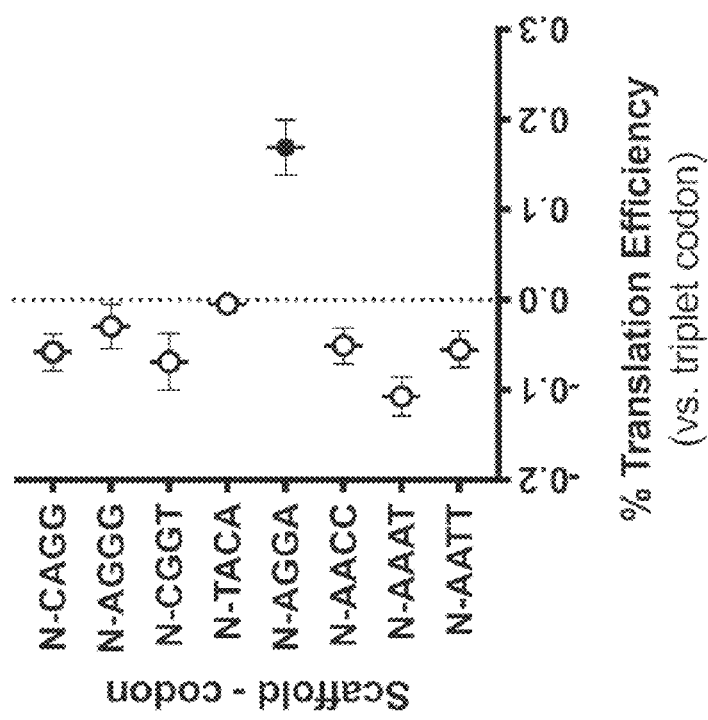

The only three scaffolds for which a qtRNA had not been identified were asparagine (N), aspartic acid (D), and elongation methionine (M). It was found that AGGG created a functional aspartic acid and elongation methionine qtRNAs (FIG. 12E and FIG. 12G). FIG. 12E shows results obtained from testing three codons (TAGA, ATGG, and AGGG) against three different methionine tRNA scaffolds (fMet initiator, tRNA82 referred to as "M2" and tRNA31 referred to as "M3"). Luminescence assays for fMet were performed with the quadruplet codon integrated at residue 1. FIG. 12G shows results of brute force codon reassignment for aspartic acid, which revealed AGGG to be a functional qtRNA. Additional rationally designed codons for N were screened and it was found that AGGA created a functional qtRNA in this scaffold, while all other codons tested, including TAGA and AGGG, did not (FIG. 12F). FIG. 12F shows results of experiment that included brute force codon reassignment for asparagine, with the results revealing that AGGA is a functional qtRNA. In total, every tRNA scaffold tested was capable of supporting quadruplet codon translation.

Experiments described herein resulted in the identification of 63 functional novel suppressors and their encoding sequences and also the identification of toxic and/or non-functional suppressors. FIG. 10 provides a chart of results generated in Examples 2 and 10. The squares in the chart identify the results of codon/amino acid combinations tested, with the squares indicating results of the functional testing result as (1) extremely toxic, (2) toxic, (3) non-functional, (4) functional <1% of wildtype, or (5) functional at >1% of wildtype. The results of the studies described herein provide evidence of novel high-activity functional variants that decode quadruplet codons in multiple contexts. The novel sequences set forth herein can be used in methods of the invention, including, but not limited to: methods of genetic code expansion.

Example 11

Directed Evolution of qtRNAs—(See Methods Above Herein)

The majority of the qtRNAs engineered in these studies exhibited very low translation efficiency, at $\eta$=3% or less when compared to a single triplet codon. Translating a peptide of length N entirely encoded with quadruplet codons should scale with $\eta$ N, compounding this inefficiency exponentially and making it currently infeasible to use these qtRNAs in an exclusive quadruplet codon setting. For example, to translate a 70 residue protein using only quadruplet codons with 10% the yield of normal triplet translation should require $11^{-1}$=96.8%.

To address this issue directed evolution of the qtRNAs was used to improve translation efficiency either by optimizing the scaffold for compatibility with the new anticodon in cis Kleina, L. G., et al., *J. Mol. Biol.* 213, 705-717 (1990); Yarus, M. (1982). Science 218, 646-652, or improving charging efficiency by one or more AARSs in trans [Salazar, J. C., et al., (2003) Proc. Natl. Acad. Sci. U.S.A. 100, 13863-13868]. To investigate these possibilities, a directed evolution platform was created for optimizing translation components for quadruplet decoding and applied it to qtRNAs.

Figure 15A:
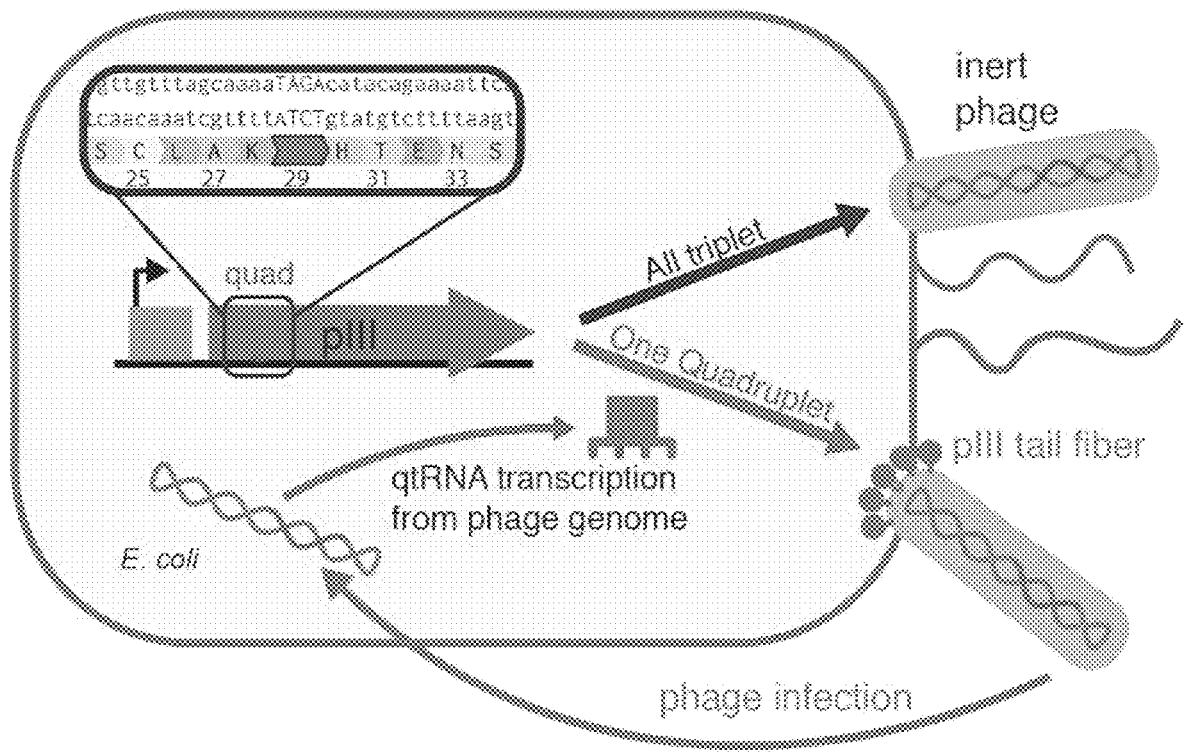
FIG. 15A-C provides schematic diagrams and graphs of a strategy for directed evolution of qtRNAs demonstrating that the directed evolution improves quadruplet decoding.

To evolve a qtRNA, the pIII reporter was used to repeatedly enrich populations of phage for functional variants (FIG. 15A). FIG. 15A is a schematic diagram of an example of an M13-based selection for functional qtRNAs that was used in studies described herein. pIII, the essential M13 phage tail fiber protein, was encoded with a four-base-codon at permissive residue 29. In the presence of a functional qtRNA, full-length pIII was produced. A library of qtRNAs with randomized NNNN anticodons was encoded on the genome of an M13 phage, from which the wildtype copy of pIII had been deleted. Phage were challenged to produce infectious progeny when infecting *E. coli* bearing the reporter plasmid. Successful decoding of the quadruplet codon resulted in translation of full-length pIII and thereby infectious phage progeny. Failure to decode the quadruplet codon resulted in a change of ORF, premature termination, and a truncated, non-functional pIII.

During phage infection and replication, mutations arise in the phage genome, some of which may occur in the qtRNA. Studies included use of an inducible mutagenesis plasmid [Badran, A. H. & Liu, D. R. *Nat. Commun.* 6, 8425 (2015)] to elevate this mutation rate to levels that rival that of traditional in vitro mutagenesis. Thus, repeated enrichment of phage in *E. coli* carrying a pIII reporter construct resulted in directed evolution of the qtRNA. This technique, known as Phage Assisted Continuous Evolution (PACE) [Esvelt, K. M., et al., *Nature* 472, 499-503 (2011)], has been used previously to evolve a wide variety of biomolecule activities including aminoacyl tRNA synthetases [Bryson, D. I., et al., (2017). Nat. Chem. Biol. December; 13(12):1253-1260], biosensors [Pu, J., Zinkus-Boltz, J. & Dickinson, B. C. *Nat. Chem. Biol.* 13, 432-438 (2017)], antibody solubility [Wang, T., et al., (2018) Nat. Chem. Biol. 14, 972-980], broad-PAM specificity Cas9 variants [Hu, J. H., et al., (2018). Nature April 5; 556(7699):57-63], and base editors [Thuronyi, B. W., et al., (2019) Nat. Biotechnol. September; 37(9):1070-1079]. PACE uses a biological process to automate the traditional directed evolution workflow, compressing the multi-day process of library creation and screening into the rapid 20-minute lifecycle of a bacteriophage.

Methods (See Additional Method Details Above Herein)

Figure 16A:
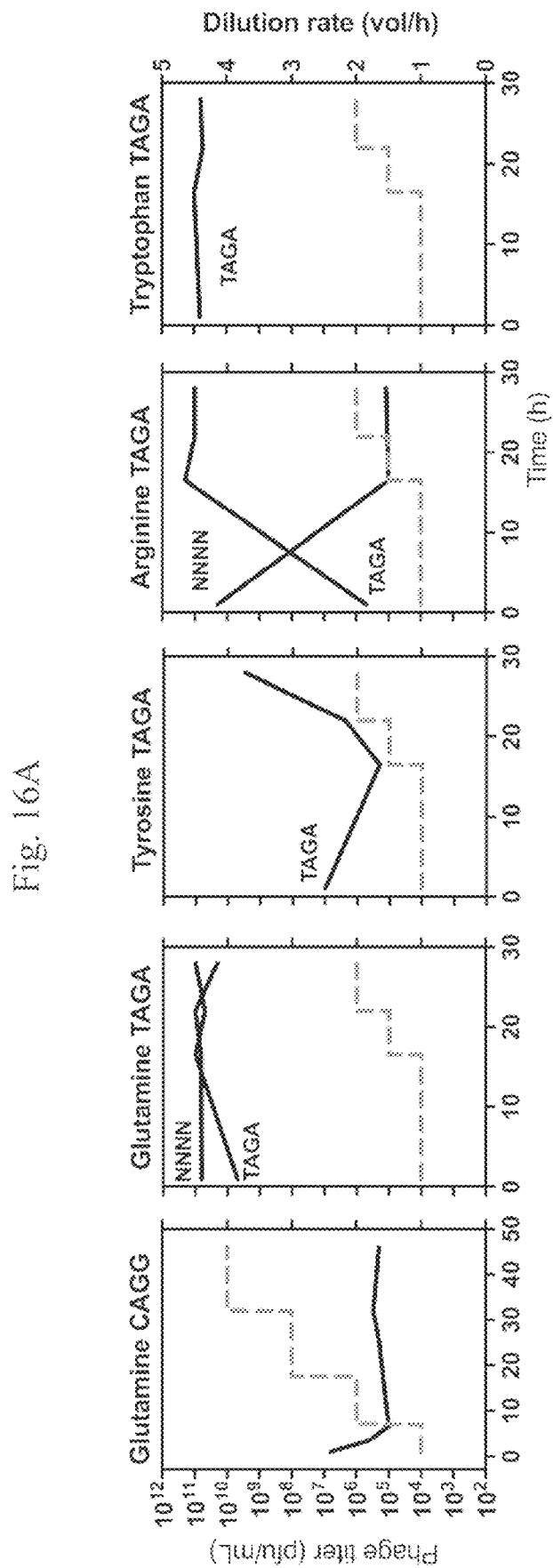
FIG. 16A-E provides graphs and diagrams of various continuous directed evolution experiments.

Phage bearing a Q-NNNN 256-qtRNA library was cultured in continuous flow and the population was challenged to propagate in bacteria bearing the MP6 mutagenesis plasmid [Badran, A. H. & Liu, D. R. *Nat. Commun.* 6, 8425 (2015)] and a pIII reporter containing one CAGG quadruplet codon at permissive residue pIII-29. It was expected that the functional Q-CAGG qtRNA, a member of the inoculating library, would be enriched. Additionally, it was possible that evolved variants of Q-CAGG might also emerge. After 45 hours of continuous culture (FIG. 16A), the population converged upon tRNAs bearing the expected anticodon, and an evolved variant of Q-CAGG, Q-CAGG-Evo1, overtook the population. FIG. 16A provides results of experiments in which five tRNA qtRNAs were evolved in continuous culture. Phage titers (left axis, solid lines) and population dilution rate (right axis, dashed lines) are shown. Phage titers generally remained flat or rose over the course of evolution. In two instances, Q-NNNN and R-NNNN, the experiments were seeded with phage bearing a randomized anticodon loop rather than a clonal variant; in both cases the final population was overtaken by phage bearing the expected anticodon.

Figure 16B:
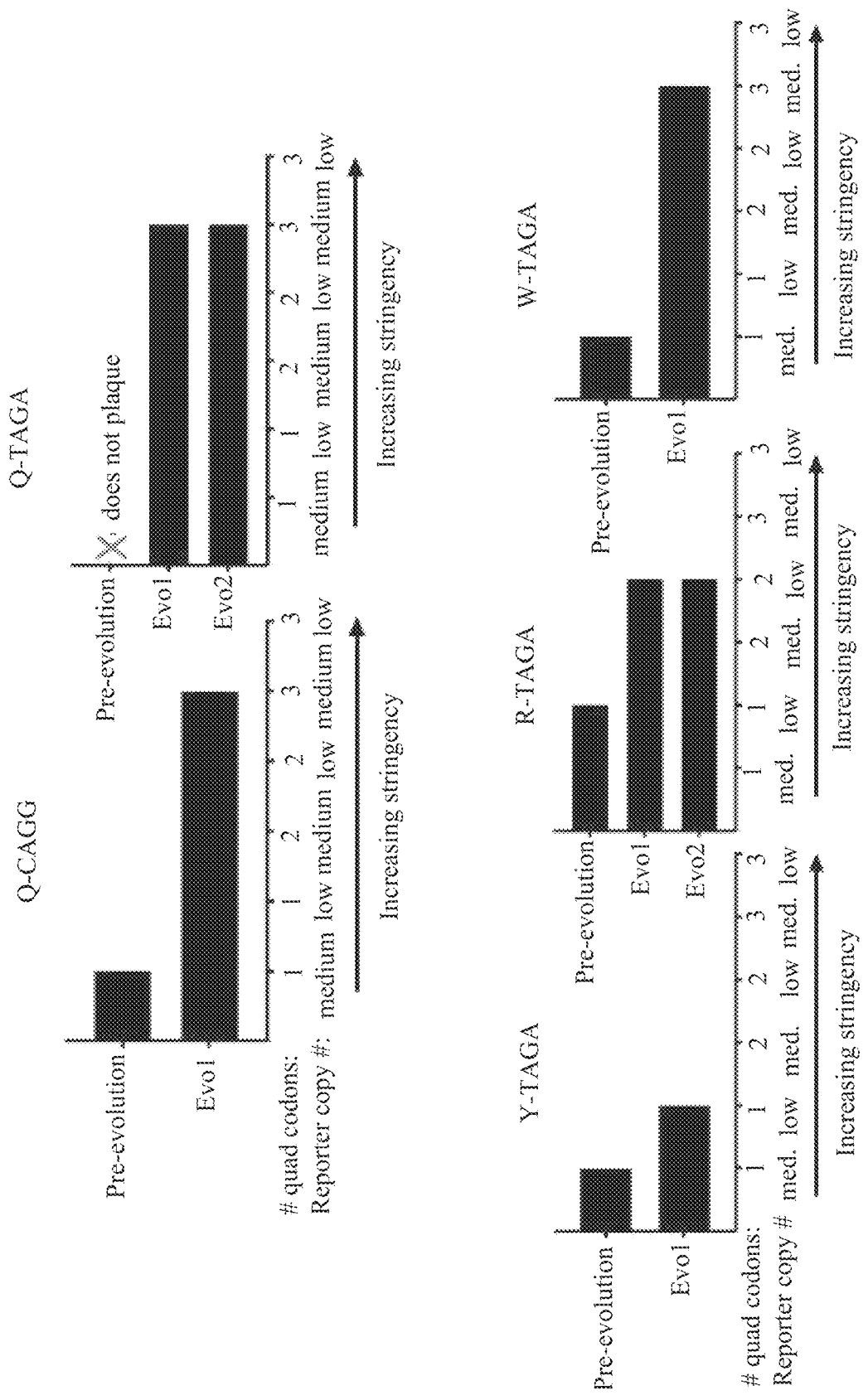

The starting and ending fitness of the phage were compared using enrichment assays, and it was found that the evolved phage bearing Q-CAGG-Evo1 exhibited a substantially improved ability to decode quadruplet codons and was now capable of supporting phage propagation using a copy of pIII containing three quadruplet codons (FIG. 16B). FIG. 16B shows results of testing to determine the results of evolution. In these studies the initial and final tRNA variants were compared against a ladder of phage activity reporters of increasing difficulty. Phage were initially capable of efficiently producing infectious progeny that require production of pIII that contains 1 quadruplet codon; in contrast, the evolved phage were capable of relying on a pIII that requires 3 quadruplet codons. Low copy number reporters, using an SC101 backbone (~4 copies/cell), were more stringent than medium copy number reporters, using a SC101 mutant backbone [~27 E93K copies/cell (Peterson, J. & Phillips et al., *Plasmid* 59, 193-201 (2008)].

However, sequencing revealed that Q-CAGG-Evo1 acquired a point insertion at the 5' side of the anticodon loop (FIG. 16E) resulting in an 9-base anticodon loop, creating a tRNA mutant that did not adhere to the 8-base anticodon loop format under study and that may have different properties. Expression of Q-CAGG-Evo1 from a plasmid was too toxic to permit quantification using a luminescence reporter.

Evolution of toxic biomolecules is a known failure mode of PACE, because selection favors variants that promote phage propagation, not cell viability. From these results, it was conclude that the directed evolution approach is capable of generating qtRNAs with higher efficiency; however full-qtRNA optimization may result in evolved variants that disrupt frame maintenance through diverse mechanisms or exhibit other undesired properties such as high toxicity.

Figure 16C:
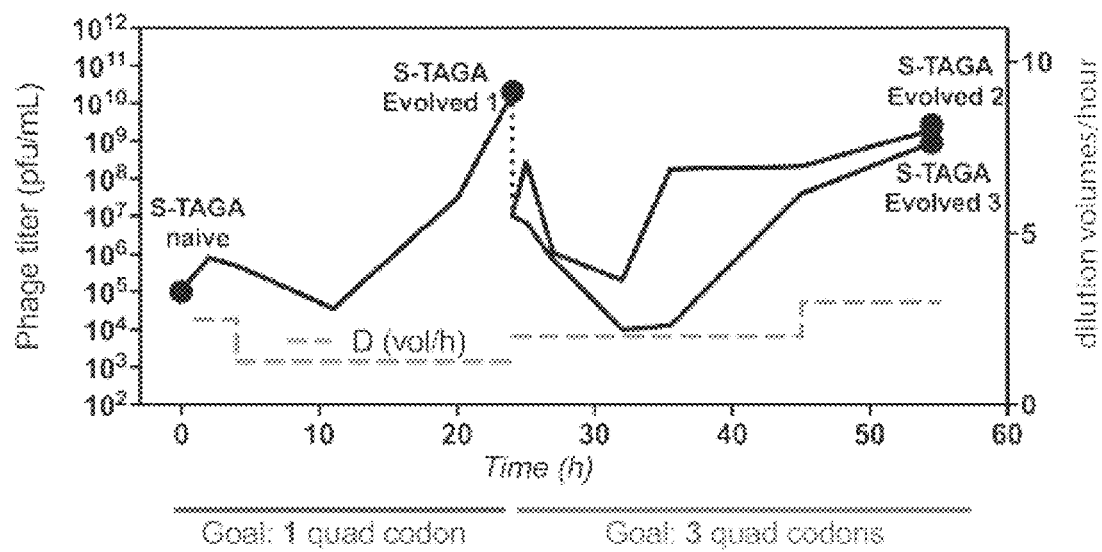
Figure 16D:
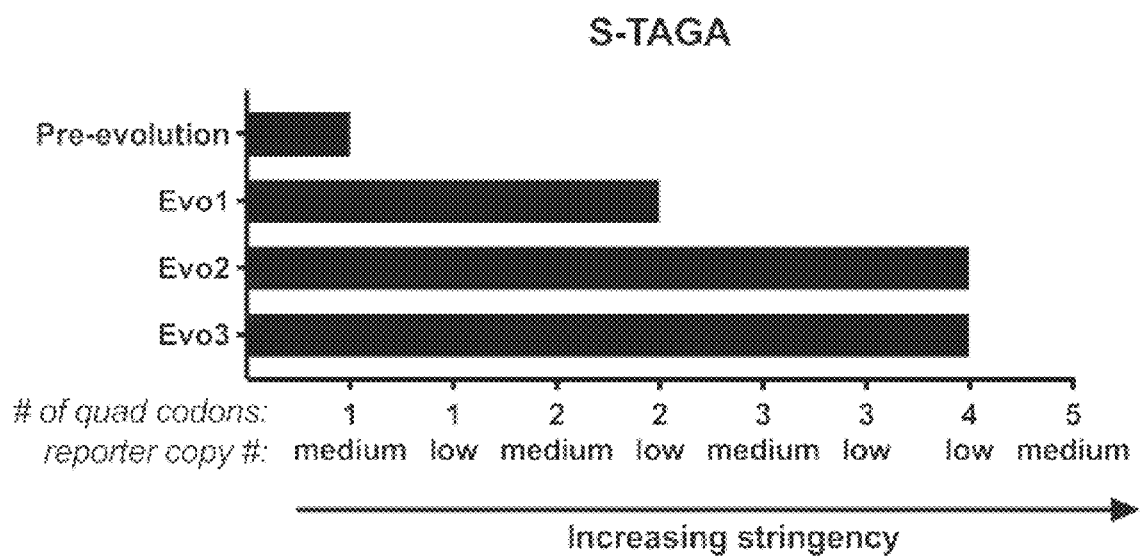
Figure 16E:
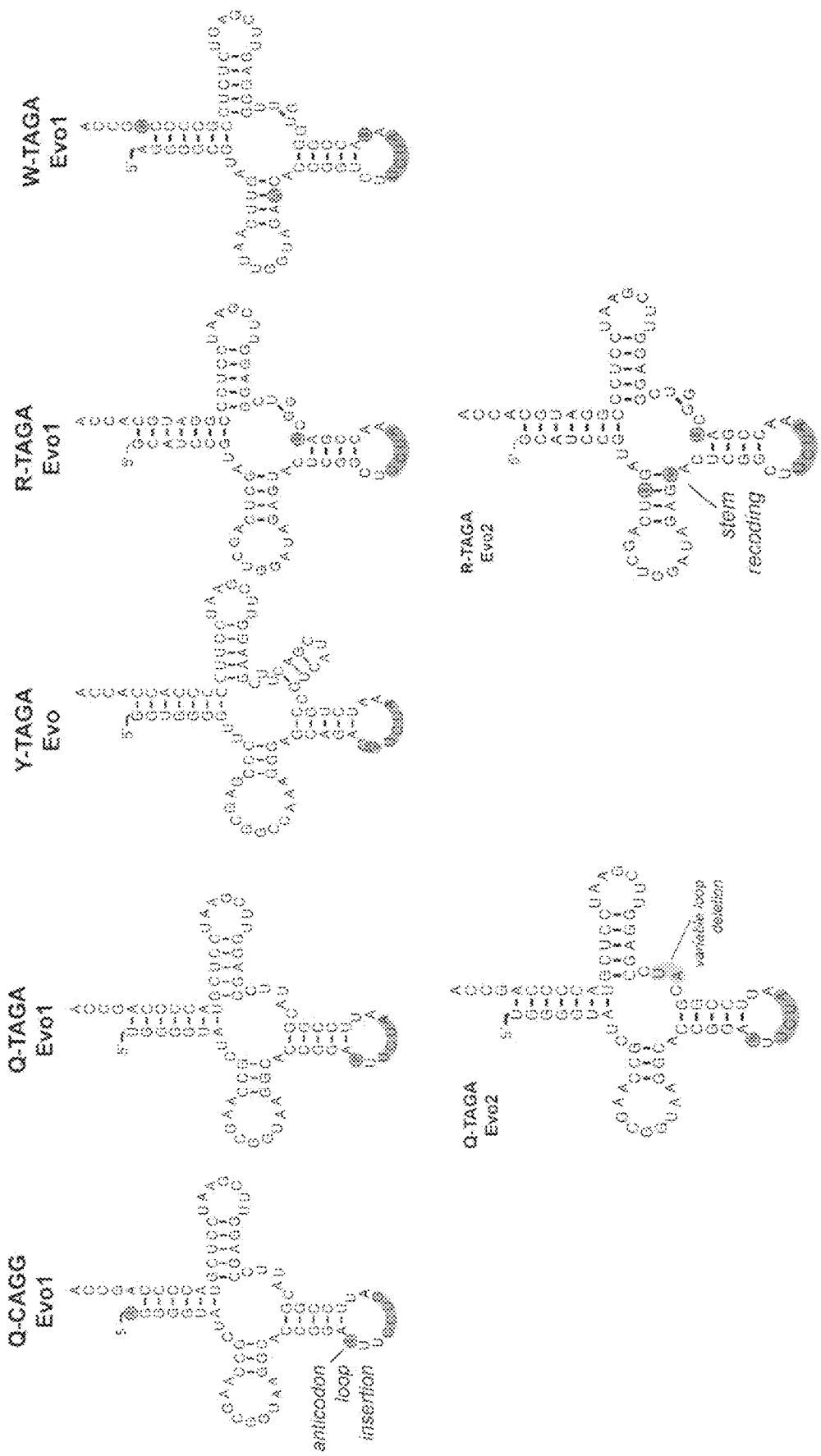

Next, studies were performed to evolve the five most efficient TAGA qtRNAs in continuous flow using the MP6 mutagenesis plasmid and a pIII reporter containing pIII-29-TAGA (FIG. 16A). Some experiments experienced phage washout or evolution of phage-pIII recombinants due to low starting activity. All other experiments, including at least one experiment for every tRNA scaffold tested, evolved qtRNA variants that swept the population; replicate experiments evolved similar mutations. The clonal phage bearing these evolved qtRNAs were characterized and it was determined they all show improved activity (FIG. 16), again supporting phage propagation using a pIII transcript requiring three quadruplet codons. Sanger sequencing revealed that all of these 11 evolved variants retained the usual 8-base anticodon loop characteristic of the format of qtRNAs that was under study (FIG. 16E).

Figure 15B:
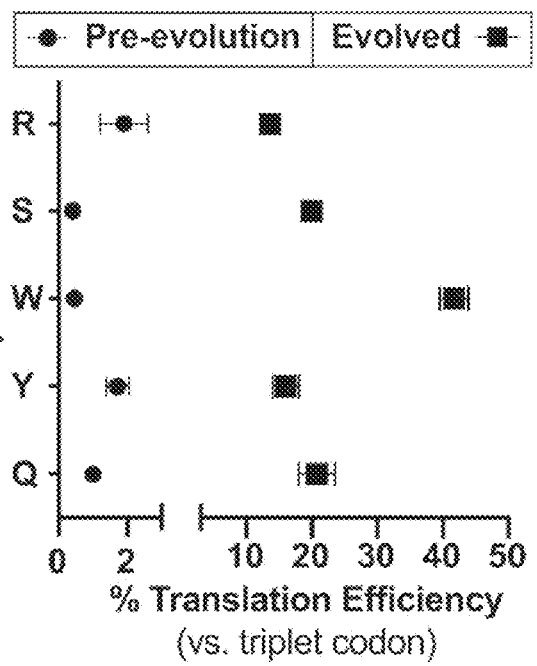

Interestingly, four of the five scaffolds resulted in mutations to the sides of the anticodon loop, however these mutations were not convergent. The evolved S-TAGA variant, S-TAGA-Evo1, replicates the anticodon loop side mutations described in previous engineering of serine-based qtRNAs [Magliery, T. J., et al., (Edited by M. Gottesman). *J. Mol. Biol.* 307, 755-769 (2001)]. Another evolved variant, Y-TAGA-Evo, exhibits a mutation to the highly conserved U33 base just 5' of the anticodon [Salman Ashraf, S., et al., (1999) RNA 5, 503-511], but continues to functionally decode quadruplet codons. The quadruplet decoding efficiency of each evolved qtRNA was compared to its pre-evolution equivalent using the luminescence reporter. Results indicated that evolved variants generally showed about an order of magnitude improvement in quadruplet decoding efficiency (FIG. 15B) without a measurable increase in toxicity. FIG. 15B provides a graph of results of experiments in which evolved tRNA variants were subcloned into the inducible tRNA expression backbone and measured using the luminescence reporter. The efficiency of evolved qtRNAs has improved, as demonstrated by a kinetic luminesce assay.

Studies were performed to determine whether even higher efficiency could be achieved through further evolution on a more difficult evolutionary goal. This was examined by evolving S-TAGA-Evo1 on a substantially more challenging phage pIII reporter in which S16, S29, and S34 were all replaced with TAGA codons. S-TAGA-Evo1 was evolved in continuous flow for 30 hours in the two parallel experiments. Interestingly, it was observed that UAG codons evolved in the phage backbone within the highly expressed phage protein pVIII, suggesting that these qtRNAs crosstalk with the triplet UAG codon. In addition, two sweeping variants arose, S-TAGA-Evo2, S-TAGA-Evo3 (FIG. 16C). FIG. 16C shows results of studies in which the Serine-TAGA qtRNA was evolved in continuous culture, challenging it to decode one quadruplet codon for the first 24 hours and then to decode three quadruplet codons for the final 30 hours. Total phage titer (solid) generally fell and then rose over the course of each segment of the evolution. The population dilution rate (dashed) was used to increase selection pressure during the course of evolution. These evolved variants now showed activity on a pIII reporter requiring four quadruplet codons (FIG. 16D). FIG. 16D shows results of experiments in which the initial and final qtRNA variants were compared against a ladder of phage activity reporters of increasing difficulty. Evolved phage were capable of relying on a pIII that required 4 quadruplet codons.

Historically, translation efficiency of qtRNAs has been broadly lower than TAG-suppression, motivating the field to focus on stop codon suppression [Dumas, A., et al., (2015). Chem. Sci. 6, 50-69]. However, analysis of these variants using the luminescence reporter showed that the most evolved qtRNA variant decodes the TAGA quadruplet codon at the same efficiency that the commonly used *M. jannaschii* Y-TAG tRNA [Link, A. J., et al., (2003) *Curr. Opin. Biotechnol.* 14, 603-609] decodes the triplet TAG codon (FIG. 15B).

From the results of these studies it was concluded that directed evolution of the tRNAs themselves can substantially improve activity in some cases. In particular, although qtRNAs with modified anticodons alone are generally inefficient, translating at <3% the efficiency of a triplet codon, their evolved variants can translate at ~30% efficiency. Although η=30% still represents a severe translation efficiency penalty relative to triplet codons, it also corresponds to an exponential improvement when using these evolved qtRNAs in an exclusively quadruplet-codon setting. These efficiency improvements may make it feasible to translate peptides entirely using quadruplet codons that can be meaningfully tied to selection in directed evolution campaigns.

Figure 15C:
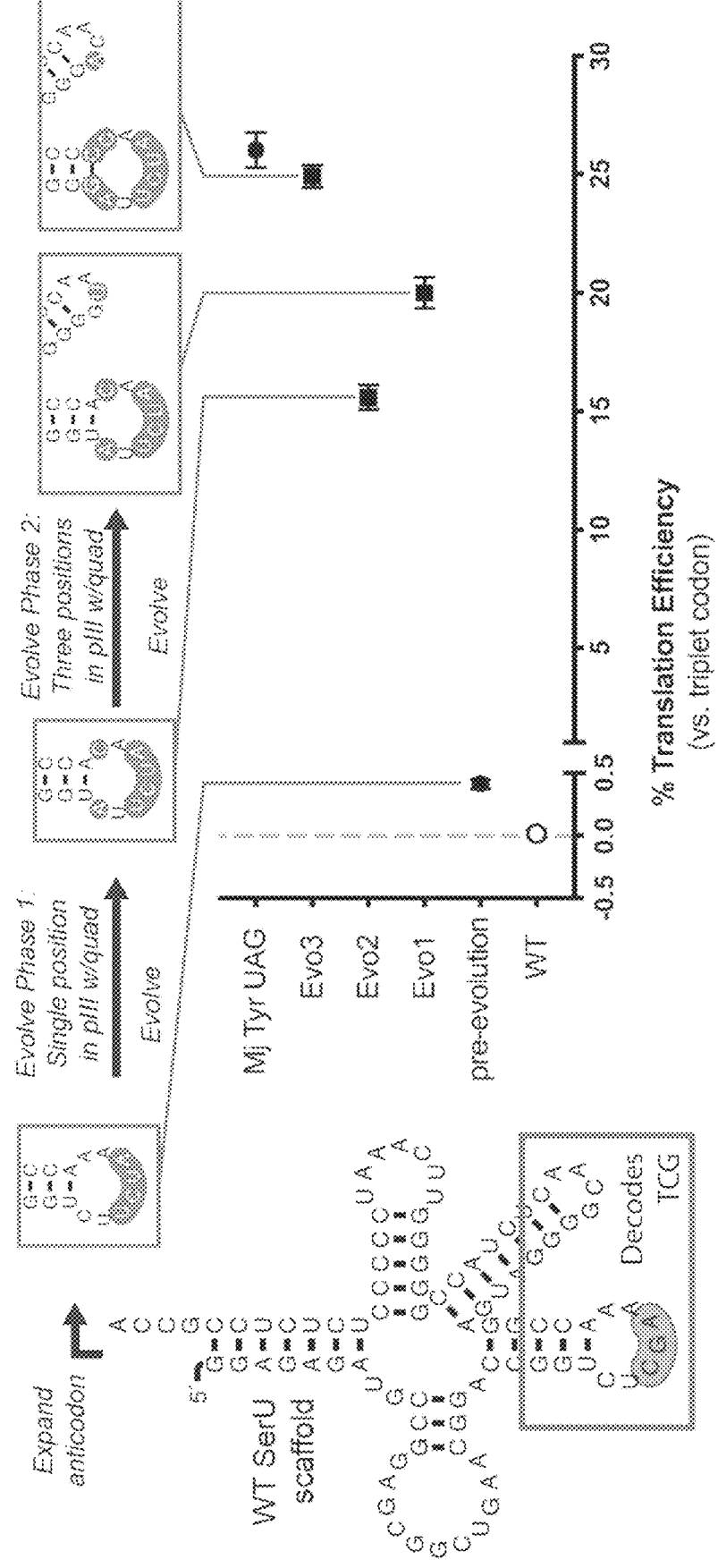

Studies that included additional evolution on a harder goal were performed and results showed further improvement in the further evolved qtRNA. FIG. 15C shows results obtained in a study in which the Serine-TAGA qtRNA was evolved in multiple rounds of evolution with increasingly challenging evolution goals. The first phase of evolution challenged phage to utilize a pIII variant with a single TAGA integrated at residue 29. The second phase of evolution challenged phage to utilize a pIII variant with TAGA codons integrated at residues 16, 29, and 34. The second phase of evolution produced additional mutations. The most evolved qtRNA variants perform on-par with the Mj-Tyr tRNA/AARS pair in decoding TAG codons.

Example 12

Analysis of qtRNA Charging—(See Methods Above Herein).

Figure 17A:
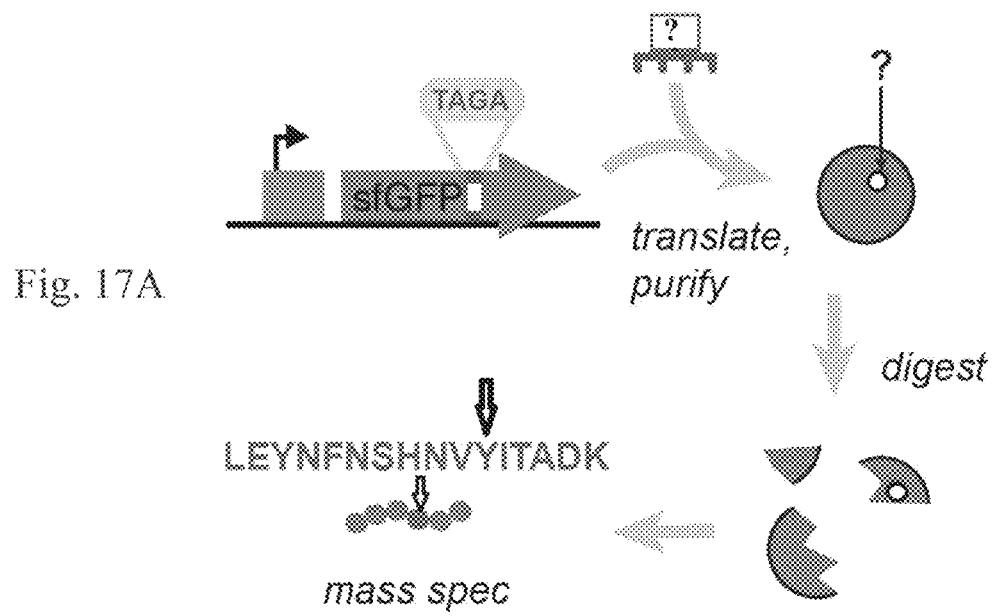
FIG. 17A-C shows schematic diagrams of an example analysis of qtRNA-TAGA charging.

Studies were performed to investigate the mechanism by which the observed qtRNA mutations confer improved translation efficiency. One hypothesis was that these mutations allow qtRNAs to be charged promiscuously by adopting identity elements of non-cognate AARSs. To investigate this possibility, the charging of each pre- and post-evolution qtRNA was characterized. To do so, a protein with a TAGA codon at permissive residue 151 was translated in sfGFP [Young, D. D., et al., (2011) Biochemistry 50, 42 1894-1900] in the presence of each qtRNA of interest and the resulting amino acid occupancy of residue 151 was measured using mass spectrometry (FIG. 17A). FIG. 17A is a schematic diagram of one strategy used to characterize the amino acid that each qtRNA incorporates. In this strategy GFP-151-TAGA was translated in the presence of the qtRNA and mass spec was used to characterize the occupancy of residue 151. Relative abundance of different species was quantified using the area under the curve for each peptide in the ion chromatogram. For Y and Q qtRNAs, the translated products detected contained the expected amino acid (Table 4).

TABLE 4

Charging of qtRNAs

| qtRNA | Limit of detection | Measured sfGFP-151 occupancy |
| --- | --- | --- |
| S-TAGA Pre-evolution | 1.47% | 100% S |
| S-TAGA-Evo1 | 0.03% | 99.7% S; 0.34% D |
| S-TAGA-Evo2 | 0.07% | 99.7% S; 0.3% D |
| R-TAGAPre- | 2.14% | 100% R |
| R-TAGA-Evo1 | 0.12% | 100% R |
| R-TAGA-Evo2 | 0.002% | 99.7% R; 0.35% Q |
| Y-TAGA-Pre- | 0.08% | 100% Y |
| Y-TAGA-Evo1 | 0.01% | 100% Y |
| Q-TAGA-Pre- | 8.76% | 100% Q |
| Q-TAGA-Evo1 | 0.05% | 100% Q |
| Q-TAGA-Evo2 | 0.76% | 100% Q |
| W-TAGA Pre- | 0.29% | 82% Q; 12% W; 6% Y |
| W-TAGA-Evo1 | 0.001% | 99.7% Q; 0.03% Y |

These results indicated that evolution of mischarging is not the evolutionary mechanism for these qtRNAs. For R and S qtRNAs, some trace mis-incorporation of Q or D, respectively, was detected at a rate of 0.3% in the evolved qtRNAs. Because a charging improvement of 0.3% would not be large enough to explain the 10× improvement in translation efficiency, this data indicated that evolution of mischarging was not the dominant evolutionary mechanism for R or S qtRNAs.

Figure 17B:
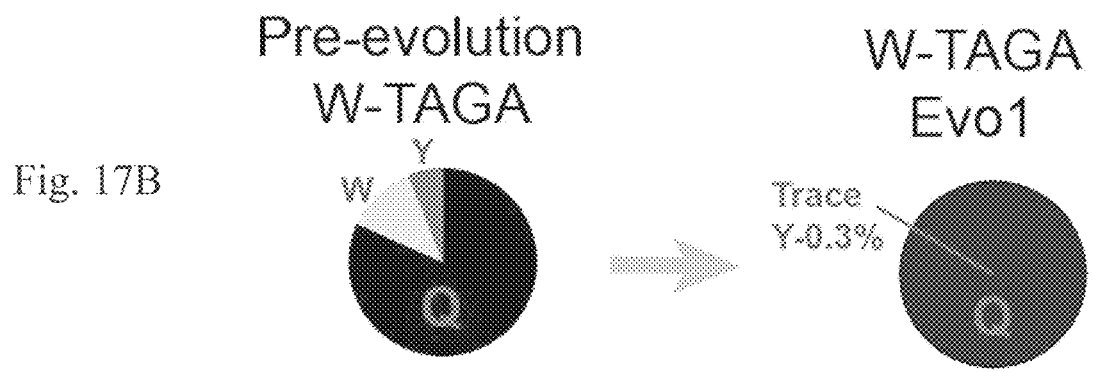
Figure 17C:
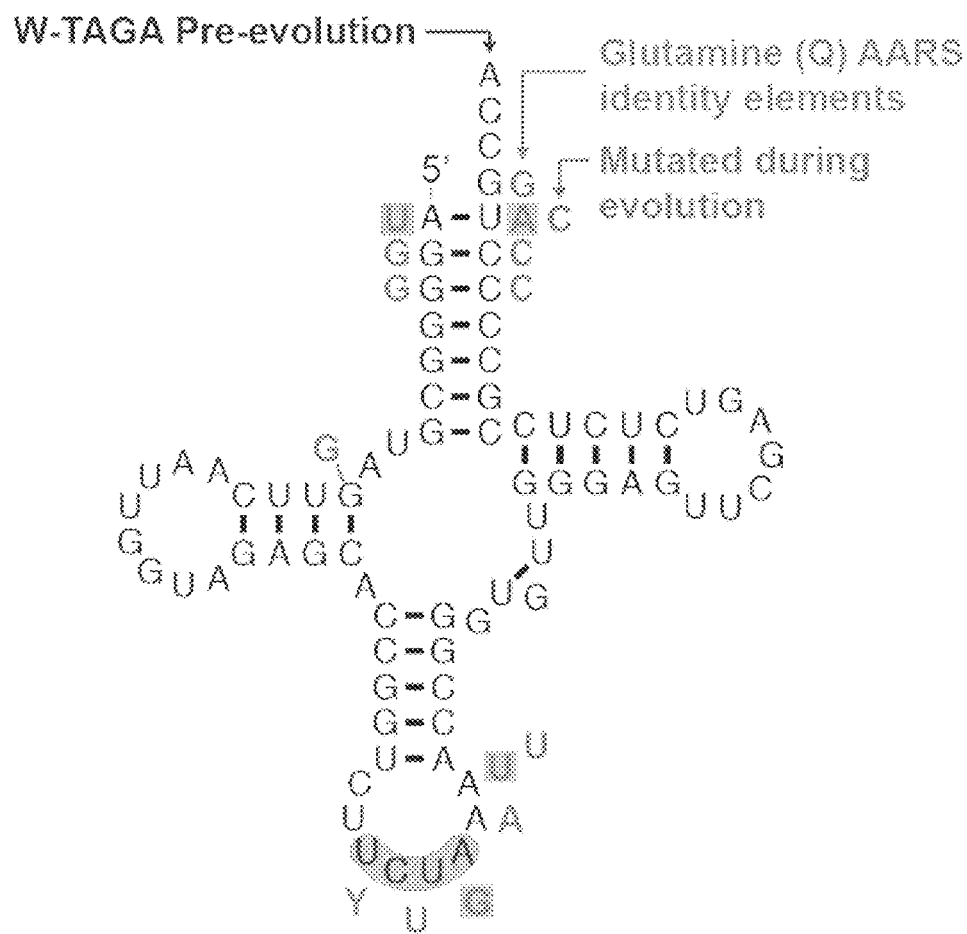

In contrast, the pre-evolution W-TAGA qtRNA was predominantly mis-charged by glutamine, while the evolved variant shows increased specificity for incorporation of glutamine (FIG. 17B). FIG. 17B illustrates mischarging evolution of W-TAGA. The W-TAGA qtRNA exhibited substantial change in its charging profile over the course of evolution. Studies were then performed to analyze tRNA identity elements that are recognized by the glutamine AARS [Giegé, R., et al., *Nucleic Acids Res.* 26, 5017-5035 (1998)]. The pre-evolution W-TAGA matched many, but not all, of these identity elements, and both mutations that occurred during evolution were found in areas where W-TAGA does not initially match the glutamine AARS identity elements (FIG. 17C). FIG. 17C shows an analysis of W-TAGA and W-TAGA-Evo (bottom-most loop UCUA) in comparison to the tRNA identity elements that are recognized by the glutamine AARS (shown adjacent to W-TAGA sequence) [Giegé, R., et al., *Nucleic Acids Res.* 26, 5017-5035 (1998)]. Identity elements required by the glutamine synthetase that were not satisfied by W-TAGA are shown adjacent to W-TAGA sequence and highlighted. Both mutations ("C" and "U" shown adjacent to identity elements) that arose during evolution occur in areas of the qtRNA with mis-matching identity elements. Y indicates a pyrimidine. The results suggested that evolution in favor of charging by a non-cognate AARS may have played a substantial role in the evolution of the W-TAGA qtRNA.

To eliminate the possibility of evolved mis-charging in the future, studies were carried out to create an amino acid specific selection. Extensive screening was carried out for amino-acid-specific residues in pIII by testing mutants of residues that were buried or whose side-chains formed close contacts [Holliger, P., et al. (1999) J. Mol. Biol. Vol. 288, 649-657; Lubkowski, et al., (1998) Nat. Struct. Biol. 5, 140-147; and Lubkowski, J., et al., (1999) Structure 7, 711-722]. However, the only highly amino-acid-specific residues identified were cysteines that participate in disulfide bridges. Studies were performed to assess the residue specificity of pIII, which tested for plaquing of ΔpIII M13 phage against a plasmid bearing either WT pIII or a one-mutant of pIII. Lack of plaques indicated non-functional pIII. Only C25 and C372 were determined to always abolish plaquing.

Example 13

Crosstalk Analysis (See Methods Above Herein)

An essential feature of canonical tRNAs is their specificity for decoding only the cognate codon or specific wobble codons. Studies were performed to determine the extent to which qtRNAs prefer the expected four-base codon over other, similar codons. To do so, the crosstalk of the evolved qtRNAs was characterized (FIG. 18A). FIG. 18A shows crosstalk profiles of evolved qtRNAs. Studies were performed that included measuring crosstalk between evolved variants and fourth-base mismatch codons, or the amber stop codon. The evolved qtRNA showed significant preference for decoding four-base codons with the matching fourth base. It showed measurable crosstalk with the three base codon TAG.

As previously reported, it was determined that qtRNAs crosstalk with four-base codons containing a mismatched fourth base, corroborating results of additional studies including those described herein and the literature (Anderson, J. C., Magliery, T. J. & Schultz, P. G. *Chem. Biol.* 9, 237-244 (2002); Curran, J. F. & Yarus, M. *Science* 238, 1545-1550 (1987); Fagan et al., 2014; Gaber, R. F. & Culbertson, M. R. *Mol. Cell. Biol.* 4, 2052-2061 (1984). This crosstalk depends on the identity of the fourth base, and similar trends in the fourth-base crosstalk pattern were observed among the three qtRNAs that were tested. In contrast, none of these qtRNAs exhibited any translation when the mismatch occurred at the third base of the codon. Studies were also performed to characterize crosstalk of TAGA-qtRNAs with translating the three-base TAG codon, a type of crosstalk that could occur from phage backbone evolution during stringent PACE selection (FIG. 17C). It was determined that crosstalk with this three-base codon was by far the most prevalent type of codon crosstalk, and depended on expression of the qtRNA as the base 3' of the TAG codon [Poole, E. S., et al. (1995) EMBO J. 14, 151-158]. These results showed that mismatch codon recognition occurred at the fourth, but not the third base of the codon. Additionally, the preference of the translation machinery for decoding triplet codons is a more prevalent form of crosstalk relative to fourth-base mismatch.

Given these results, it was determined that qtRNAs that recognize unique sequences in the first three bases of their quadruplet codons should generally be compatible, and suitable for use together as the basis for an expanded genetic code. Five of the most efficient XYZZ qtRNAs were selected to create a set whose codons obeyed this property. Luciferase reporters were used to measure the crosstalk within this set. As expected, results indicated that these qtRNAs were highly orthogonal (FIG. 18B), confirming that it would be feasible to use these qtRNAs together. FIG. 18B shows results of studies indicating that qtRNAs are orthogonal. Studies were conducted to assess the crosstalk between a set of five different qtRNAs, and it was determined that each qtRNA was highly specific for translating its own codon.

Example 14

Assessment of qtRNAs for Synthetic Biology Applications (See Methods Above Herein)

Figure 19A:
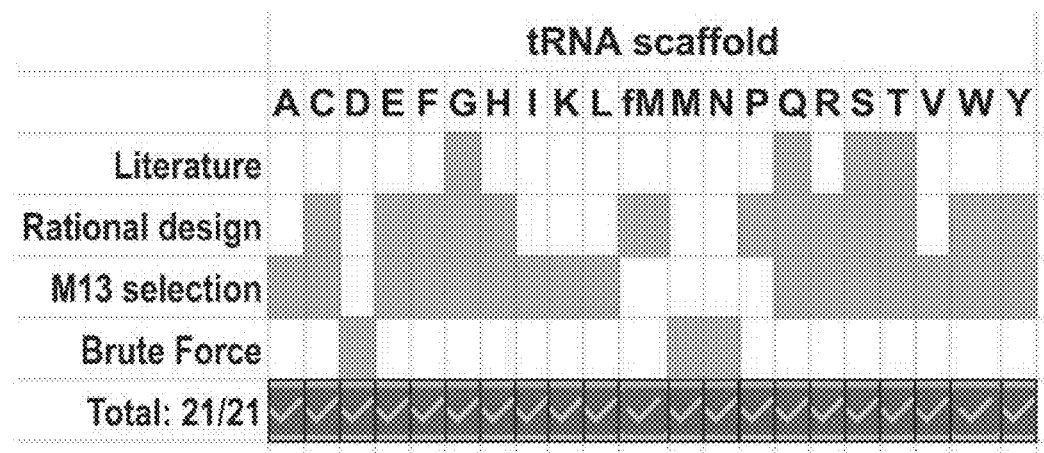
FIG. 19A-D provides charts, graphs, and a schematic diagram depicting a strategy for converting a representative tRNA scaffold for every canonical amino acid into a qtRNA.

With these results in hand, studies were performed to assess the prospective feasibility of creating an exclusively quadruplet-codon translation system. That all the tRNA scaffolds tested could be converted into corresponding qtRNAs (FIG. 19A) suggested that assembling a complete set of 20 should be possible. FIG. 19A shows results from studies designed to prepare an exclusive quadruplet-decoding translation system. Four different techniques were applied to explore the possibility of converting a representative tRNA scaffold for every canonical amino acid into a qtRNA. Together, a functional qtRNA based all 21 scaffolds is presented. In total, 55 qtRNAs were identified that decode a diverse 20 quadruplet codons (FIG. 10).

Figure 19B:
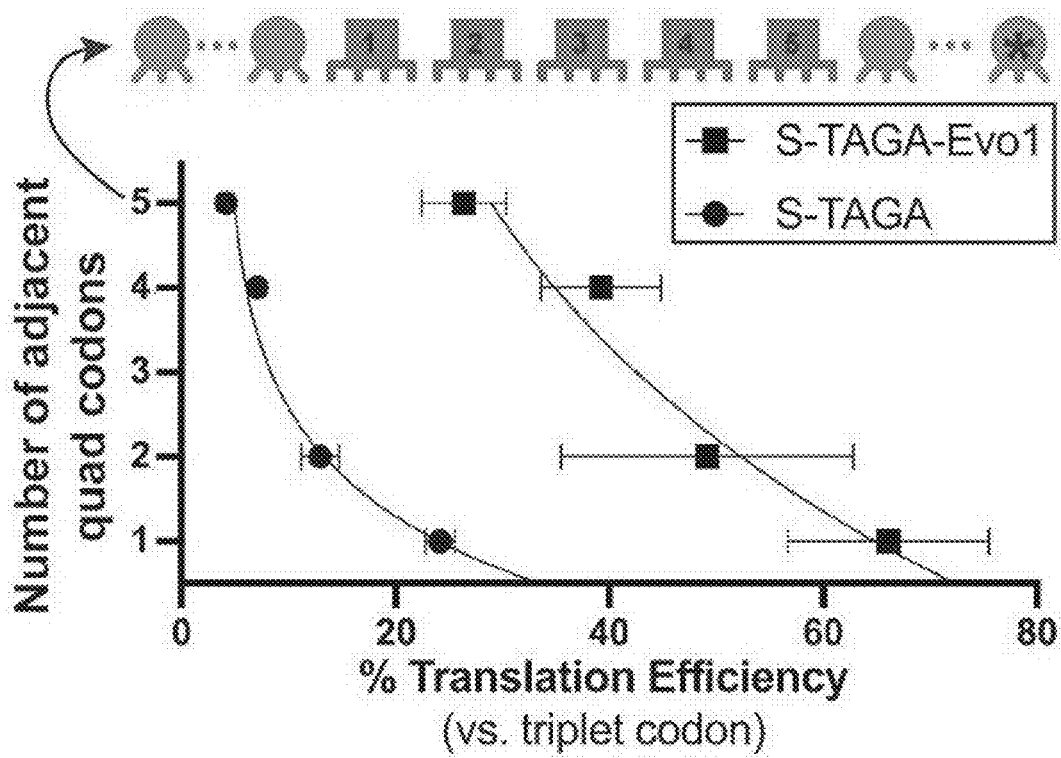
Figure 20A:
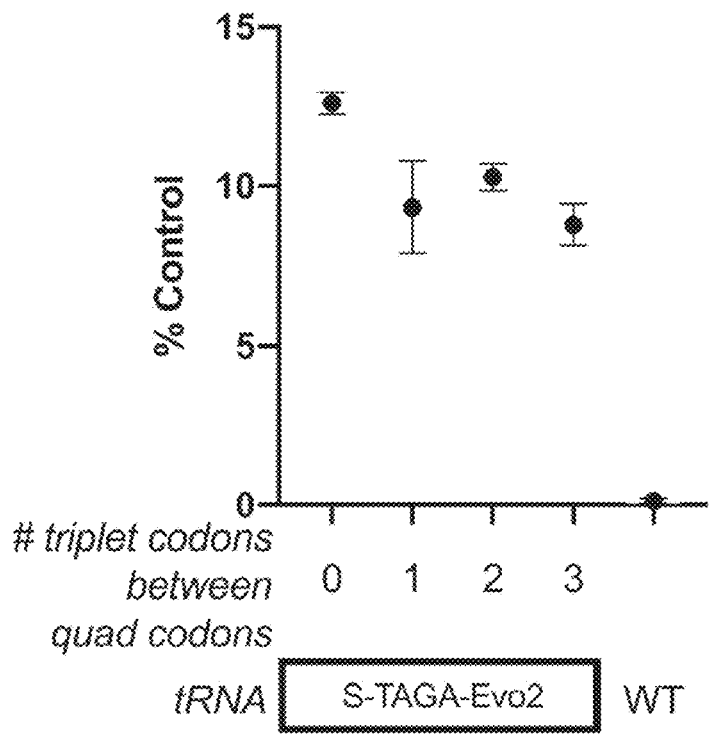
FIG. 20A-B provides a graph and illustration of an example of adjacency testing.
Figure 20B:
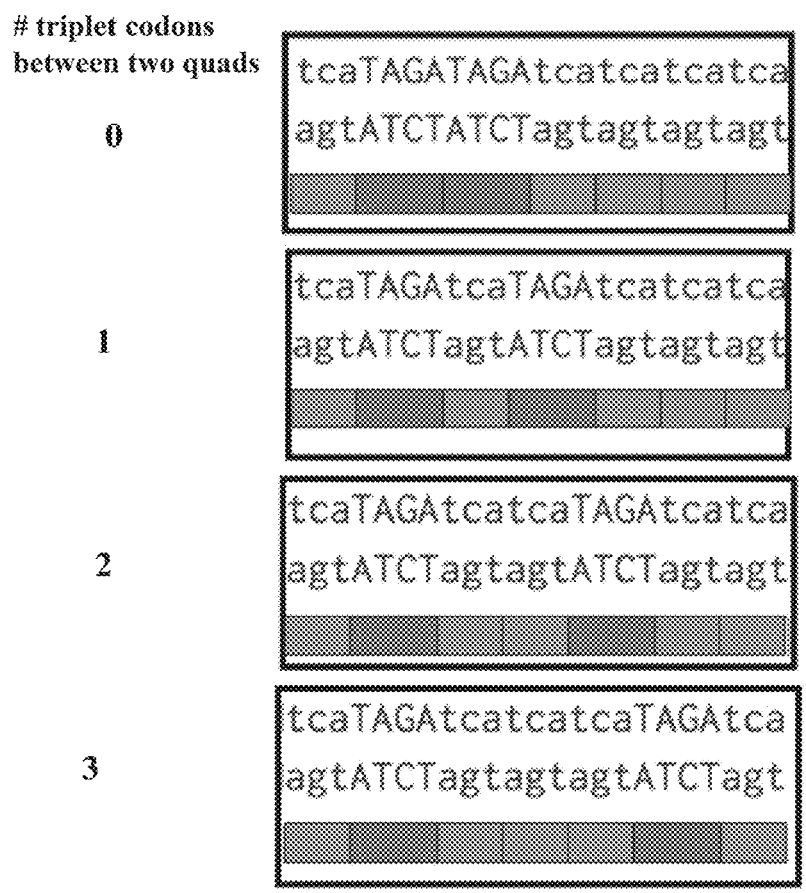

To determine whether quadruplet translation can be processive, studies were carried out and the results confirmed that the evolved S-TAGA-Evo2 could translate a linker of more than 5 adjacent quadruplet codons (FIG. 19B). FIG. 19B shows results from experiments showing the evolved serine qtRNA could translate a linker of 5 adjacent quadruplet codons inserted at luxAB-357. The efficiency of translation scaled exponentially with length. The evolved serine qtRNA's improved efficiency allowed it to efficiently translate a longer peptide relative to the pre-evolution serine qtRNA. Interestingly, a slight efficiency improvement was detected when quadruplet codons are encoded adjacent to one another (FIG. 20A-B). FIG. 20A shows results of adjacency testing performed to assess the efficiency impact of encoding two quadruplet adjacent to one another in contrast to separation by one or more triplet codons. FIG. 20B illustrates a report design in which the reporter included a 7-serine linker inserted at residue 357 that is encoded using two quadruplet codons in different positions. Each TAGA quadruplet codon appeared in the same sequence context, "a.TAGA.t".

Figure 19C:
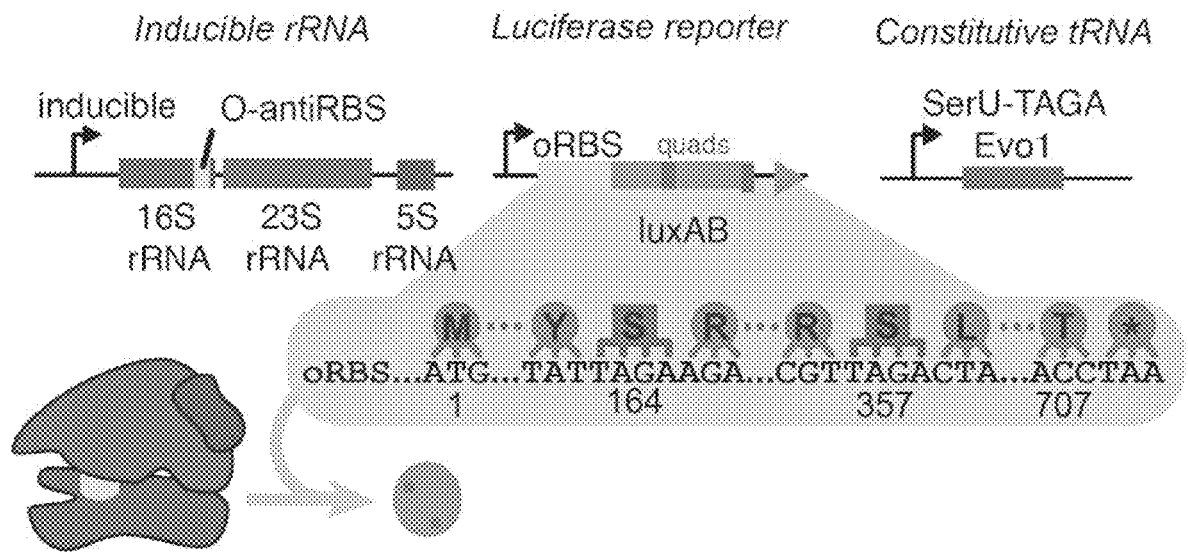
Figure 19D:
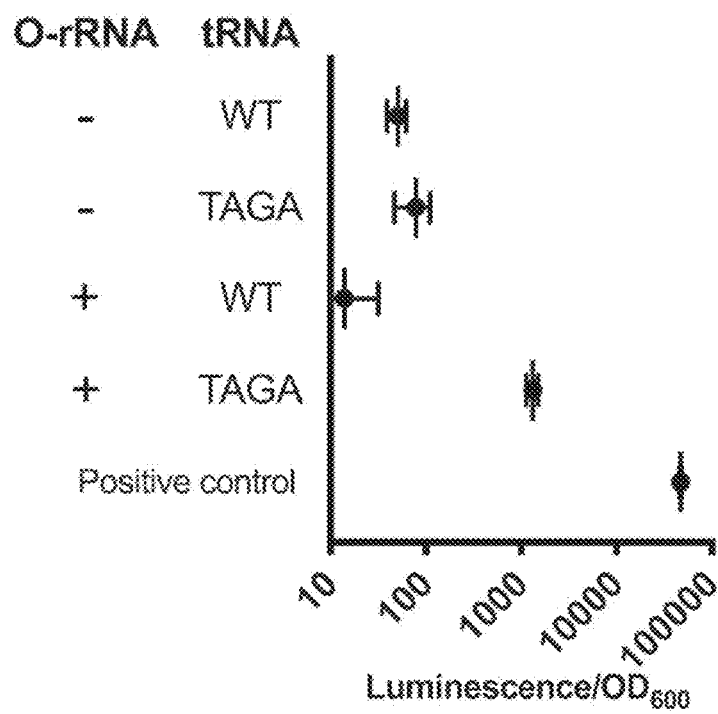

To determine whether an orthogonal ribosome can be used to translate a transcript containing quadruplet codons, an orthogonal RBS/anti-RBS pair was used, the pair had previously been used to establish a population of synthetic rRNAs in *E. coli* [Carlson, E. D., et al., (2019) Nat. Commun. 10, 3920; Rackham, 0. & Chin, *J. Nat Chem Biol* 1, 159-166 (2005)]. In the studies, the synthetic rRNA, bearing the modified anti-oRBS, was expressed from a plasmid, and the luciferase reporter transcript was directed to this ribosome via the corresponding orthogonal ribosomal binding site (oRBS) (FIG. 19C). FIG. 19C illustrates an embodiment of a construct for utilizing qtRNAs together with an orthogonal ribosome. For studies that included performing translation through the orthogonal ribosome, a three plasmid system was used. The evolved SerU-UAGA-Evo1 qtRNA was constitutively expressed and SerU-WT was used as a negative control. Orthogonal rRNA (O-rRNA), recognizing an orthogonal anti-RBS sequence, was inducibly expressed from a separate plasmid. A luciferase reporter, encoded using the orthogonal RBS sequence and two quadruplet codons, was expressed from a third plasmid. The S-TAGA-Evo1 qtRNA was used to translate a luciferase bearing a TAGA codon in two locations within the luciferase through the orthogonal ribosome, and confirmed that luminescence depended on expression of both the qtRNA and the O-rRNA (FIG. 19D). FIG. 19D shows results demonstrating that evolved qtRNAs could be used to suppress multiple quadruplet codons during translation through the orthogonal ribosome. Expression of the O-rRNA and qtRNA resulted in translation of a luciferase. The positive control was a WT luxAB encoded entirely with triplet codons. These results demonstrated that the components that have been engineered in the studies described herein can be used together with an orthogonal translation system.

EQUIVALENTS

It is to be understood that the methods and compositions that have been described above are merely illustrative applications of the principles of the invention. Numerous modifications may be made by those skilled in the art without departing from the scope of the invention.

Although the invention has been described in detail for the purpose of illustration, it is understood that such detail is solely for that purpose and variations can be made by those skilled in the art without departing from the spirit and scope of the invention which is defined by the following claims.

The contents of all literature references, publications, patents, and published patent applications cited throughout this application are incorporated herein by reference in their entirety.

What is claimed is:

1. A quadruplet decoding suppressor tRNA the sequence of which is one of SEQ ID NOs: 88-97 and 131-145.

2. A method of engineering an evolved quadruplet decoding suppressor tRNA, the method comprising:
engineering an evolved quadruplet decoding suppressor tRNA from the quadruplet decoding suppressor tRNA of claim 1, wherein the engineering comprises a phage-assisted continuing evolution (PACE) method comprising repeated enrichment of phage in *E. coli* carrying a phage propagation reporter construct resulting in directed evolution of the suppressor tRNA, optionally wherein the PACE method comprises a bacteriophage-based directed evolution method.

3. The method of claim 2, wherein the PACE method comprises determining the presence of a successfully evolved quadruplet decoding suppressor tRNA.

4. The method of claim 3, wherein the determining the presence of the successfully evolved quadruplet decoding suppressor tRNA comprises detecting a phage propagation reporter, wherein successful quadruplet decoding by the evolved suppressor tRNA results in phage propagation.

5. The method of claim 3, wherein the determining the presence of the successful evolved quadruplet decoding suppressor tRNA comprises:

(a) challenging (i) an essential phage protein encoded with one or more quadruplet codons and (ii) an evolved quadruplet decoding suppressor tRNA encoded on a phage from which the essential phage protein has been deleted to infect a plurality of *E. coli*; and (b) detecting a functional phage produced in the *E. coli*, wherein the functional phage produced indicates the presence of one or more successful quadruplet decoding(s) by the evolved quadruplet decoding suppressor tRNA, optionally wherein the essential phage protein is a pIII phage protein.

6. A method of protein translation, the method comprising:
preparing a DNA sequence comprising a quadruplet codon encoding one or more amino acids,
decoding the quadruplet codon with the quadruplet decoding suppressor tRNA of claim 1, and
translating the DNA sequence to produce a protein comprising the encoded amino acids; optionally the method further comprises assessing one or more of the structure and function of the translated protein product, optionally the decoding is performed in a cell, and optionally the cell is an engineered cell.

7. The method of claim 6, wherein the protein translation comprises both triplet and quadruplet codons, or the protein translation is an all-quadruplet protein translation.

8. The method of claim 6, wherein the cell is a bacterial cell.

9. The method of claim 6, wherein the cell is a mammalian cell, and optionally is a human cell.

10. A quadruplet decoding suppressor tRNA the sequence of which is one of SEQ ID NOs: 28-67.

11. A method of engineering an evolved quadruplet decoding suppressor tRNA, the method comprising:
engineering an evolved quadruplet decoding suppressor tRNA from the quadruplet decoding suppressor tRNA set forth in claim 10, wherein the engineering comprises a phage-assisted continuing evolution (PACE) method comprising repeated enrichment of phage in *E. coli* carrying a phage propagation reporter construct resulting in directed evolution of the suppressor tRNA, and optionally wherein the PACE method comprises a bacteriophage-based directed evolution method, and optionally wherein the PACE method comprises determining the presence of a successfully evolved quadruplet decoding suppressor tRNA.

12. The method of claim 11, wherein the determining the presence of the successfully evolved quadruplet decoding suppressor tRNA comprises detecting a phage propagation reporter, wherein successful quadruplet decoding by the evolved suppressor tRNA results in phage propagation.

13. The method of claim 11, wherein the determining the presence of the successful evolved quadruplet decoding suppressor tRNA comprises:
(a) challenging (i) an essential phage protein encoded with one or more quadruplet codons and (ii) an evolved quadruplet decoding suppressor tRNA encoded on a phage from which the essential phage protein has been deleted to infect a plurality of *E. coli*; and
(b) detecting a functional phage produced in the *E. coli*, wherein the functional phage produced indicates the presence of one or more successful quadruplet decoding(s) by the evolved quadruplet decoding suppressor tRNA.

14. A method of protein translation, the method comprising:
preparing a DNA sequence comprising a quadruplet codon encoding one or more amino acids,
decoding the quadruplet codon with the quadruplet decoding suppressor tRNA of claim 10; and
translating the DNA sequence to produce a protein comprising the encoded amino acids; optionally the method further comprises assessing one or more of the structure and function of the translated protein product, optionally the decoding is performed in a cell, and optionally the cell is an engineered cell.

15. The method of claim 14, wherein the protein translation comprises both triplet and quadruplet codons, or the protein translation is an all-quadruplet protein translation.

16. A quadruplet decoding suppressor tRNA the sequence of which is one of SEQ ID NOs: 1-9 and 11-21.

17. A method of engineering an evolved quadruplet decoding suppressor tRNA, the method comprising:
engineering an evolved quadruplet decoding suppressor tRNA from the quadruplet decoding suppressor tRNA set forth in claim 16, wherein the engineering comprises a phage-assisted continuing evolution (PACE) method comprising repeated enrichment of phage in *E. coli* carrying a phage propagation reporter construct resulting in directed evolution of the suppressor tRNA, and optionally wherein the PACE method comprises a bacteriophage-based directed evolution method, and optionally wherein the PACE method comprises determining the presence of a successfully evolved quadruplet decoding suppressor tRNA.

18. The method of claim 17, wherein the determining the presence of the successfully evolved quadruplet decoding suppressor tRNA comprises detecting a phage propagation reporter, wherein successful quadruplet decoding by the evolved suppressor tRNA results in phage propagation.

19. The method of claim 17, wherein the determining the presence of the successful evolved quadruplet decoding suppressor tRNA comprises:
(a) challenging (i) an essential phage protein encoded with one or more quadruplet codons and (ii) an evolved quadruplet decoding suppressor tRNA encoded on a phage from which the essential phage protein has been deleted to infect a plurality of *E. coli*; and
(b) detecting a functional phage produced in the *E. coli*, wherein the functional phage produced indicates the presence of one or more successful quadruplet decoding(s) by the evolved quadruplet decoding suppressor tRNA.

20. A method of protein translation, the method comprising:
preparing a DNA sequence comprising a quadruplet codon encoding one or more amino acids,
decoding the quadruplet codon with the quadruplet decoding suppressor tRNA of claim 16; and
translating the DNA sequence to produce a protein comprising the encoded amino acids, optionally, the decoding is performed in a cell, optionally, the cell is an engineered cell, and optionally, wherein:
(i) the protein translation comprises both triplet and quadruplet codons, or
(ii) the protein translation is an all-quadruplet protein translation.

\* \* \* \* \*